United States Patent
Tomiyama et al.

(10) Patent No.: US 7,045,515 B2
(45) Date of Patent: May 16, 2006

(54) β-LACTAM COMPOUNDS PROCESS FOR REPRODUCING THE SAME AND SERUM CHOLESTEROL-LOWERING AGENTS CONTAINING THE SAME

(75) Inventors: Hiroshi Tomiyama, Nagano (JP); Masayuki Yokota, Nagano (JP); Atsushi Noda, Nagano (JP); Akira Ohno, Nagano (JP)

(73) Assignee: Kotobuki Pharmaceutical Co., Ltd., Nagano (JP)

( * ) Notice: Subject to any disclaimer, the term of this patent is extended or adjusted under 35 U.S.C. 154(b) by 217 days.

(21) Appl. No.: 10/450,171

(22) PCT Filed: Feb. 20, 2002

(86) PCT No.: PCT/JP02/01481

§ 371 (c)(1),
(2), (4) Date: Jun. 11, 2003

(87) PCT Pub. No.: WO02/066464

PCT Pub. Date: Aug. 29, 2002

(65) Prior Publication Data

US 2004/0063929 A1 Apr. 1, 2004

(30) Foreign Application Priority Data

Feb. 23, 2001 (JP) ............... 2001-048202
Apr. 25, 2001 (JP) ............... 2001-128031

(51) Int. Cl.
C07D 205/08 (2006.01)
A61K 31/397 (2006.01)
A61P 3/06 (2006.01)

(52) U.S. Cl. ............... 514/210.02; 540/200; 540/360
(58) Field of Classification Search .............. None
See application file for complete search history.

(56) References Cited

U.S. PATENT DOCUMENTS 5,412,092 A    5/1995  Rey
6,703,386 B1 *  3/2004  Glombik et al. ....... 514/210.02

FOREIGN PATENT DOCUMENTS

| EP | 0 076 621 | 4/1983 |
|---|---|---|
| EP | 0 524 595 | 1/1993 |
| WO | WO 95/08532 | 3/1995 |
| WO | WO 97/16424 | 5/1997 |
| WO | WO 97/16455 | 5/1997 |

* cited by examiner

*Primary Examiner*—Mark L. Berch
(74) *Attorney, Agent, or Firm*—Sherman & Associates

(57) ABSTRACT

Novel β-lactam compounds represented by the following formula (I) or pharmaceutically acceptable salts thereof which are useful as serum cholesterol-lowering agents:

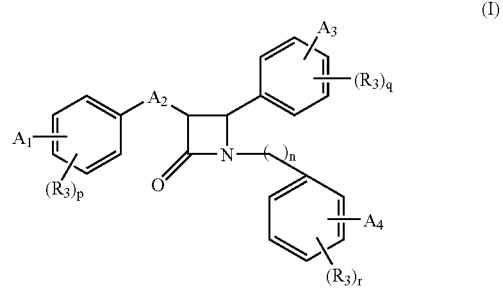

(I) wherein $A_1$, $A_3$ and $A_4$ represent each hydrogen, halogen $C_{1-5}$ alkyl, $C_{1-5}$ alkoxy, —$COOR_1$, a group represented by the following general formula (b): (b) wherein $R_1$ represents hydrogen or $C_{1-5}$ alkyl, or a group represented by the following general formula (a): (a) wherein $R_2$ represents —$CH_2OH$, —$CH_2OC(O)$—$R_1$ or —$CO_2$—$R_1$; $R_3$ represents —OH or —OC(O)—$R_1$; $R_4$ represents —$(CH_2)_k$ $R_5(CH_2)_l$— wherein K and l are each 0 or an integer of 1 or above provided k+l is an integer of not more than 10; and $R_5$ represents a single bond, —CH=CH—, —$OCH_2$—, carbonyl or —CH(OH)—; provided that at least one of $A_1$, $A_3$ and $A_4$ is a group represented by the above formula (a); $A_2$ represents $C_{1-5}$ alkyl, $C_{1-5}$ alkoxy, $C_{1-5}$ alkenyl, $C_{1-5}$ hydroxyalkyl or $C_{1-5}$ carbonylalkyl; and n, p, q and r are each an integer of 0, 1 or 2.

7 Claims, No Drawings

β-LACTAM COMPOUNDS PROCESS FOR REPRODUCING THE SAME AND SERUM CHOLESTEROL-LOWERING AGENTS CONTAINING THE SAME

FIELD OF THE INVENTION

This invention related to novel β-lactam compounds, a manufacturing method of these compounds and a serum hypocholesterolemic agent contained these compounds.

BACKGROUND OF THE INVENTION

Hypercholesterolemia is a risk factor for atherosclerotic heart disease. Atherosclerotic heart disease represents the major cause for death and cardiovascular morbidity in the world (Lipid Research Clinics Program. J. Am. Med. Assoc., 1984, 251, 351 or 365). Recently, HMG-CoA reductase inhibitors have been used as the hypocholesterolemic agents in clinical. HMG-CoA reductase inhibitors are shown to have a potent serum hypocholesterolemic activity, however, they are also reported to have unfavorable side effects (Mevacor in Physician's Desk Reference, 49th ED, Medical Economics Date Production Company, 1995, 1584). Therefore, the potent and safety serum hypocholesterolemic agents are desired.

It has been reported that naturally occuring glycosides have serum hypocholesterolemic activity (M. A. Farboodniay Jahromi et al., J. Nat. Prod., 1993, 56, 989., K. R. Price, The Chemistry and Biological Significance of Saponins in Fords and Feeding Stuffs. CRC Critical Reviews in Food Science and Nutrition, CRC Press, 1987, 26, 27). It is considered that these glycosides reduce serum cholesterol levels due to the inhibition of cholesterol absorption in small intestine (P. A. McCarthy et al., J. Med. Chem., 1996, 39, 1935). Additionally, some β-lactam compounds are reported its hypocholesterolemic activity (S. B. Rosenblum et al., J. Med. Chem., 1998, 41, 973, B. Ram et al., Indian J. Chem., 1990, 29B, 1134. U.S. Pat. No. 4,893,597).

The β-Lactam compounds have a weak inhibitiory activity on cholesterol absorption themselves, and further the glucuronide of the β-lactam compounds are more potent than the parent β-lactams. In the absorption process, the β-lactam compounds are rapid glucuronidated in small intestine after oral administration, and the resulting glucuronide derivatives are secreted through bile-duct to small intestine. These β-lactam-O-glucuronic acid conjugated derivatives are located to mucosal layer in small intestine, a site of action, and inhibit cholesterol absorption (M. van Heek et al., Brit. J. Pharmacol., 2000, 129, 1748, J. Pharmacol. Exp. Ther., 1997, 283, 157). Because of the above mentioned β-lactam compounds show serum hypocholesterolemic activity in small intestine by β-lactam-O-glucuronate conjugated derivatives, the hypocholesterolemic activities of these compounds incorporating glucose or glucuronic acid derivatives were synthesized (W. D. Vaccaro et al., Bioorg. Med. Chem. Lett., 1998, 8, 313). However, it is considered that the O-glycoside bonds in these compounds are readily hydrolyzed with glycosidase existed in small intestine after oral administration, and it is supposed the hypocholesterolemic activities of these compounds in small intestine will be reduced. Thinking about the active site of these β-lactams is mucosal layer in small intestine, the better cholesterol absorption inhibitors are required to act just only in small intestine with high efficacy and long duration. It is expected that ideal cholesterol absorption inhibitors are not to be absorbed in small intestine and eliminated without absorption in small intestine so that side effects will be reduced after the absorption in small intestine.

The principal object of the present invention is the provision of novel hypocholesterolemic agents having β-lactam moiety and C-glycoside in the molecules, which is stable to metabolism by glycosidase and hydrolysis with acids or bases. Namely, the object of the present invention is the provision of hybrid molecules with β-lactam and C-glycoside as hypocholesterolemic agents.

DETAILED DESCRIPTION OF THE INVENTION

We thought that the β-lactam and C-glycosides hybride compounds are metabolically stable against glycosidase and hydrolysis with acids or bases (R. J. Linhald et al., Tetrahedron, 54, 9913–9959, 1998). Firstly, the β-lactam-C-glycoside compounds are expected to be stable against glycosidase existed in small intestine and these hybrids were possible to locate at mucosal layer in small intestine in long time. Secondly, we thought that these compounds were little absorbed at mucosal layer in small intestine so that the side effects will be reduced. In the effort for the discovery of novel β-lactam compounds having serum hypocholesterolemic activity, we found that the compounds of the general formula (I) are the excellent hypocholesterolemic agents Namely, the compounds of the present invention have the following general formula (I):

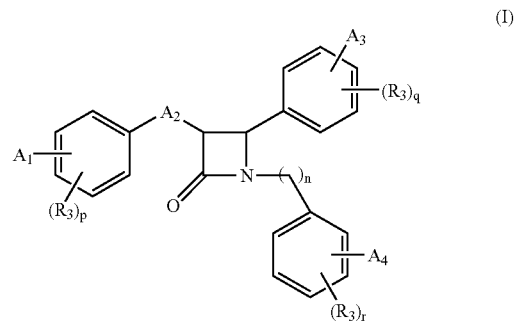

(I)

[wherein: $A_1$, $A_3$ and $A_4$ are hydrogen atom, halogen atom, alkyl group having one to five carbon atoms, alkoxy group having one to five carbon atoms, —$COOR_1$, a following formula (b):

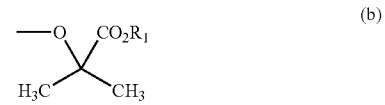

(b)

(wherein: $R_1$ is a hydrogen atom or an alkyl group having one to five carbon atoms) or a following formula (a):

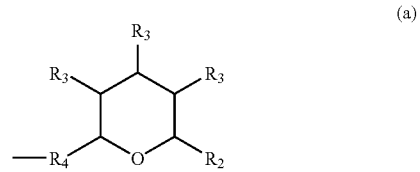

(a)

(wherein: $R_2$ is —$CH_2OH$ group, —$CH_2OC(O)$—R1 group or —$CO_2$—$R_1$ group; $R_3$ is —OH group or —$OC(O)$—$R_1$ group; R₄ is —(CH₂)ₖR₅(CH₂)ₗ— (k and l are 0 or 1 more integer; k+l is 10 or fewer integer); R₅ means bond (single bond (—), —CH=CH—, —OCH₂—, carbonyl group or —CH(OH)—.).

One of $A_1$, $A_3$ and $A_4$ in formula (I) is must be the group in above mentioned formula (a). $A_2$ is alkyl chain having one to five carbon atoms, alkoxy chain having one to five carbon atoms, alkenyl chain having one to five carbon atoms, hydroxyalkyl chain having one to five carbon atoms or carbonylalkyl chain having one to five carbon atoms. n, p, q or r are 0, 1 or 2.] or their pharmaceutical acceptable salts.

Furthermore, this invention related to a mamufacturing method of the compounds of general formula (I) and pharmaceutically acceptable salts thereof. This invention also related to a serum hypocholesterolemic agent contained the compounds of general formula (I) and their pharmaceutically acceptable salts. Additionally, this invention related to a serum hypocholesterolemic agent by combination therapy of the compounds of general formula (I) and β-lactamase inhibitors.

Pharmaceutically acceptable salts of this invention are mentioned as follow. As mineral basic salt, sodium or potassium salts of general formula (I) are mentioned. As organic acid salts, succinic acid, maleic acid, toluenesulfonic acid or tartaric acid are mentioned. The compounds of general formula (I) can be orally administered alone or in combination with pharmaceutically acceptable carriers or diluents. They may be administed orally as powders, granules, tablets, capsules by standard pharmaceutical techniques and also parenterally as intrarectal administrations, suppositories and injections.

The dosage is ranging from 0.01–1000 mg per day and administered in a single dose or several doses. However, variations will necessarily occur depending upon the conditions, age and body weight of the recipient. Additionally, serum hypocholesterolemic activity is enhanced in the combination with the compounds of the general formula (I) and β-lactamase inhibitors.

The β-lactumase inhibitors such as clavulanic acid are a drug which inhibit to degradation of β-lactum ring by bacteria.

The compounds are exemplified as follows, although they did not be limited.

(1) (4S*,3R*)-4-{4-[(2S,5S,3R,4R,6R)-3,4,5-Trihydroxy-6-(hydroxymethyl)perhydro-2H-pyran-2-yl]phenyl}-1-(4-fluorophenyl)-3-[3-(4-fluorophenyl)propyl]azetidine-2-one (2) (4S*,3R*)-4-(4-{[(2S,5S,3R,4R,6R)-3,4,5-Trihydroxy-6-(hydroxymethyl)perhydro-2H-pyran-2-yl]methyl}phenyl)-1-(4-fluorophenyl)-3-[3-(4-fluorophenyl)propyl]azetidine-2-one (3) (3S,2R,4R,5R,6R)-2-[(4-{(4S*,3R*)-1-(4-Fluorophenyl)-3-[3-(4-fluorophenyl)propyl]-2-oxoazetidine-4-yl}phenyl)methyl]-4,5-diacetyloxy-6-(acetoxymethyl)perhydro-2H-pyran-3-ylacetate (4) (4S*,3R*)-4-(4-{[(2S,5S,3R,4R,6R)-3,4,5-Trihydroxy-6-(hydroxymethyl)perhydro-2H-pyran-2-yl]methyl}phenyl)-1-(4-chlorophenyl)-3-[3-(4-fluorophenyl)propyl]azetidine-2-one (5) (4S*,3R*)-4-(4-{[(5S,2R,3R,4R,6R)-3,4,5-Trihydroxy-6-(hydroxymethyl)perhydro-2H-pyran-2-yl]methyl}phenyl)-1-(4-methoxyphenyl)-3-[3-(4-fluorophenyl)propyl]azetidine-2-one (6) (3S,2R,4R,5R,6R)-2-[(4-{(4S*,3R*)-1-(4-Methoxyphenyl)-3-[3-(4-fluorophenyl)propyl]-2-oxoazetidine-4-yl}phenyl)methyl]-4,5-diacetyloxy-6-(acetoxymethyl)perhydro-2H-pyran-3-ylacetate (7) (4S*,3R*)-4-(4-{[(5S,2R,3R,4R,6R)-3,4,5-Trihydroxy-6-(hydroxymethyl)perhydro-2H-pyran-2-yl]methyl}phenyl)-1-(4-methylphenyl)-3-[3-(4-fluorophenyl)propyl]azetidine-2-one (8) (3S,2R,4R,5R,6R)-2-[(4-{(4S*,3R*)-1-(4-Methylphenyl)-3-[3-(4-fluorophenyl)propyl]-2-oxoazetidine-4-yl}phenyl)methyl]-4,5-diacetyloxy-6-(acetoxymethyl)perhydro-2H-pyran-3-ylacetate (9) (4S*,3R*)-4-(4-{[(5S,2R,3R,4R,6R)-3,4,5-Trihydroxy-6-(hydroxymethyl)perhydro-2H-pyran-2-yl]methyl}phenyl)-1-phenyl-3-[3-(4-fluorophenyl)propyl]azetidine-2-one

(10) (3S,2R,4R,5R,6R)-2-[(4-{(4S*,3R*)-1-phenyl-3-[3-(4-fluorophenyl)propyl]-2-oxoazetidine-4-yl}phenyl)methyl]4,5-diacetyloxy-6-(acetoxymethyl)perhydro-2H-pyran-3-ylacetate

(11) (4S*,3R*)-4-(4-{[(5S,2R,3R,4R,6R)-3,4,5-Trihydroxy-6-(hydroxymethyl)perhydro-2H-pyran-2-yl]methyl}phenyl)-1-(4-fluorophenyl)-3-[3-(phenyl)propyl]azetidine-2-one

(12) (4S*,3R*)-4-(4-{[(5S,2R,3R,4R,6R)-3,4,5-Trihydroxy-6-(hydroxymethyl)perhydro-2H-pyran-2-yl]methyl}phenyl)-1-(4-fluorophenyl)-3-[2-(4-fluorophenoxy)ethyl]azetidine-2-one

(13) (3S,2R,4R,5R,6R)-2-[(4-{(4S*,3R*)-1-(4-Fluorophenyl)-3-[2-(4-fluorophenoxy)ethyl]-2-oxoazetidine-4-yl}phenyl)methyl]-4,5-diacetyloxy-6-(acetoxymethyl)perhydro-2H-pyran-3-ylacetate

(14) (4S*,3R*)-4-(4-{[(4S,5S,2R,3R,6R)-3,4,5-Trihydroxy-6-(hydroxymethyl)perhydro-2H-pyran-2-yl]methoxy}phenyl)-1-(4-fluorophenyl)-3-[3-(4-fluorophenyl)propyl]azetidine-2-one

(15) (4S*,3R*)-4-(4-{[(4S,5S,2R,3R,6R)-3,4,5-Trihydroxy-6-(hydroxymethyl)perhydro-2H-pyran-2-yl]methoxy}phenyl)-1-(4-fluorophenyl)-3-[2-(4-fluorophenoxy)ethyl]azetidine-2-one

(16) (4S*,3R*)-4-(4-{[(4S,5S,2R,3R,6R)-3,4,5-Trihydroxy-6-(hydroxymethyl)perhydro-2H-pyran-2-yl]methoxy}phenyl)-1-phenylmethyl-3-[3-(4-fluorophenyl)propyl]azetidine-2-one

(17) (2S,3S,4R,5R,6R)-6-[4-{(4S*,3R*)-1-(4-Fluorophenyl)-3-[3-(4-fluorophenyl)propyl]-2-oxoazetidine-4-yl}phenyl)methyl]-3,4,5-trihydroxyperhydro-2H-pyran-2-carboxylic acid

(18) 2-{4-[(4S*,3R*)-4-{[(5S,2R,3R,4R,6R)-3,4,5-Trihydroxy-6-(hydroxymethyl)perhydro-2H-pyran-2-yl]methyl}phenyl-3-[3-(4-fluorophenyl)propyl]-2-oxoazetidinyl]phenoxy}-2-methylpropionic acid ethyl ester

(19) 2-{4-[(4S*,3R*)-4-{[(5S,2R,3R,4R,6R)-3,4,5-Trihydroxy-6-(hydroxymethyl)perhydro-2H-pyran-2-yl]methyl}phenyl-3-[3-(4-fluorophenyl)propyl]-2-oxoazetidinyl]phenoxy}-2-methylpropionic acid

(20) 2-{4-[(4S*,3R*)-4-{[(5S,2R,3R,4R,6R)-3,4,5-Trihydroxy-6-(hydroxymethyl)perhydro-2H-pyran-2-yl]methyl}phenyl-3-[3-(4-methylphenyl)propyl]-2-oxo azetidinyl]phenoxy}-2-methylpropionic acid ethyl ester

(21) 2-{4-[(4S*,3R*)-4-{[(5S,2R,3R,4R,6R)-3,4,5-Trihydroxy-6-(hydroxymethyl)perhydro-2H-pyran-2-yl]methyl}phenyl-3-[3-(4-methylphenyl)propyl]-2-oxoazetidinyl]phenoxy}-2-methylpropionic acid

(22) (4S,3R)-3-[(3S)-3-(4-Fluorophenyl)-3-hydroxypropyl]-4-(4-{[(2S,5S,3R,4R,6R)-3,4,5-trihydroxy-6-(hydroxymethyl)perhydro-2H-pyran-2-yl]methyl}phenyl)-1-(4-fluorophenyl)azetidine-2-one

(23) (4S,3R)-3-[(3S)-3-(4-Fluorophenyl)-3-hydroxypropyl]-4-(4-{[(2S,5S,3R,4R,6R)-3,4,5-trihydroxy-6-(hydroxymethyl)perhydro-2H-pyran-2-yl]methyl}phenyl)-1-phenylazetidine-2-one

(24) (4S,3R)-3-[(3S)-3-(4-Fluorophenyl)-3-hydroxypropyl]-4-(4-{[(2S,5S,3R,4R,6R)-3,4,5-trihydroxy-6-(hydroxymethyl)perhydro-2H-pyran-2-yl]methyl}phenyl)-1-(4-methylphenyl)azetidine-2-one

(25) (4S,3R)-4-(4-{[(5S,2R,3R,4R,6R)-3,4,5-Trihydroxy-6-(hydroxymethyl)perhydro-2H-pyran-2-yl)methyl}phenyl)-1-(4-fluorophenyl)-3-[3-(4-fluorophenyl)propyl]azetidine-2-one

(26) (4S,3R)-4-(4-{[(2S,5S,3R,4R,6R)-3,4,5-Trihydroxy-6-(hydroxymethyl)perhydro-2H-pyran-2-yl]methyl}phenyl)-1-(4-fluorophenyl)-3-[3-(4-fluorophenyl)-3-oxopropyl]azetidine-2-one

(27) (4S,3R)-4-(4-{[(2S,5S,3R,4R,6R)-3,4,5-Trihydroxy-6-(hydroxymethyl)perhydro-2H-pyran-2-yl]methyl}phenyl)-1-phenyl-3-[3-(4-fluorophenyl)-3-oxopropyl]azetidine-2-one

(28) (4S,3R)-4-(4-{[(2S,5S,3R,4R,6R)-3,4,5-Trihydroxy-6-(hydroxymethyl)perhydro-2H-pyran-2-yl]methyl}phenyl)-1-(4-methylphenyl)-3-[3-(4-fluorophenyl)-3-oxopropyl]azetidine-2-one

(29) 4-[(4S,3R)-3-[(3S)-3-(4-Fluorophenyl)-3-hydroxypropyl]-4-(4-{[(2S,5S,3R,4R,6R)-3,4,5-trihydroxy-6-(hydroxymethyl)perhydro-2H-pyran-2-yl]methyl}phenyl)-2-oxoazetidinyl]benzoic acid

(30) 4-[(4S,3R)-4-(4-{[(2S,5S,3R,4R,6R)-3,4,5-Trihydroxy-6-(hydroxymethyl)perhydro-2H-pyran-2-yl]methyl}phenyl)-3-[3-(4-fluorophenyl)-3-oxopropyl]-2-oxoazetidinyl]benzoic acid

(31) 4-[(4S,3R)-4-(4-{[(2S,5S,3R,4R,6R)-3,4,5-Trihydroxy-6-(hydroxymethyl)perhydro-2H-pyran-2-yl]methyl}phenyl)-3-[3-(4-fluorophenyl)propyl]-2-oxoazetidinyl]benzoic acid

(32) 3-[(2E)-3-(4-Fluorophenyl)-2-propenyl](4S,3R)-4-(4-{[(2S,5S,3R,4R,6R)-3,4,5-Trihydroxy-6-(hydroxymethyl)perhydro-2H-pyran-2-yl]methyl}phenyl)-1-(4-fluorophenyl)azetidine-2-one

(33) (4S,3R)-4-{4-{[(2S,5S,3R,4R,6R)-3,4,5-Trihydroxy-6-(hydroxymethyl)perhydro-2H-pyran-2-yl]phenyl}-1-(4-fluorophenyl)-3-[3-(4-fluorophenyl)propyl]azetidine-2-one

(34) (4S,3R)-4-{4-{[(2S,5S,3R,4R,6R)-3,4,5-Trihydroxy-6-(hydroxymethyl)perhydro-2H-pyran-2-yl]phenyl}-1-(4-fluorophenyl)-3-[3-(4-fluorophenyl)-3-oxopropyl]azetidine-2-one

(35) (4S,3R)-3-[(3S)-3-(4-Fluorophenyl)-3-hydroxypropyl]-4-{4-{[(2S,5S,3R,4R,6R)-3,4,5-trihydroxy-6-(hydroxymethyl)perhydro-2H-pyran-2-yl]phenyl}-1-(4-fluorophenyl)azetidine-2-one

(36) (4S,3R)-3-[(3S)-3-(4-Fluorophenyl)-3-hydroxypropyl]-4-{4-{[(2S,5S,3R,4R,6R)-3,4,5-trihydroxy-6-(hydroxymethyl)perhydro-2H-pyran-2-yl]phenyl}-1-(4-methylphenyl)azetidine-2-one

(37) (4S,3R)-3-[(3S)-3-(4-Fluorophenyl)-3-hydroxypropyl]-4-[(2S,5S,3R,4R,6R)-3,4,5-trihydroxy-6-(hydroxymethyl)perhydro-2H-pyran-2-yl]-1-phenylazetidine-2-one

(38) (4S,3R)-3-[(3S)-3-(4-Fluorophenyl)-3-hydroxypropyl]-1-(4-{[(2S,5S,3R,4R,6R)-3,4,5-trihydroxy-6-(hydroxy methyl)perhydro-2H-pyran-2-yl]methyl}phenyl)-1-(4-fluorophenyl)azetidine-2-one

(39) (4S,3R)-3-[(3S)-3-(4-{[(2S,5S,3R,4R,6R)-3,4,5-Trihydroxy-6-(hydroxymethyl)perhydro-2H-pyran-2-yl]methyl}phenyl)-3-hydroxypropyl]-1-phenyl-4-(4-fluorophenyl)azetidine-2-one

(40) (4R*,3R*)-4-(4-{[(5S,2R,3R,4R,6R)-3,4,5-Trihydroxy-6-(hydroxymethyl)perhydro-2H-pyran-2-yl]methyl}phenyl)-3-[3-(4-fluorophenyl)propyl]-1-(4-fluorophenyl)azetidine-2-one

(41) 3-((3S)-3-Hydroxy-3-phenylpropyl)(4S,3R)-4-(4-{[(2S,5S,3R,4R,6R)-3,4,5-trihydroxy-6-(hydroxymethyl)perhydro-2H-pyran-2-yl]methyl}phenyl)-1-phenylazetidine-2-one

(42) 4-[3-((3S)-3-(4-Fluorophenyl)-3-hydroxypropyl](4S,3R)-4-(4-{[(2S,5S,3R,4R,6R)-3,4,5-trihydroxy-6-(hydroxymethyl)perhydro-2H-pyran-2-yl]methyl}phenyl)-2-oxoazetidinyl]benzoic acid ethyl ester

(43) 4-(4-{[(5S,2R,3R,4R,6R)-3,4,5-Trihydroxy-6-(hydroxymethyl)perhydro-2H-pyran-2-yl]methyl}phenyl)(4S,3R)-1-(4-methylphenyl)-3-[3-(4-fluorophenoxy)ethyl]azetidine-2-one

(44) 3-(3-Phenylpropyl)(4S,3R)-4-(4-{[(5S,3R,4R,6R)-3,4,5-trihydroxy-6-(hydroxymethyl)perhydro-2H-pyran-2-yl]methyl}phenyl)-1-phenylazetidine-2-one

(45) (4S,3R)-3-[(3S)-3-(4-Fluorophenyl)-3-hydroxypropyl]4-(4-{[(2S,5S,3R,4R,6R)-3,4,5-trihydroxy-6-(hydroxymethyl)perhydro-2H-pyran-2-yl]ethene}phenyl)-1-(4-fluorophenyl)azetidine-2-one

(46) (4S,3R)-3-[(3S)-3-(4-Fluorophenyl)-3-hydroxypropyl]4-(4-([(2S,5S,3R,4R,6R)-3,4,5-trihydroxy-6-(hydroxymethyl)perhydro-2H-pyran-2-yl]ethyl}phenyl)-1-(4-fluorophenyl)azetidine-2-one

(47) (4S,3R)-3-[(3S)-3-(4-Fluorophenyl)-3-hydroxypropyl]4-(4-{[(2S,5S,3R,4R,6R)-3,4,5-trihydroxy-6-(hydroxymethyl)perhydro-2H-pyran-2-yl]-1-propen-3-yl}phenyl-1-(4-fluorophenyl)azetidine-2-one

(48) (4S,3R)-3-[(3S)-3-(4-Fluorophenyl)-3-hydroxypropyl]-4-(4-{[(2S,5S,3R,4R,6R)-3,4,5-trihydroxy-6-(hydroxymethyl)perhydro-2H-pyran-2-yl]propyl}phenyl-1-(4-fluorophenyl)azetidine-2-one

(49) 3-((3S)-(4-[(2S,5S,3R,4R,6R)-3,4,5-Trihydroxy-6-(hydroxymethyl)perhydro-2H-pyran-2-yl]phenyl}-3-hydroxypropyl)(4S,3R)-1,4-bis(4-fluorophenyl)azetidine-2-one

(50) (4S,3R)-3-[(3S)-3-(4-Fluorophenyl)-3-hydroxypropyl]4-(4-{[(2S,5S,3R,4R,6R)-3,4,5-trihydroxy-6-(hydroxymethyl)perhydro-2H-pyran-2-yl]methoxypropyl-3-yl}phenyl-1-(4-fluorophenyl)azetidine-2-one

(51) (4S,3R)-3-[(3S)-3-(4-Fluorophenyl)-3-hydroxypropyl]4-(4-{[(2S,5S,3R,4R,6R)-3,4,5-trihydroxy-6-(hydroxymethyl)perhydro-2H-pyran-2-yl]methoxy-2-propen-3-yl}phenyl-1-(4-fluorophenyl)azetidine-2-one

(52) (4S,3R)-3-[(3S)-3-(4-Fluorophenyl)-3-hydroxypropyl]4-(4-{[(2S,5S,3R,4R,6R)-3,4,5-trihydroxy-6-(hydroxymethyl)perhydro-2H-pyran-2-yl]-1-buten-4-yl}phenyl-1-(4-fluorophenyl)azetidine-2-one

(53) (4S,3R)-3-[(3S)-3-(4-Fluorophenyl)-3-hydroxypropyl]4-(4-{[(2S,5S,3R,4R,6R)-3,4,5-trihydroxy-6-(hydroxymethyl)perhydro-2H-pyran-2-yl]butyl}phenyl-1-(4-fluorophenyl)azetidine-2-one

(54) (4S,3R)-3-[(3S)-3-(4-Fluorophenyl)-3-hydroxypropyl]-4-(4-{[(2S,5S,3R,4R,6R)-3,4,5-trihydroxy-6-(hydroxymethyl)perhydro-2H-pyran-2-yl]-1-penten-5-yl}phenyl-1-(4-fluorophenyl)azetidine-2-one

(55) (4S,3R)-3-[(3S)-3-(4-Fluorophenyl)-3-hydroxypropyl]
4-(4-{[(2S,5S,3R,4R,6R)-3,4,5-trihydroxy-6-(hydroxymethyl)perhydro-2H-pyran-2-yl]pentyl}phenyl-1-(4-fluorophenyl)azetidine-2-one
(56) (4S,3R)-3-[(3S)-3-(4-Fluorophenyl)-3-hydroxypropyl]-4-(4-{[(2S,5S,3R,4R,6R)-3,4,5-trihydroxy-6-(hydroxymethyl)perhydro-2H-pyran-2-yl]ethyl-2-yl)phenyl-1-phenylazetidine-2-one
(57) (4S,3R)-3-[(3S)-3-(4-Fluorophenyl)-3-hydroxypropyl]
4-(4-{[(2S,5S,3R,4R,6R)-3,4,5-trihydroxy-6-(hydroxymethyl)perhydro-2H-pyran-2-yl]ethyl-2-yl}phenyl-1-(4-methylphenyl)azetidine-2-one
(58) (4S,3R)-3-[(3S)-3-(4-Fluorophenyl)-3-hydroxypropyl]
4-(4-{[(2S,5S,3R,4R,6R)-3,4,5-trihydroxy-6-(carboxyl)perhydro-2H-pyran-2-yl]ethyl-2-yl}phenyl-1-(phenyl)azetidine-2-one Typical preparation of the compounds according to the invention are shown, but they are not limited to these compounds. The compounds showing the specific rotation are either prepared as the optically active compound or separated as optically active compounds by the suitable methods and determined the specific rotation.

The compound of general formula (I) can be obtained as follows.

| No. | Structure | mp (° C.) | $[\alpha]_D^{25}$/(C, Solv.) |
|---|---|---|---|
| 1 | 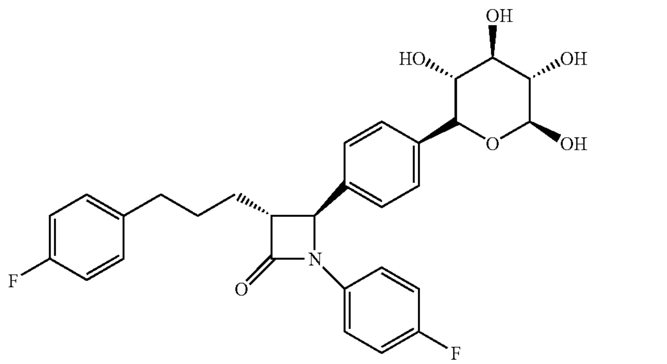 | 89–90 | −40.4 (C = 0.5, MeOH) |
| 2 | 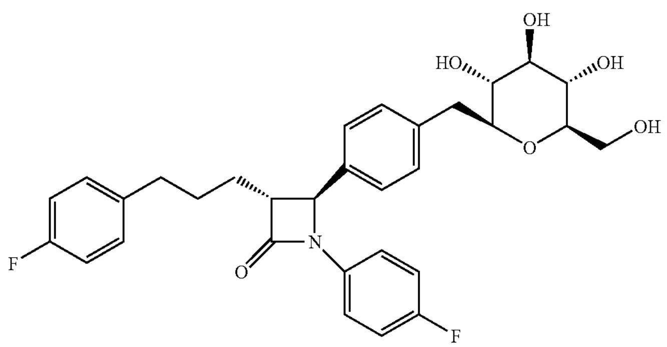 | 110–112 | −33.2 (C = 0.5, MeOH) |
| 3 | 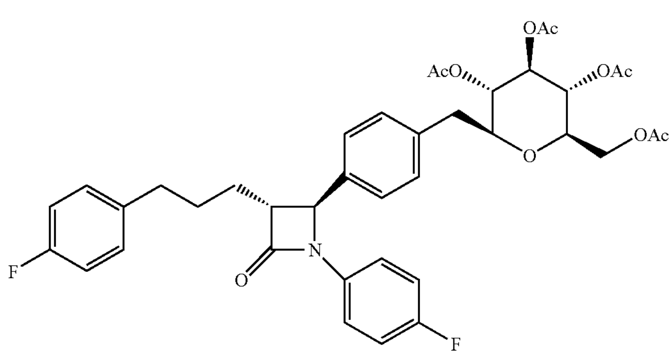 | 56–58 | |

| No. | Structure | mp (° C.) | $[\alpha]_D^{25}$/(C, Solv.) |
|---|---|---|---|
| 4 | 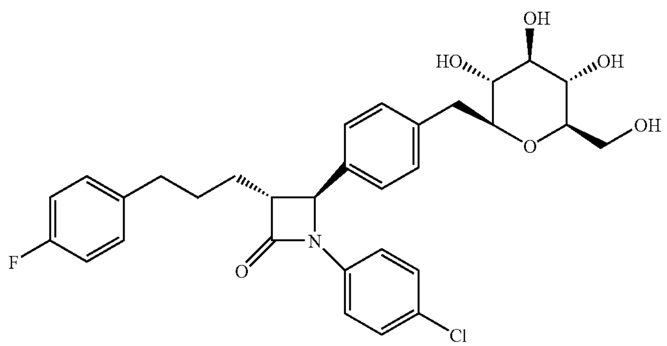 | 76–78 | |
| 5 | 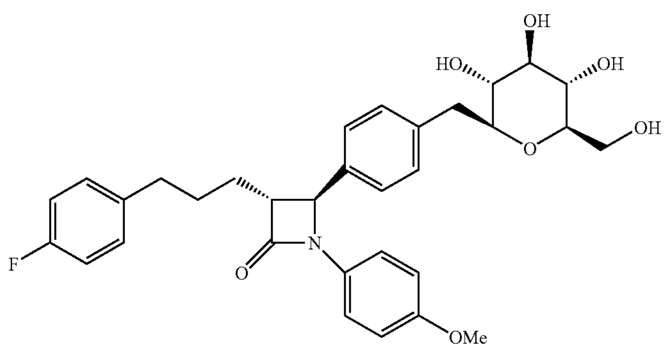 | 73–75 | |
| 6 | 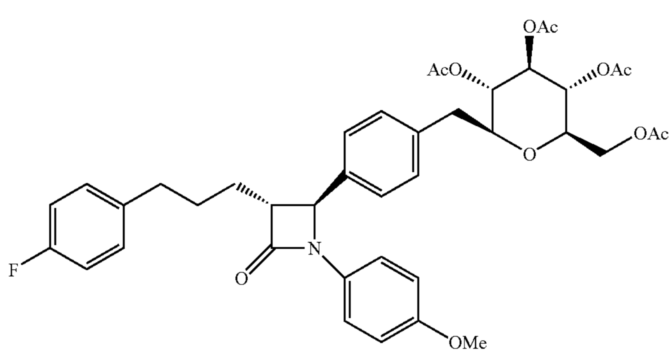 | 60–62 | |
| 7 | 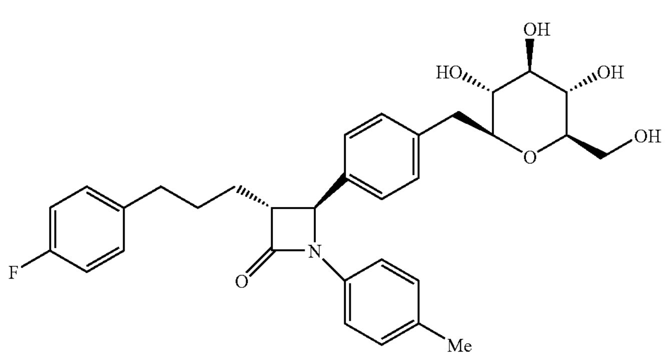 | 80–82 | −46.7 (C = 0.3, MeOH) |

-continued

| No. | Structure | mp (° C.) | $[\alpha]_D^{25}$/(C, Solv.) |
|---|---|---|---|
| 8 | 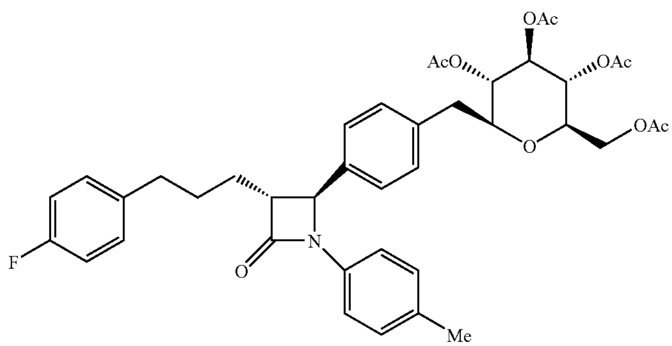 | 56–58 | |
| 9 | 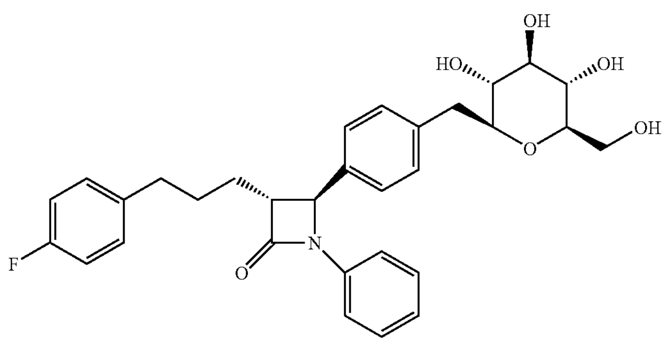 | 84–86 | −40.4 (C = 0.5, MeOH) |
| 10 | 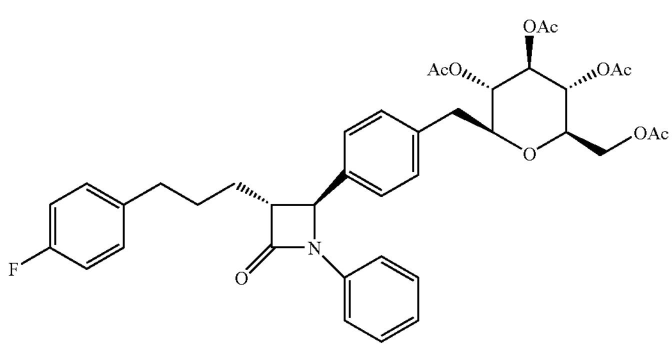 | 60–61 | |
| 11 | 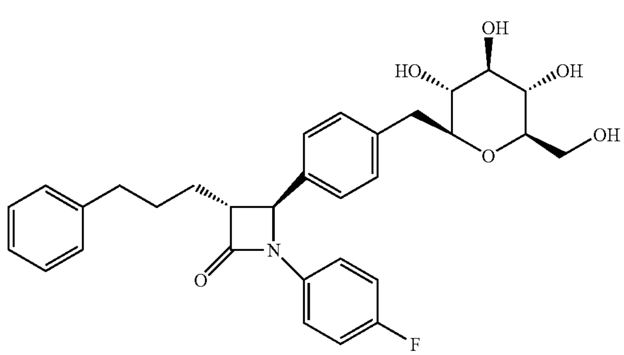 | 74–75 | |

-continued

| No. | Structure | mp (° C.) | $[\alpha]_D^{25}$/(C, Solv.) |
|---|---|---|---|
| 12 | 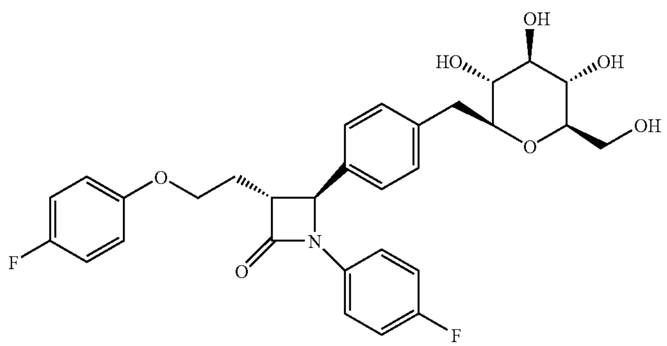 | 65–67 | −40.4 (C = 0.5, CHCl$_3$) |
| 13 | 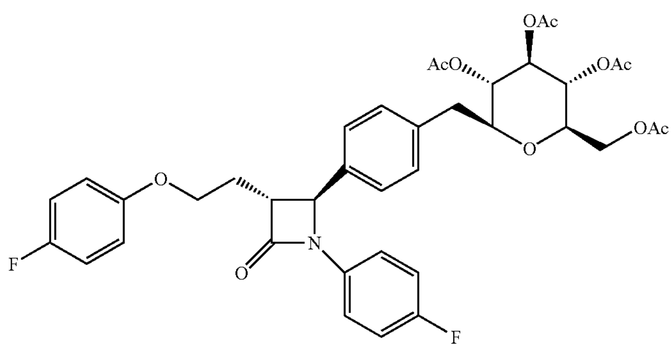 | 64–66 | |
| 14 | 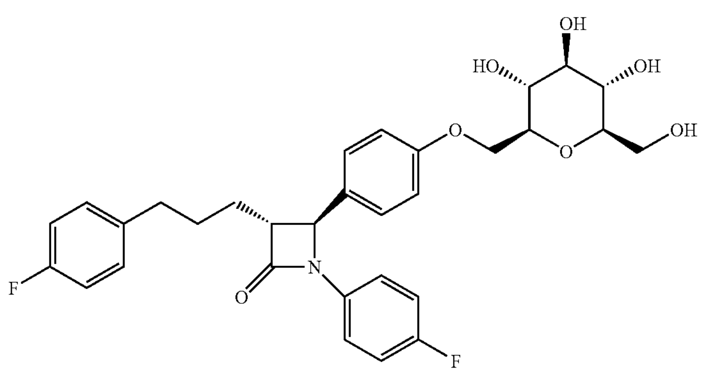 | 61–62 | |
| 15 | 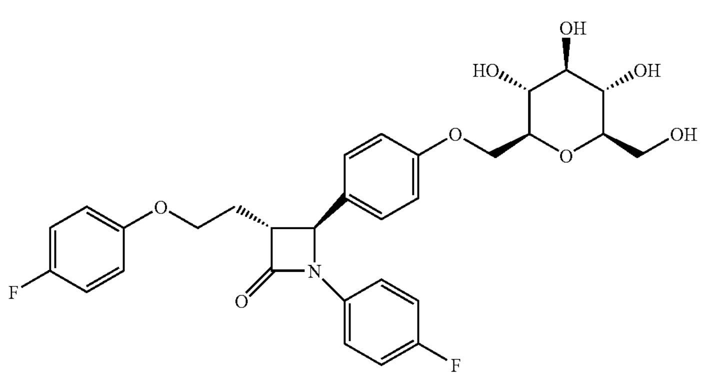 | 64–65 | |

-continued

| No. | Structure | mp (° C.) | $[\alpha]_D^{25}$/(C, Solv.) |
|-----|-----------|-----------|------------------------------|
| 16  | 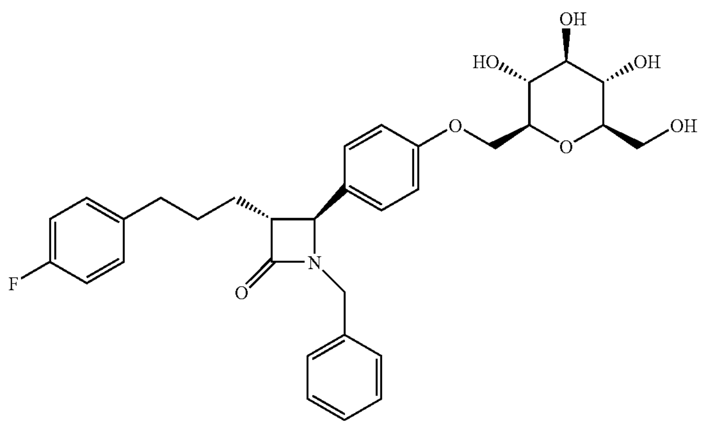          | 73–75     |                              |
| 17  | 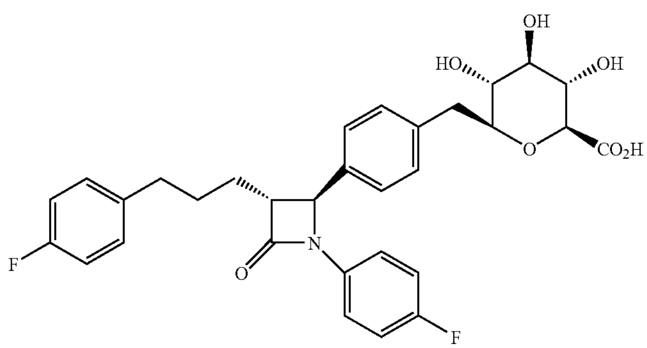          | 105–106   |                              |
| 18  | 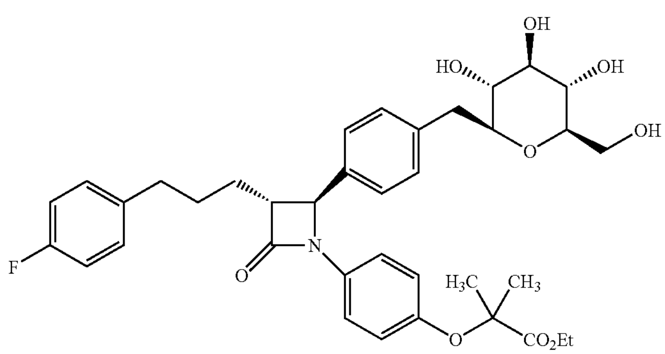          | 73–74     |                              |
| 19  | 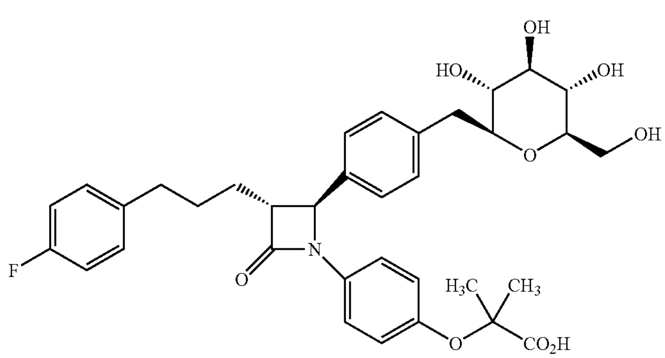          | 170–172   |                              |

-continued

| No. | Structure | mp (° C.) | $[\alpha]_D^{25}$/(C, Solv.) |
|---|---|---|---|
| 20 | 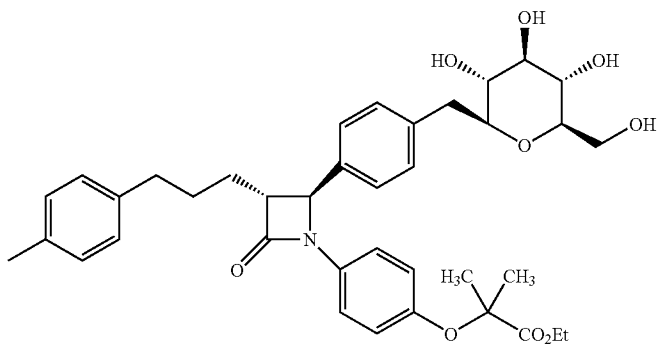 | 76–78 | |
| 21 | 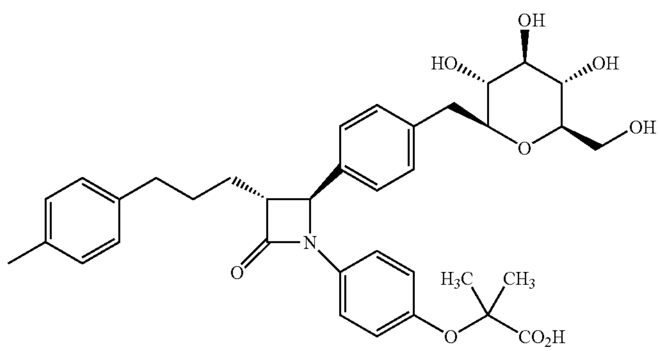 | 161–162 | |
| 22 | 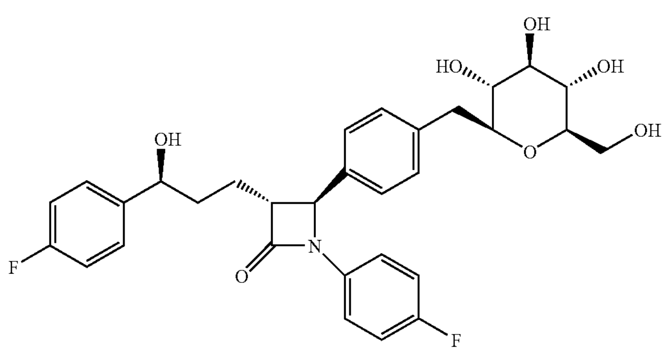 | 115–117 | −71.3 (C = 0.3, MeOH) |
| 23 | 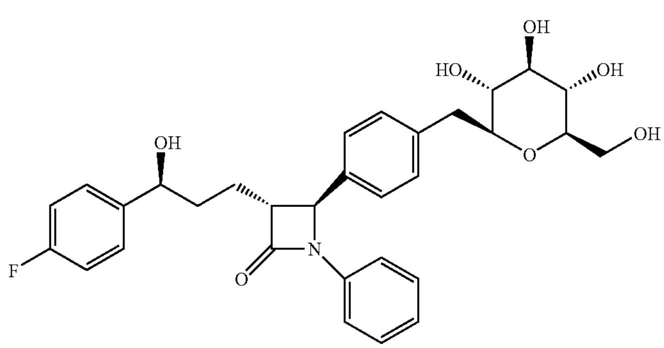 | 104–106 | −110 (C = 0.5, MeOH) |

-continued

| No. | Structure | mp (° C.) | $[\alpha]_D^{25}$/(C, Solv.) |
|---|---|---|---|
| 24 | 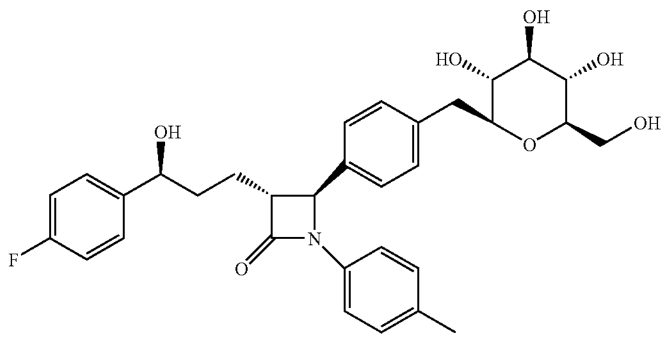 | 102–104 | −58.0 (C = 0.3, MeOH) |
| 25 | 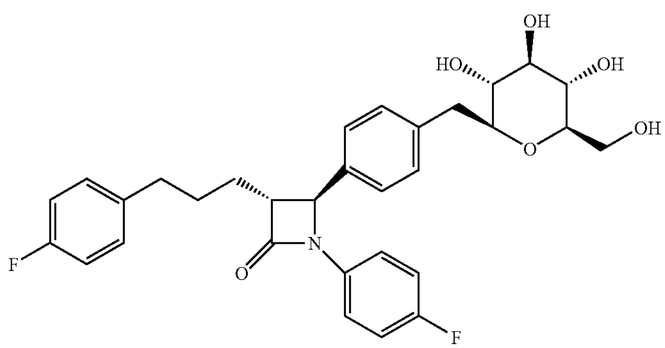 | 67–69 | −62.8 (C = 0.5, MeOH) |
| 26 | 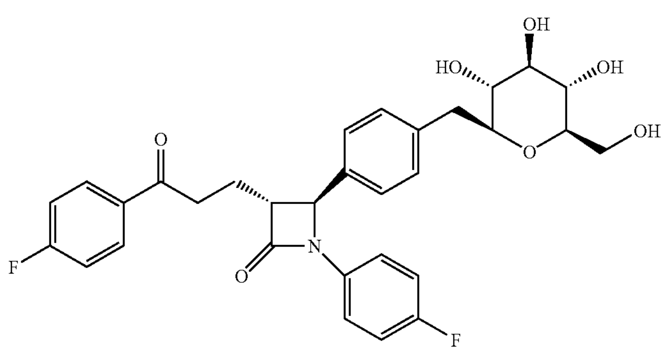 | 78–80 | −67.2 (C = 0.5, MeOH) |
| 27 | 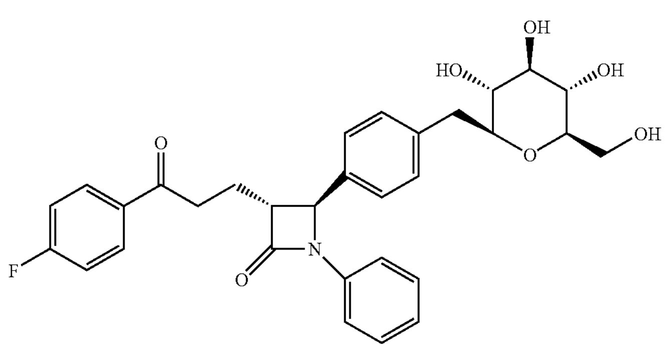 | 104–106 | −26.0 (C = 0.5, MeOH) |

-continued

| No. | Structure | mp (° C.) | $[\alpha]_D^{25}$/(C, Solv.) |
|---|---|---|---|
| 28 | 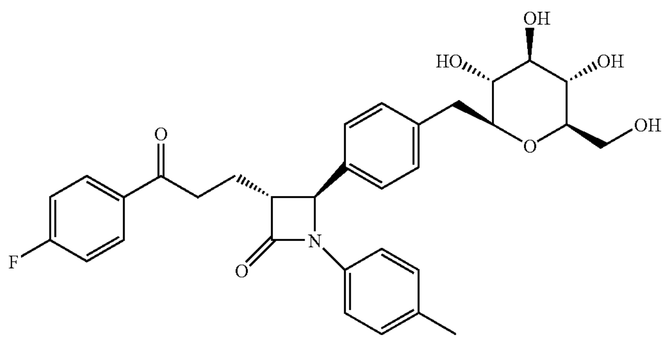 | 86–88 | −35.7 (C = 0.6, MeOH) |
| 29 | 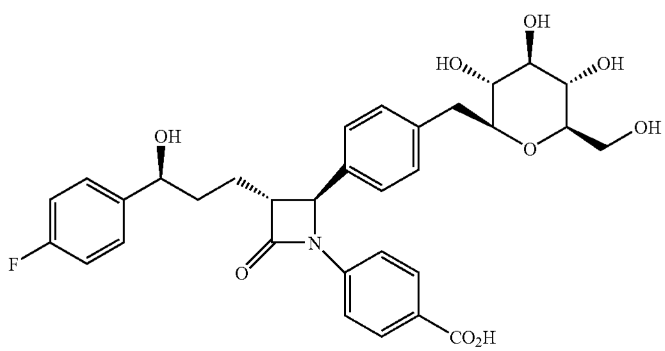 | 148–150 | −122.0 (C = 0.3, MeOH) |
| 30 | 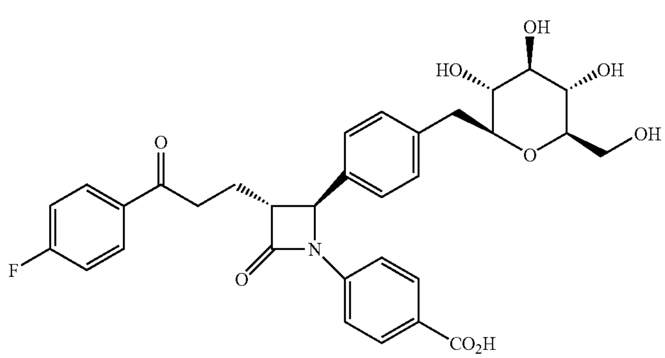 | 102–104 | −52.0 (C = 0.3, MeOH) |
| 31 | 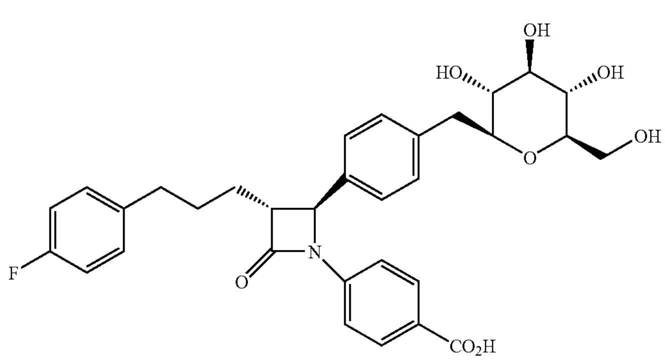 | 97–99 | |

-continued

| No. | Structure | mp (° C.) | $[\alpha]_D^{25}$/(C, Solv.) |
|---|---|---|---|
| 32 | 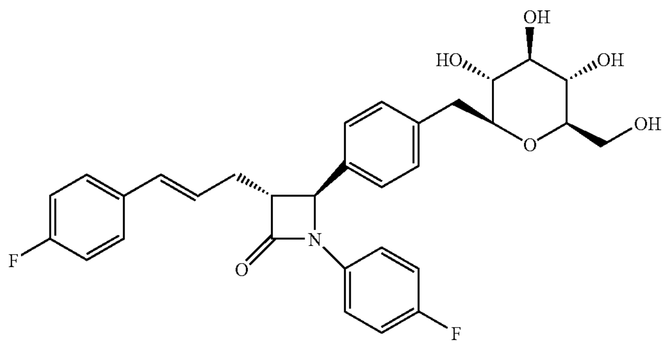 | liq | −39.3 (C = 0.8, MeOH) |
| 33 | 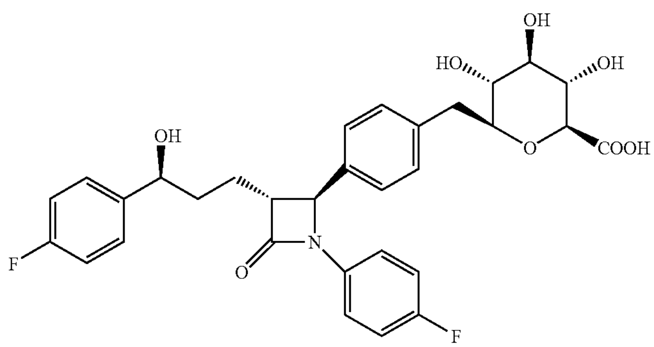 | 82–84 | −47.6 (C = 0.5, MeOH) |
| 34 | 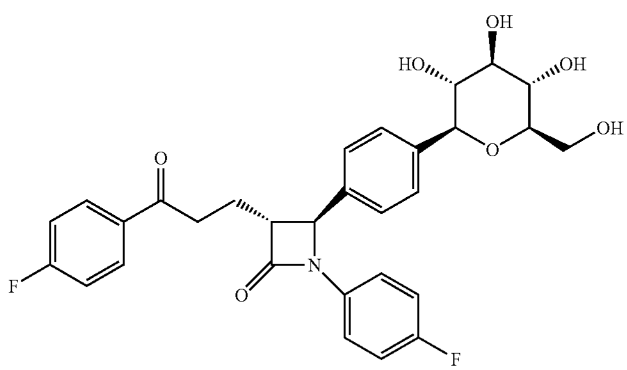 | 83–85 | |
| 35 | 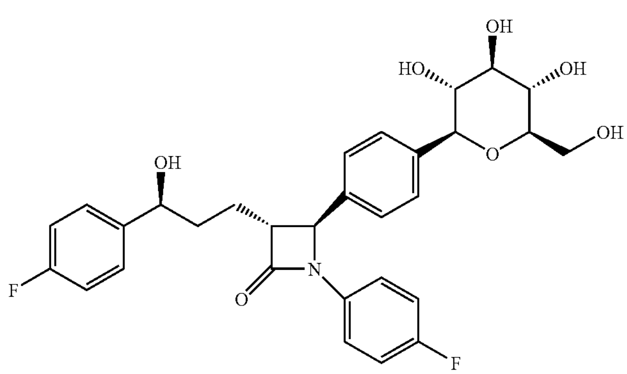 | 81–83 | |

-continued

| No. | Structure | mp (° C.) | $[\alpha]_D^{25}$/(C, Solv.) |
|---|---|---|---|
| 36 | 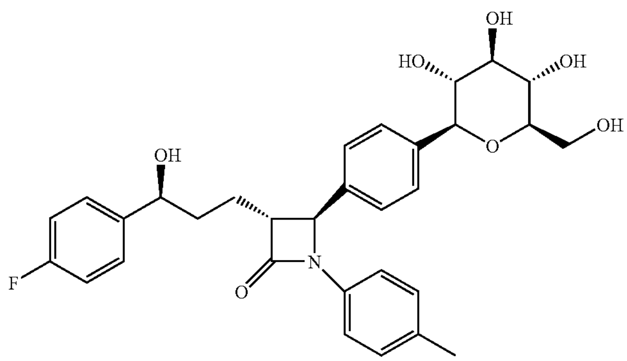 | 79–81 | |
| 37 | 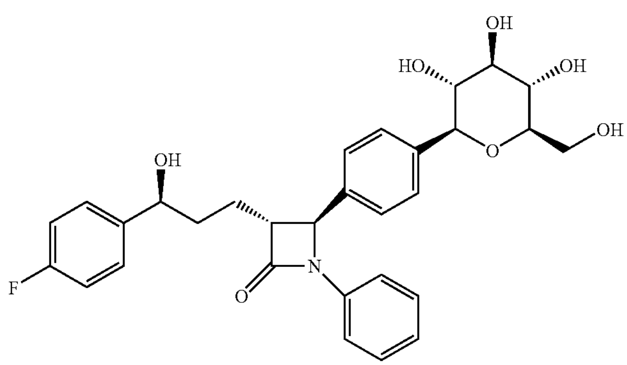 | 80–82 | |
| 38 | 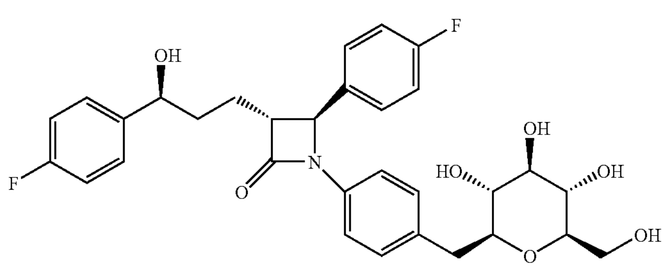 | 200–201 | −69.3 (C = 0.3, MeOH) |
| 39 | 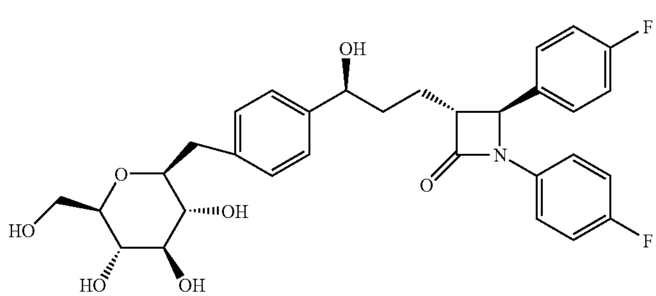 | 126–128 | −42.66 (C = 0.3, MeOH) |

| No. | Structure | mp (° C.) | $[\alpha]_D^{25}$/(C, Solv.) |
|---|---|---|---|
| 40 | 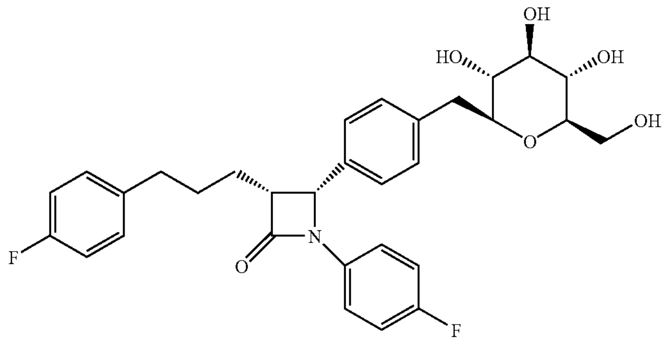 | 78–80 | |
| 41 | 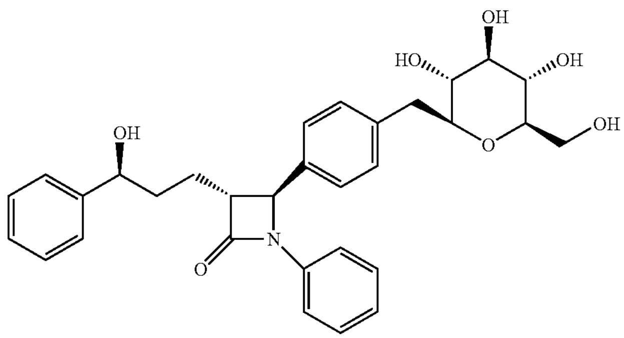 | 110–112 | −67.2 (C = 0.5, MeOH) |
| 42 | 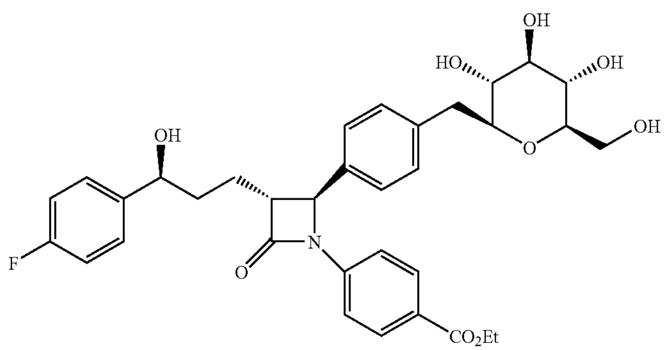 | 56–58 | −92.0 (C = 0.3, MeOH) |
| 43 | 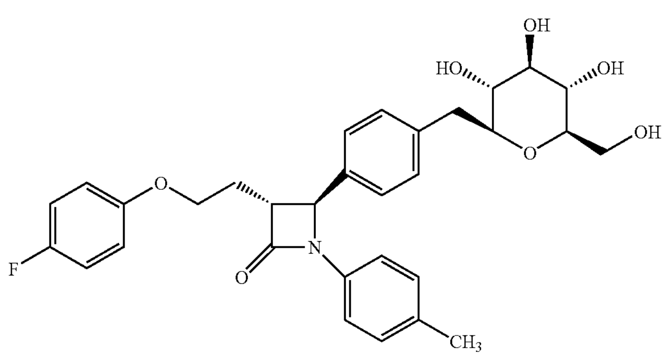 | 96–98 | −40.4 (C = 0.5, CHCl₃) |

-continued

| No. | Structure | mp (° C.) | $[\alpha]_D^{25}$/(C, Solv.) |
|---|---|---|---|
| 44 | 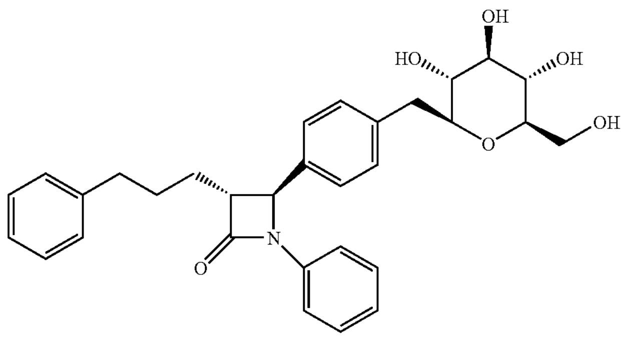 | 84–86 | −41.3 (C = 0.3, MeOH) |
| 45 | 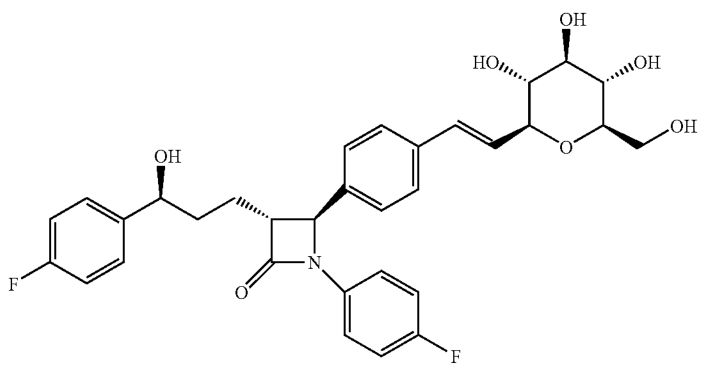 | 84–86 | −64.0 (C = 0.25, MeOH) |
| 46 | 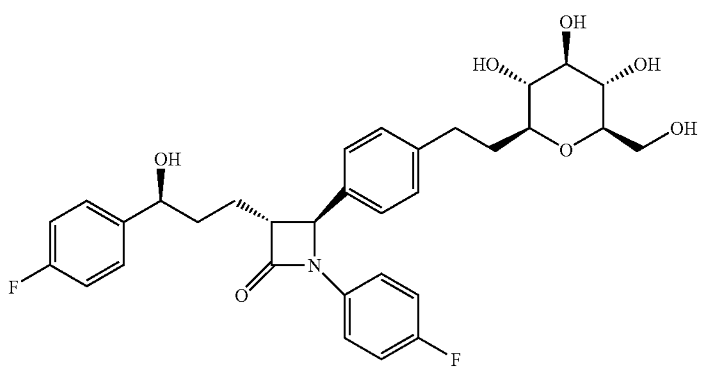 | 153–155 | −54.66 (C = 0.25, MeOH) |
| 47 | 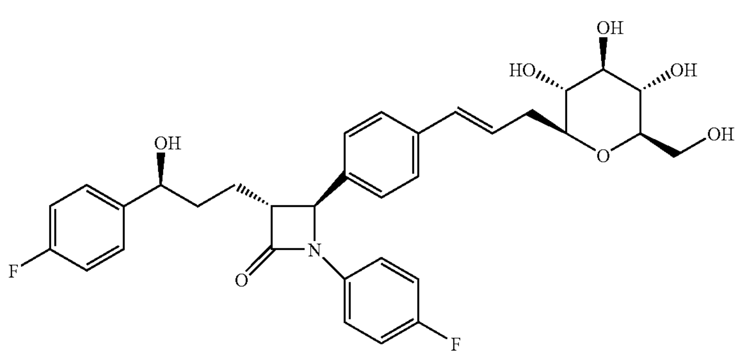 | 72–74 | −33.6 (C = 1.0, MeOH) |

| No. | Structure | mp (° C.) | $[\alpha]_D^{25}$/(C, Solv.) |
| --- | --- | --- | --- |
| 48 | 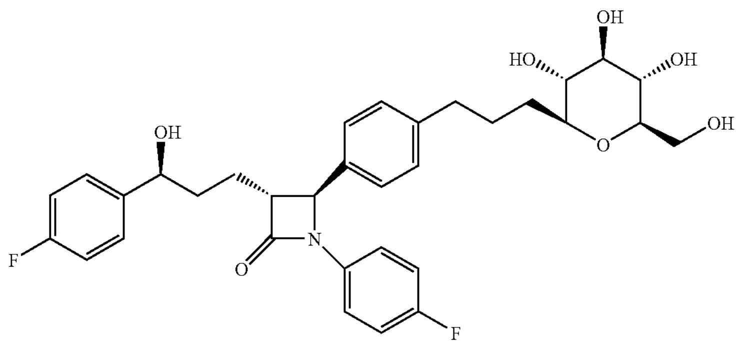 | 81–83 | −21.8 (C = 1.0, MeOH) |
| 49 | 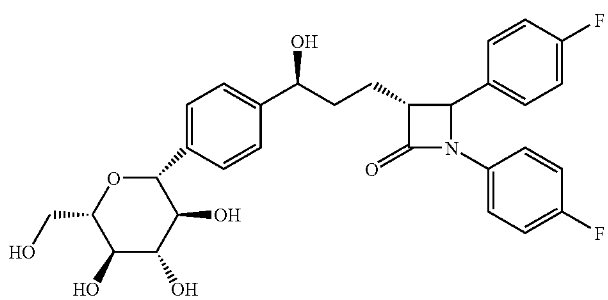 | 111–113 | −20.0 (C = 0.35, MeOH) |
| 50 | 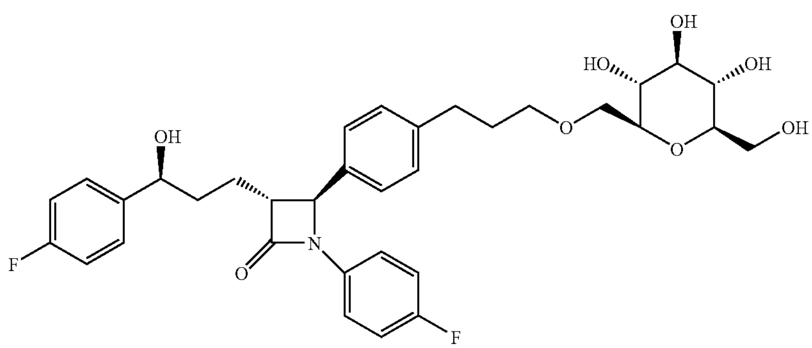 | 61–63 | −48.6 (C = 0.14, MeOH) |
| 51 | 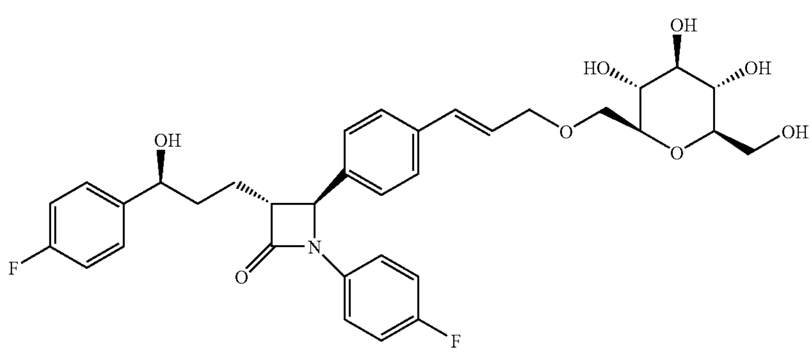 | 65–67 | −42.8 (C = 0.25, MeOH) |

| No. | Structure | mp (° C.) | [α]$_D^{25}$/(C, Solv.) |
|---|---|---|---|
| 52 | 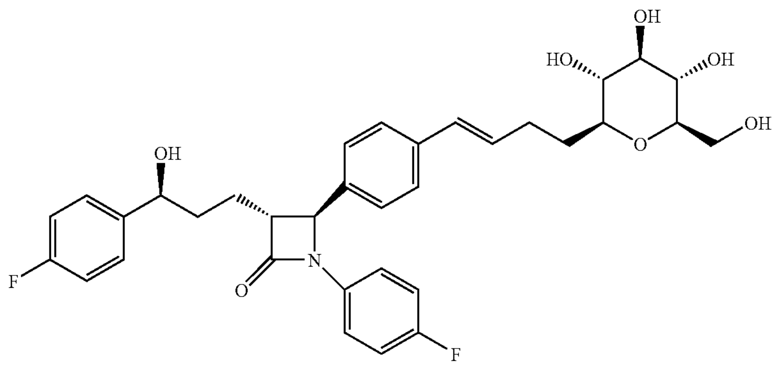 | 79–81 | −33.2 (C = 1.0, MeOH) |
| 53 | 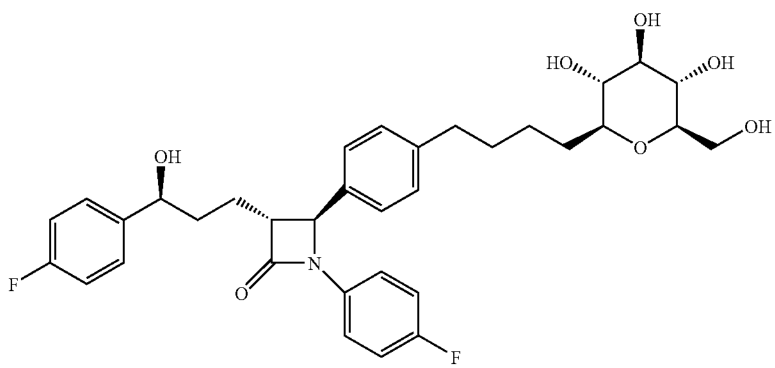 | 81–83 | −29.4 (C = 0.5, MeOH) |
| 54 | 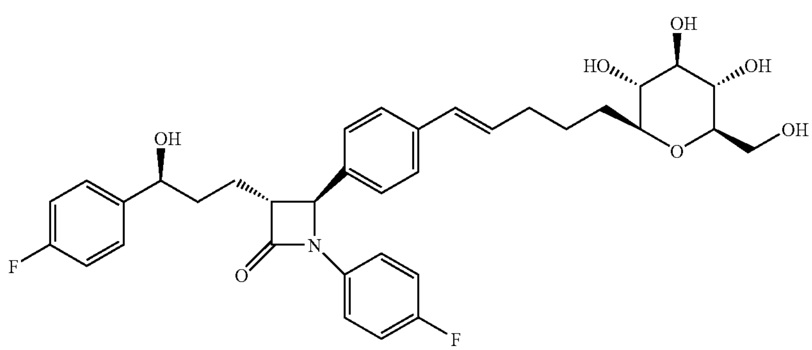 | 69–71 | −38.6 (C = 0.35, MeOH) |
| 55 | 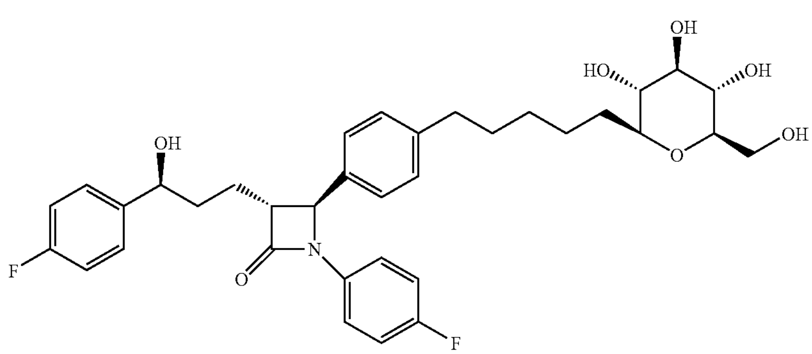 | 66–68 | −42.9 (C = 0.35, MeOH) |

| No. | Structure | mp (° C.) | $[\alpha]_D^{25}$/(C, Solv.) |
|---|---|---|---|
| 56 | 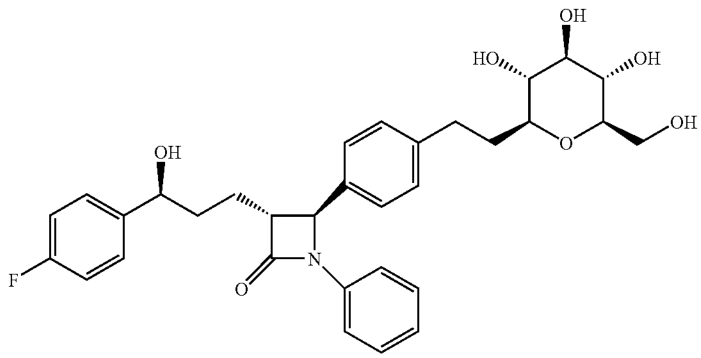 | 82–84 | −49.2 (C = 1.0, MeOH) |
| 57 | 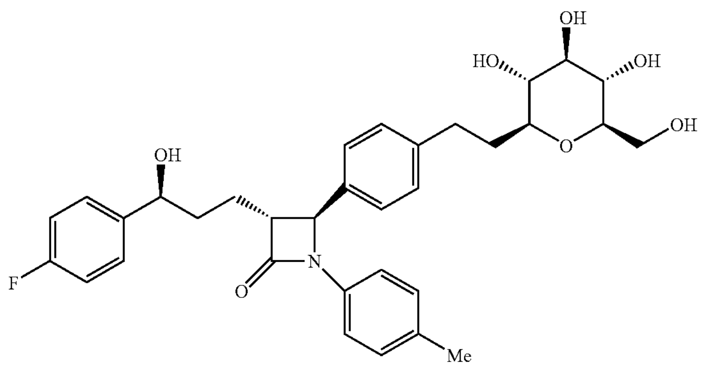 | 116–118 | −76.0 (C = 0.3, MeOH) |
| 58 | 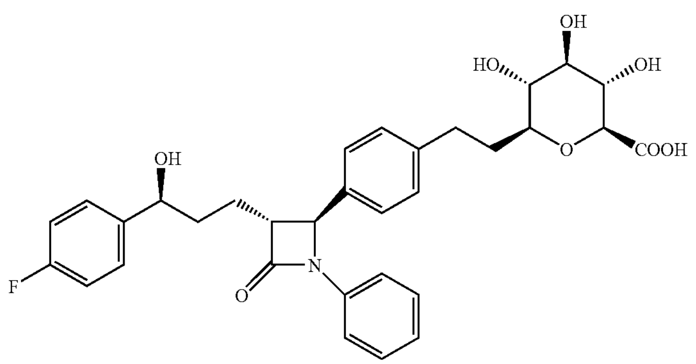 | 110–112 | −40.3 (C = 0.7, MeOH) |

Method 1

(1) (a) In case of $R_4$ is —CH$_2$— in the compounds of general formula (I), the compound is prepared by the following reactions.

The compound (1-2) obtained by a reaction of tetrabenzyl glucuronolactone (1-1) with Tebbe reagent (T. V. Rajanbabu et al., J. Org. Chem. 1986, 51, 5458), is used as a starting material. The compound (1-2) is subjected to Suzuki coupling reaction with the compound (1-3) (C. R. Johnsone et al., Synlett 1997, 1406) followed by desilylation to yield the compound (1-4).

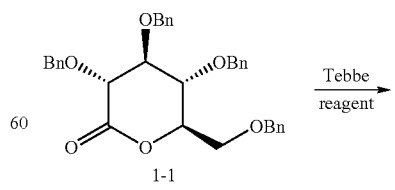

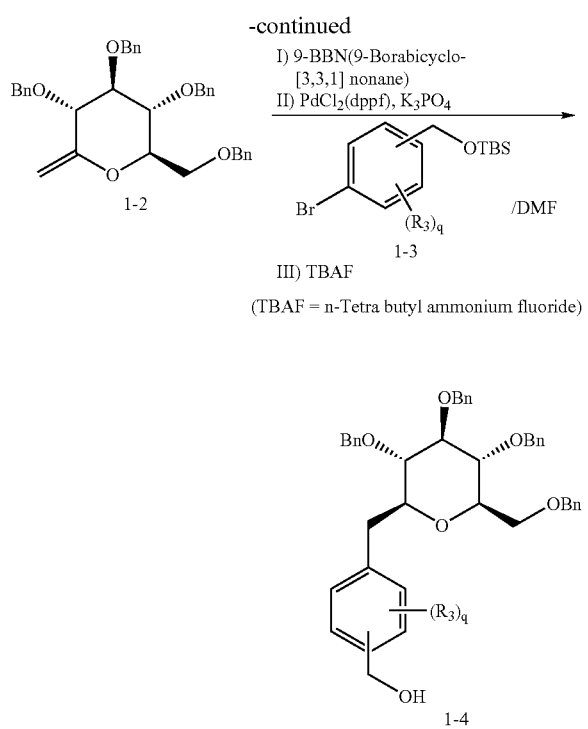

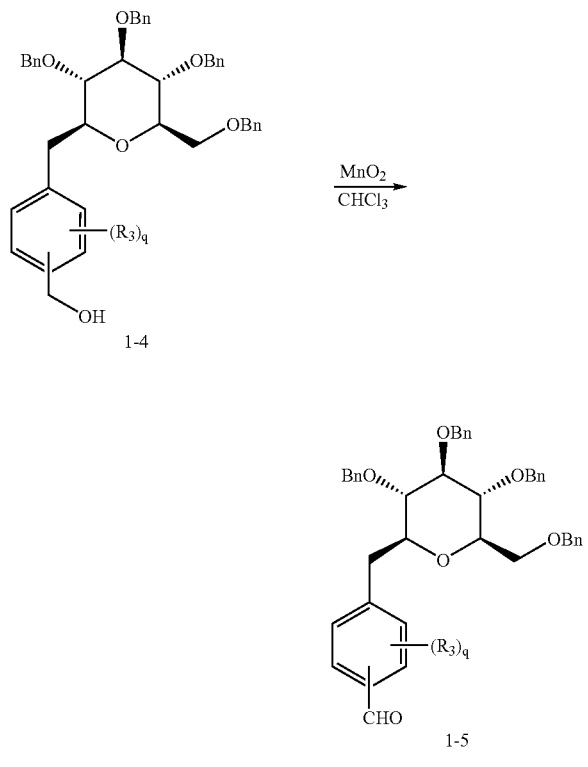

(b) The compound (1-5) is obtained by oxidation of the hydroxyl group of compound (1-4) to obtain the aldehyde compound (1-5).

(c) The aldehyde compound (1-5) and the amine compound (1-6) are condensed in the presence of a molecular sieves and p-toluenesulfonic acid to obtain the compound (1-7).

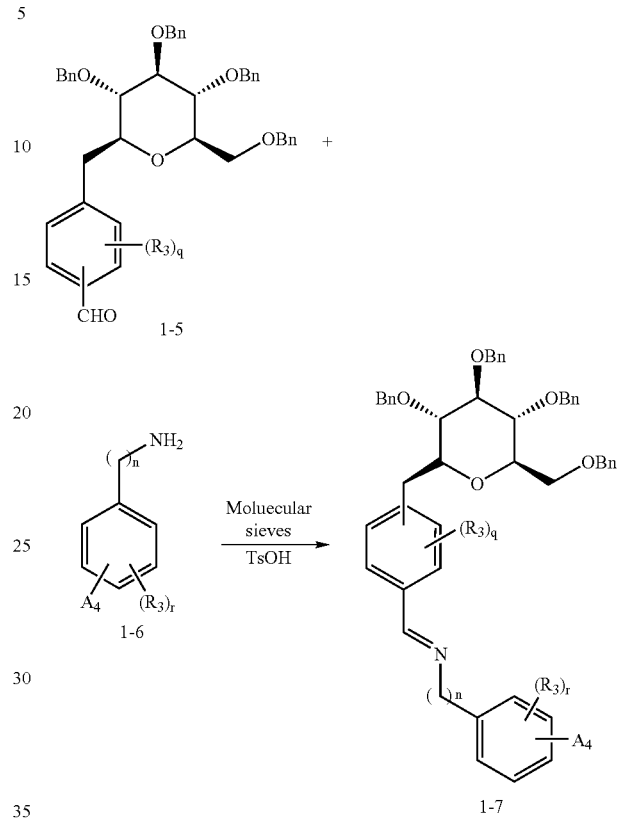

The imine compound (1-7) and the compound (1-8) are subjected to Staudinger reaction by refluxing in the presence of base to yield a β-lactam compound. In this reaction, when tri-n-butyl amine is used as the base, the trans β-lactam compound is obtained. When LDA (lithium diisopropyl amide) is used as the base, the cis β-lactam compound is obtained.

Furthermore, the asymmetric β-lactam compound can be also obtained by addition of a chiral ligand in the reaction mixture (A. M. Hafez et al., Org. Lett. 2000, 2(25), 3963–3965). Subsequently, the debenzylated compound (1-9) is obtained by catalytic hydrogenation.

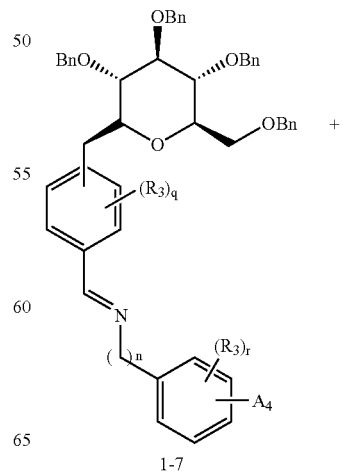

-continued

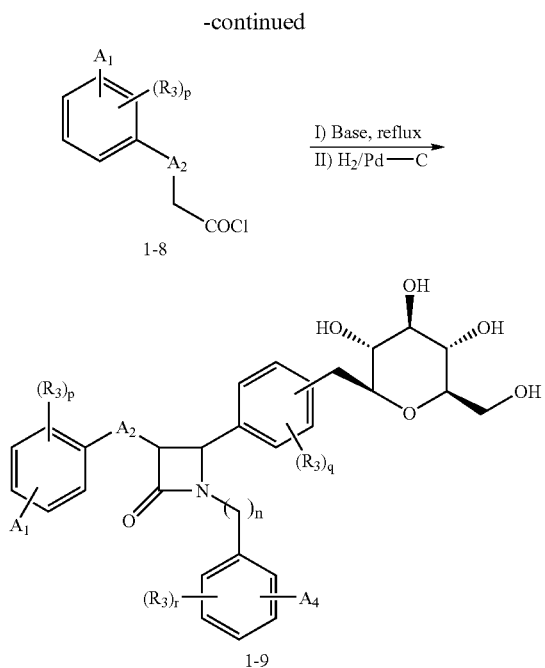

(d) The compound (1-10) is obtained by an acetylation of the compound (1-9).

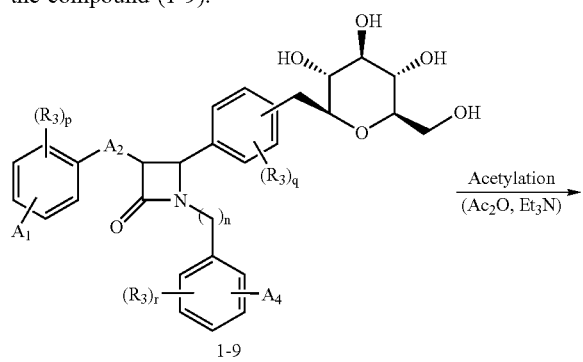

-continued

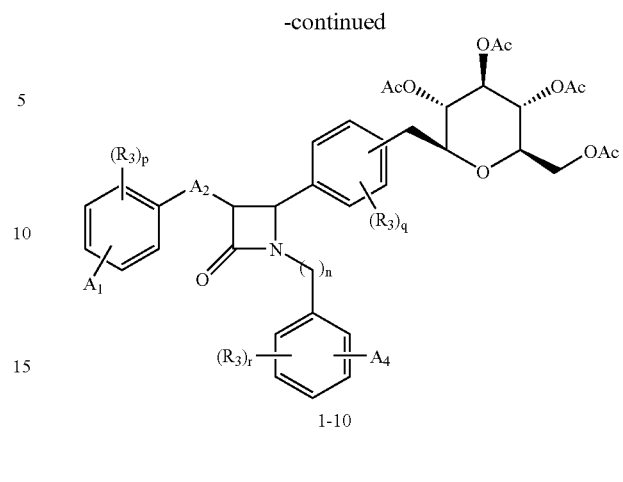

(2) In case of $R_4$ is —$CH_2$— in the compounds of general formula (I), the compound is prepared by the following reactions.

The compound (1-11) is reacted with Grignard reagent (1-12) to yield the compound (1-13) (M. F. Wong et al., J. Carbohydr. Chem. 1996, 15(6), 763; C. D. Hurd et al., J. Am. Chem. Soc. 1945, 67, 1972; H. Togo et al., Synthesis 1998, 409). Alternatively, the compound (1-11) is reacted with Grignard reagent (1-12) followed by dehydroxylation with triethylsilyl hydride. The generated hydroxyl group is converted to a leaving group such as tosyl group or halogen and the resulting compound is reacted with base to yield the olefin compound. Then the compound (1-13) is obtianed by hydrogenation of the olefin compound. The compound (1-13) is converted to Grignard reagent with magnesium metal and reacted with DMF (dimethylformamide) to yield the compound (1-14). The compound (1-15) is obtained by the reaction of Grignard reagent of the compound (1-13) with dry-ice ($CO_2$).

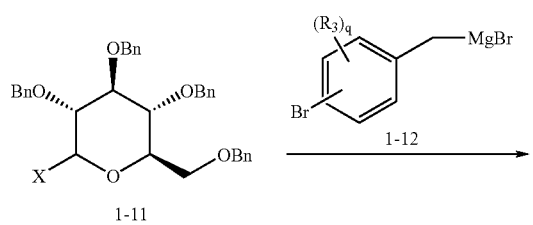

-continued

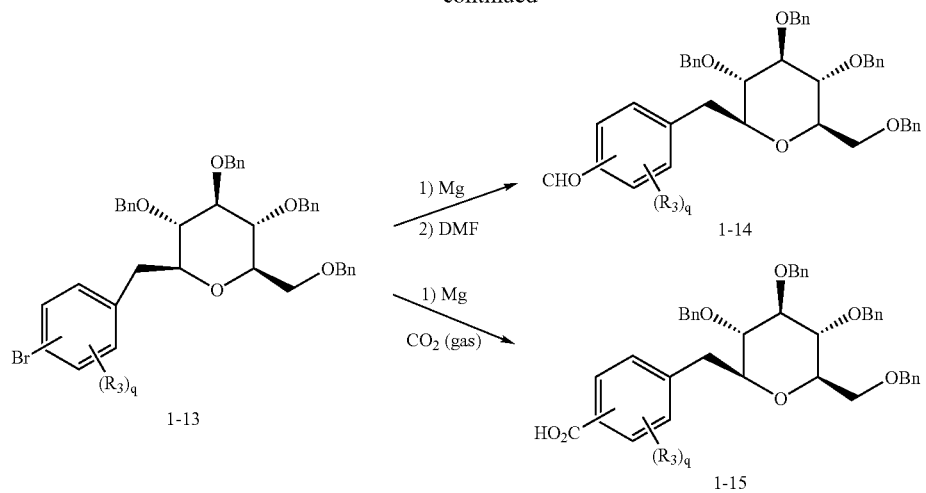

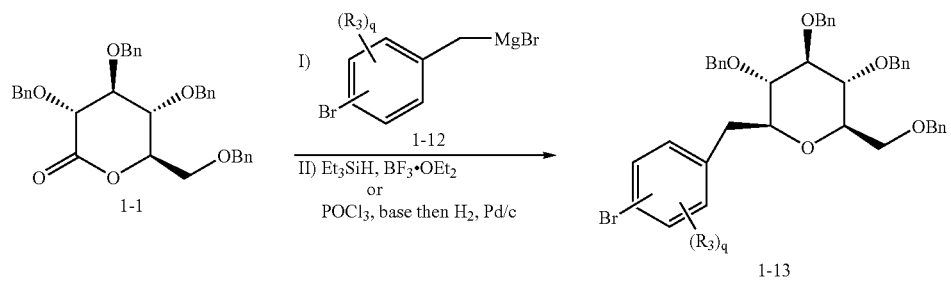

The compound (1-14) and the compound (1-15) which are obtained as above mentioned are the synthetic intermediates of the general formula (I) according to the Method 1-(1)-(c) and (d).

Method 2

(1) In case of $R_4$ is a directly connected bond in the compounds of general formula (I), the compound is prepared by the following reactions.

Tetrabenzylglucuronolactone (1-1) is reacted with the compound (2-1) followed by the reaction with $Et_3SiH$ and $BF_3.Et_2O$ to provide the compound (2-2) (J. M. Lancelin et al., Tetrahedron Lett. 1983, 24, 4833). The compound (2-2) is the synthetic intermediates of the general formula (I) according to the method 1-(1)-(b), (c), and (d).

-continued

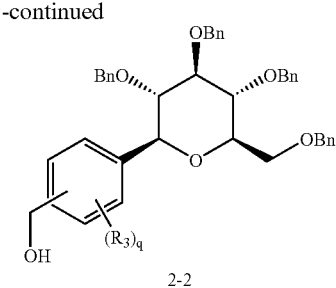

(2) In case of $R_4$ is a directly connected bond in the compounds of general formula (I), the compound is prepared by the following reactions.

The compound (2-4) is obtained by the reaction of the compound (1-11) with Grignard reagents (2-3) (F. Marquez et al., An. Quim., Ser. C. 1983, 79(3), 428).

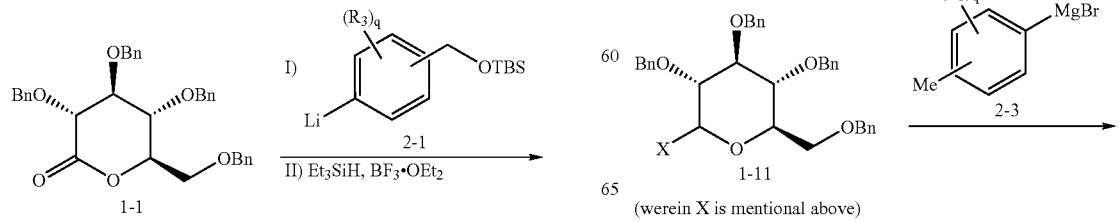

(werein X is mentional above)

-continued

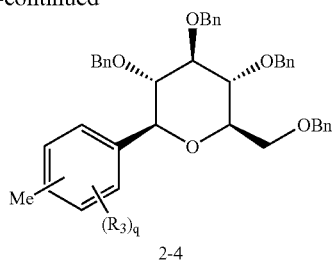

2-4

The compound (1-14) is obtained by conversion of the methyl group of the compound (2-4) to the aldehyde compound (P. S. Portoghese et al., J. Med. Chem. 2000, 43, 2489).

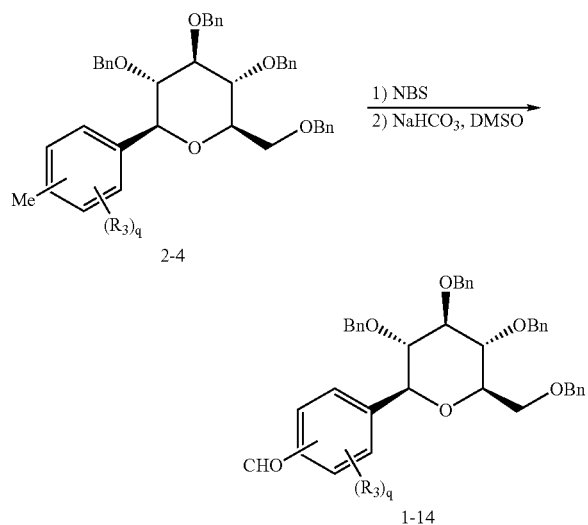

The compound (2-2) is obtained by reduction of the compound (1-14) with $NaBH_4$.

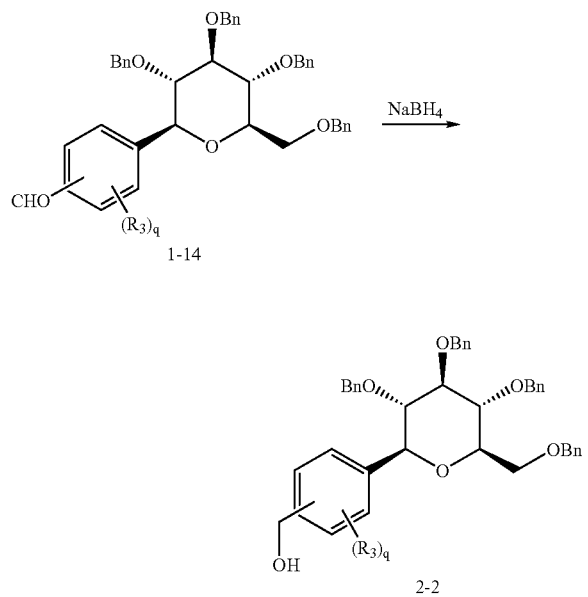

Method 3

(1) In case of $R_4$ is —$OCH_2$— in the compounds of general formula (I), the compound is prepared by the following reactions.

(a) The compound (3-1) prepared by the known method (D. Zhai et al., J. Am. Chem. Soc. 1988, 110, 2501.; P. Allevi et al., J. Carbohydr. Chem. 1993, 12(2), 209) is subjected to Mitsunobu reaction with the compound (3-2) to provide the compound (3-3).

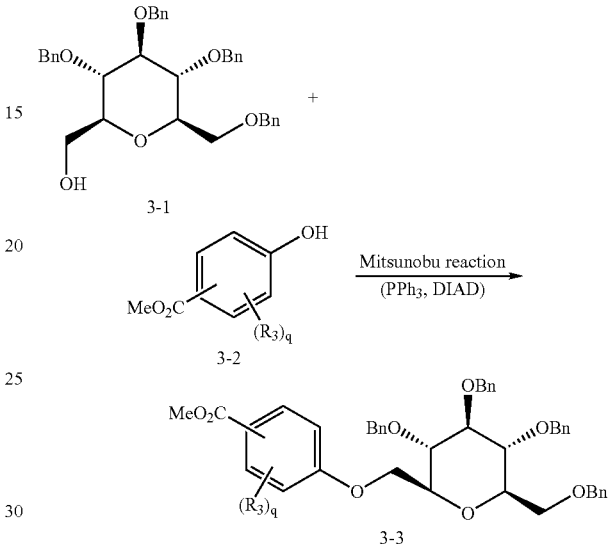

(b) The compound (3-4) is obtained by reduction of the methylester group of the compound (3-3) to the alcohol group with $LiAlH_4$.

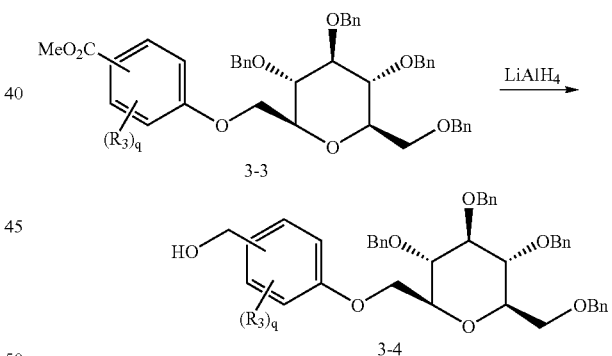

The compound (3-4) is the synthetic intermediates of the general formula (I) according to the method 1-(1)-(b), (c), and (d).

Method 4

In case of that one of $A_1$, $A_3$, and $A_4$ is the following compound in the compounds of general formula (I), the compound is prepared by the following reactions.

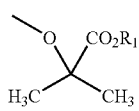

The compound (4-1) is reacted with 2-bromoisolactic acid alkylester (4-2) in the presence of $K_2CO_3$ followed by hydrogenation to yield the compound of general formula (I). Alternatively, the compound (4-3) is obtained by hydrolysis with lithium hydroxide and followed by the deprotection to provide the compound of general formula (I).

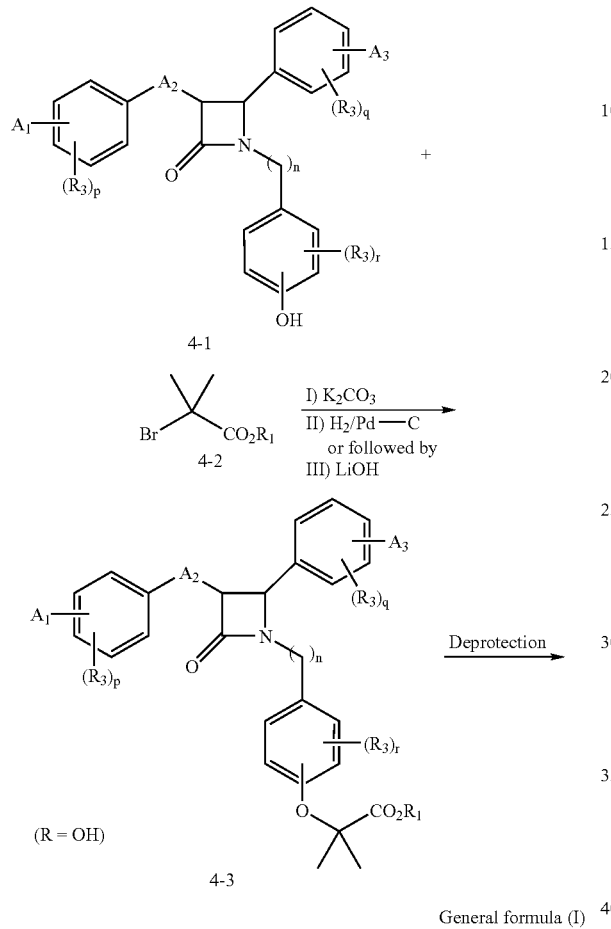

Method 5

In case of $R_2$ is —$CO_2H$ in the compounds of general formula (I), the compound is prepared by the following reactions.

The compound (5-1) is oxidazed with TEMPO (2,2,6,6-tetramethyl-1-piperidinyloxy, free radical) to yield the compound (5-2).

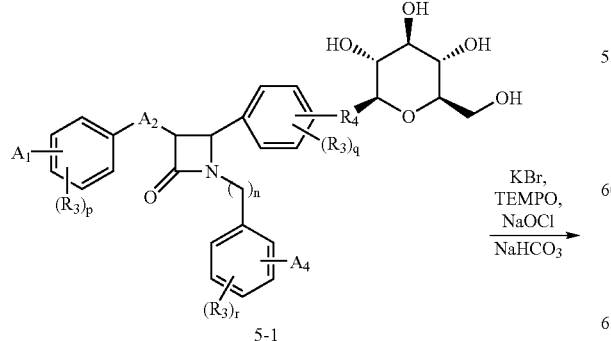

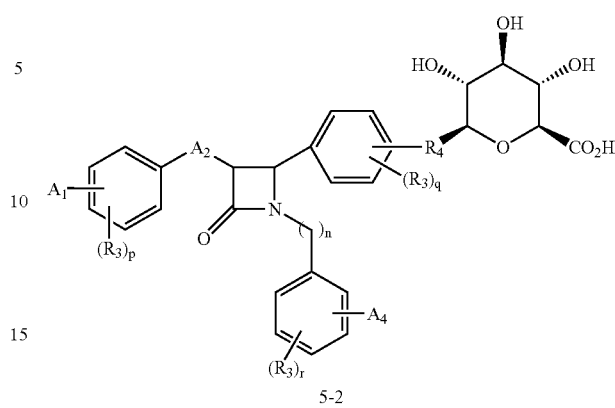

Method 6

The compound (6-3) is obtained by the reaction of the compound (6-1) and (6-2). The compound (6-3) is oxidazed to the sulfone compound followed by Ramberg-Bäcklund reaction (P. S. Belica et. al., Tetrahedron Lett. 1998, 39, 8225.; F. K. Griffin et al., Tetrahedron Lett. 1998, 39, 8179) to afford the compound (6-4). The compound (6-4) is hydrogenated followed by a reaction with TBAF to provide the compound (1-4). The compound (1-4) can be used as synthetic materials to obtain general formula (I) according to the method 1.

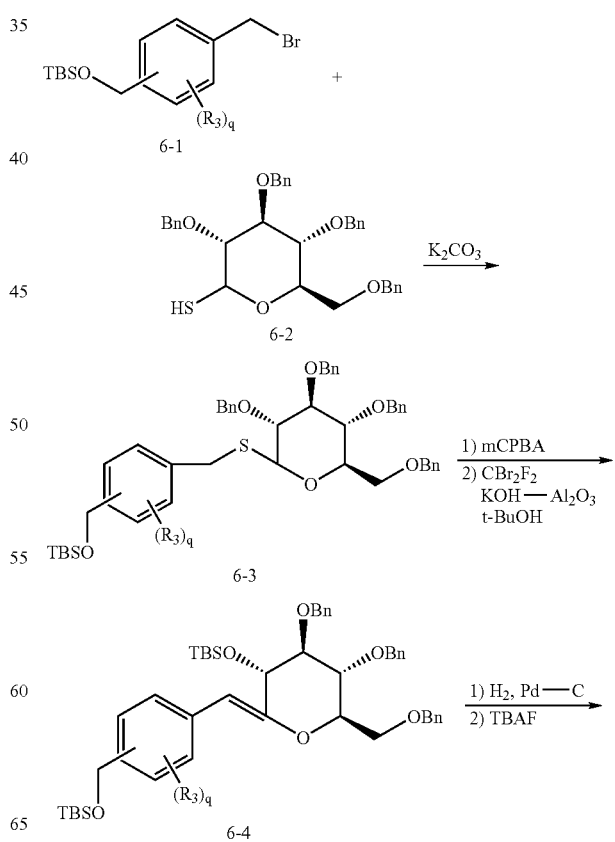

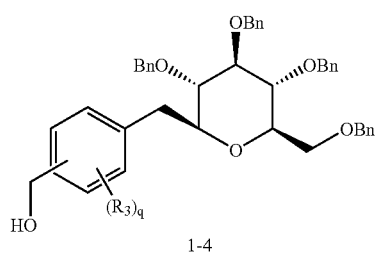

1-4

Method 7

(1) In case of $R_3$ is —OH— and —OC(O)$R_1$ in the compounds of general formula (I), the compounds are prepared by the following reactions.

The compound (7-3) is obtained by glycosidation of the compound (7-1) with the compound (1-11) in the presence of Lewis acid (BF$_3$.Et$_2$O, SnCl$_4$, AgOTf-Cp$_2$HfCl$_2$, etc) (R. R. Schmidt et al., Synthesis 1993, 325). The reaction proceed in 2 steps, first step is O-glycosidation and second step is O-glycoside rearrengment to C-glycoside. Futhermore, the compound (7-3) can be converted to the compound (7-4) by esterification of the phenolic hydroxyl group. The compound (7-3) and (7-4) can be used as the synthetic materials to obtain general formula (I) according to the method 1 and 3.

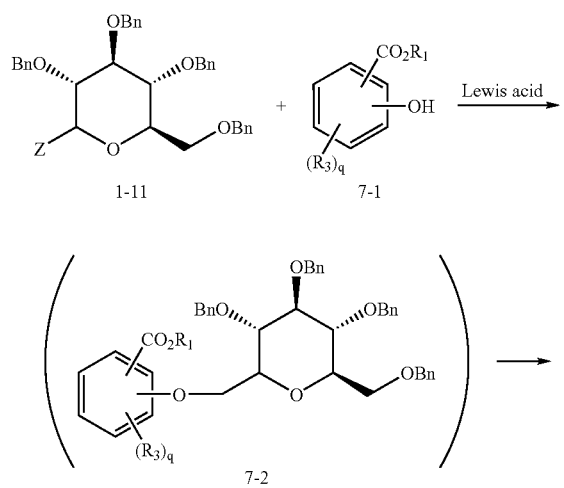

(2) In case of $R_3$ is —OH— and —OC(O)$R_1$ in the compounds of general formula (I), the compounds are prepared by the following reactions.

The compound (7-6) obtained by the same procedure of method 7-(1) is deprotected to obtain the compound (7-7). One of the hydroxyl group of the compound is triflated, followed by a reaction of carbone monooxide to give the compound (7-3) (R. E. Dolle et al, Chem. Commun. 1987, 904). The compound (7-3) is used as the starting material of general formula (I) according to the method 7-(1), 1 and 3.

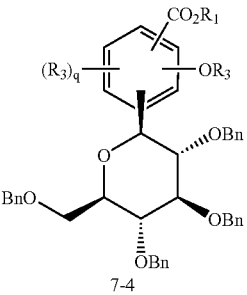

7-4

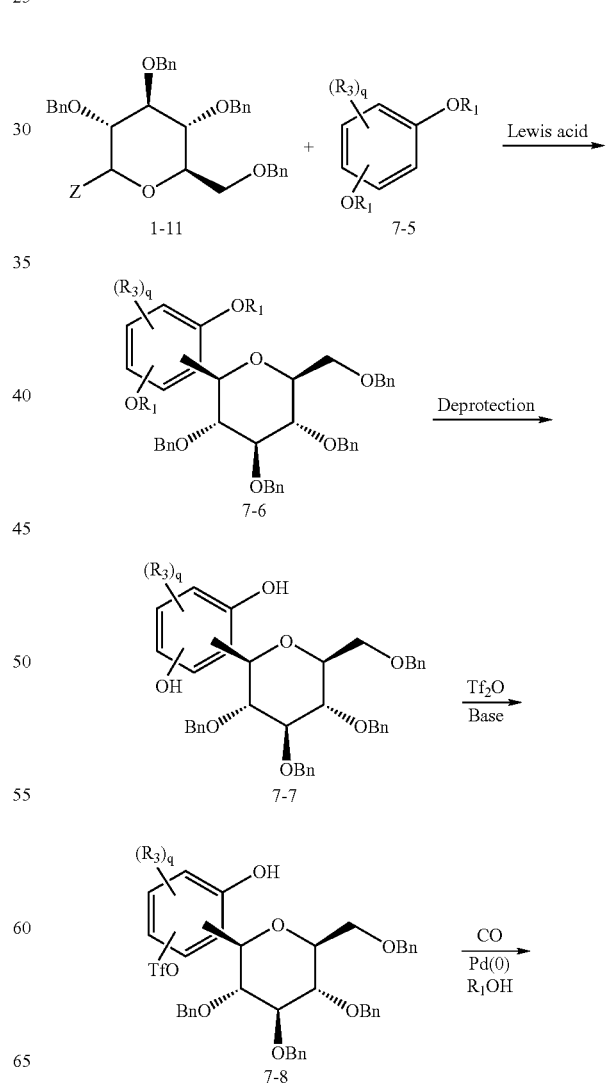

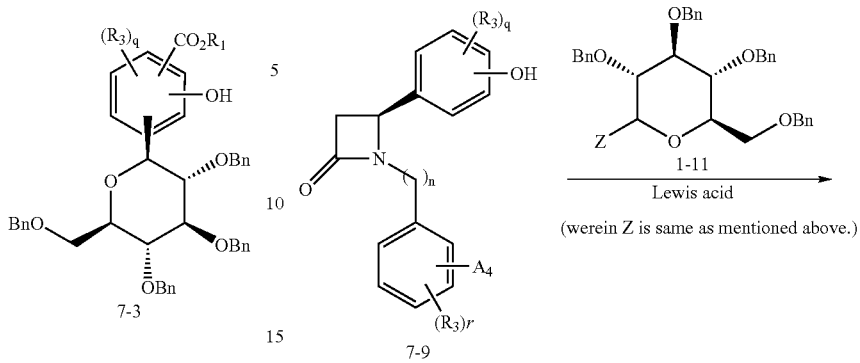

The compound (7-3) is also obtained by the same coupling reaction of the compound (7-11) with the compound (1-11) to obtain the compound (7-12) followed by Haloform reaction of the acetyl group to obtain the compound (7-3) (S. Kajigaeshi et al., Synthesis 1985, 674).

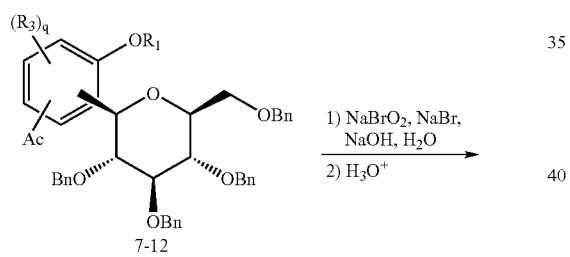

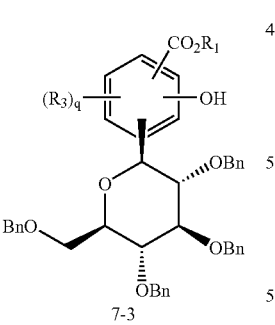

(3) In case of $R_3$ is —OH— and —OC(O)$R_1$ in the compounds of general formula (I), the compounds are prepared by the following reaction.

The compound (7-10) is obtained by the aryl C-glycosidation of the compound (7-9) according to the method 7 (1). The compound (7-10) is used as a starting material of general formula (I) according to the method 8.

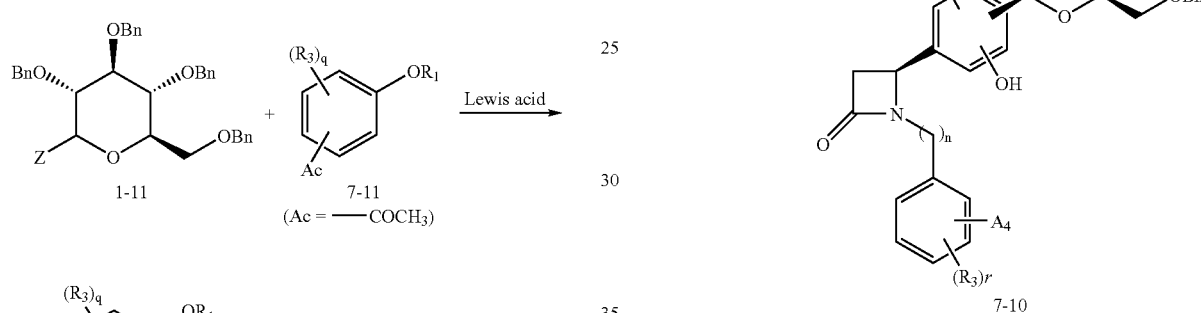

Method 8

The preparative methods of the optically active compounds (I).

(a) Benzylation of the hydroxy group of D-p-hydroxyphenylglycine (8-1) provides the compound (8-2) using E. Wunsch's method (Chem. Ber. 1958, 91, 543).

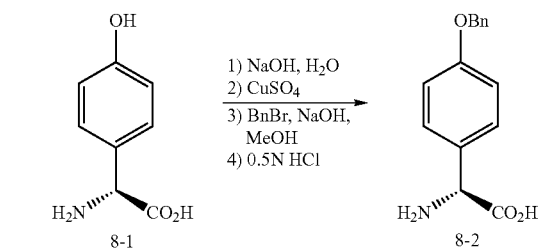

The compound (8-3) is obtained by the protection of the amino group of the compound (8-2) with Boc group.

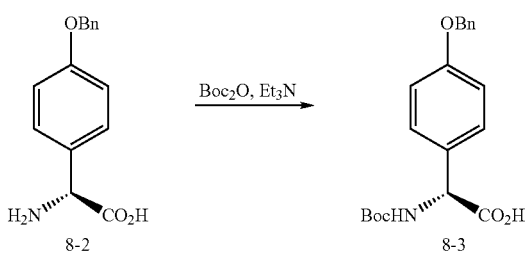

The compound (8-3) is converted to the compound (8-4) by homologation (W. W. Ogilvie et al., Bioorg. Med. Chem. 1999, 7, 1521). Then, the compound (8-5) is obtained by deprotection of the Boc group of the compound (84).

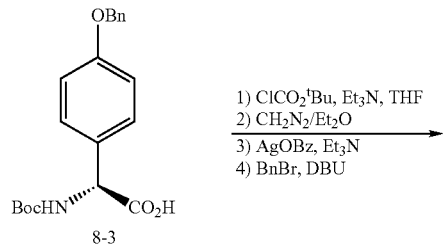

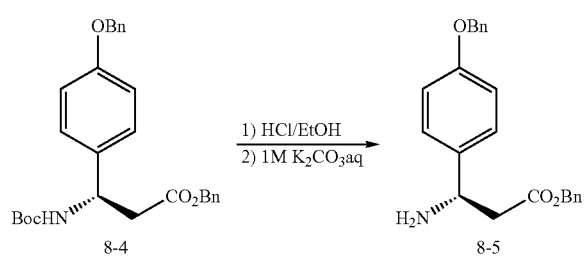

Cyclization of the compound (8-5) provides the β-lactam (8-6) using W. W. Ogilvie's method (W. W. Obilvie et al., Bioorg. Med. Chem. 1999, 7, 1521).

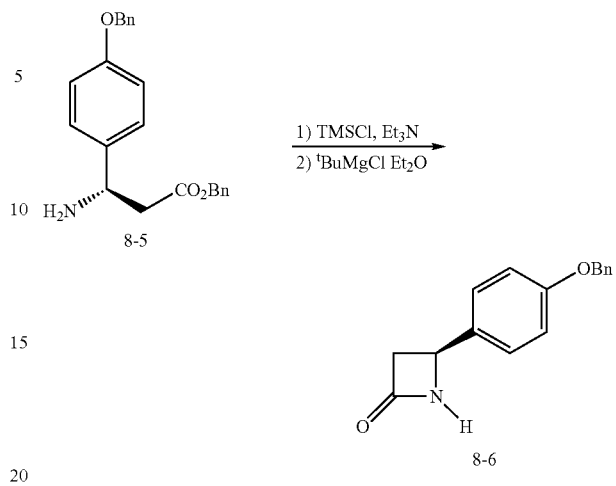

The compound (8-5) is also obtained by following method as the optically active compound.

Namely, the compound (8-9) is obtained by the reaction of the compound (8-7) with the optically active amino acid derivatives (8-8) in the presence of acid catalyst. The compound (8-9) is directly reduced to the compound (8-11). The compound (8-11) is also obtianed by a reduction of olefin (ex. NaHB(OAc)$_3$, NaBH$_4$) and treated with strong acid (ex. HCO$_2$H, Et$_3$SiH) (C. Cimarell et al., J. Org. Chem. 1996, 61, 5557) or hydrogenolysis. The compound (8-11) provides the compound (8-5) by an ester exchange reaction with BnOH. The compound (8-5) can be converted to the compound (8-6) by the same method as above mentioned.

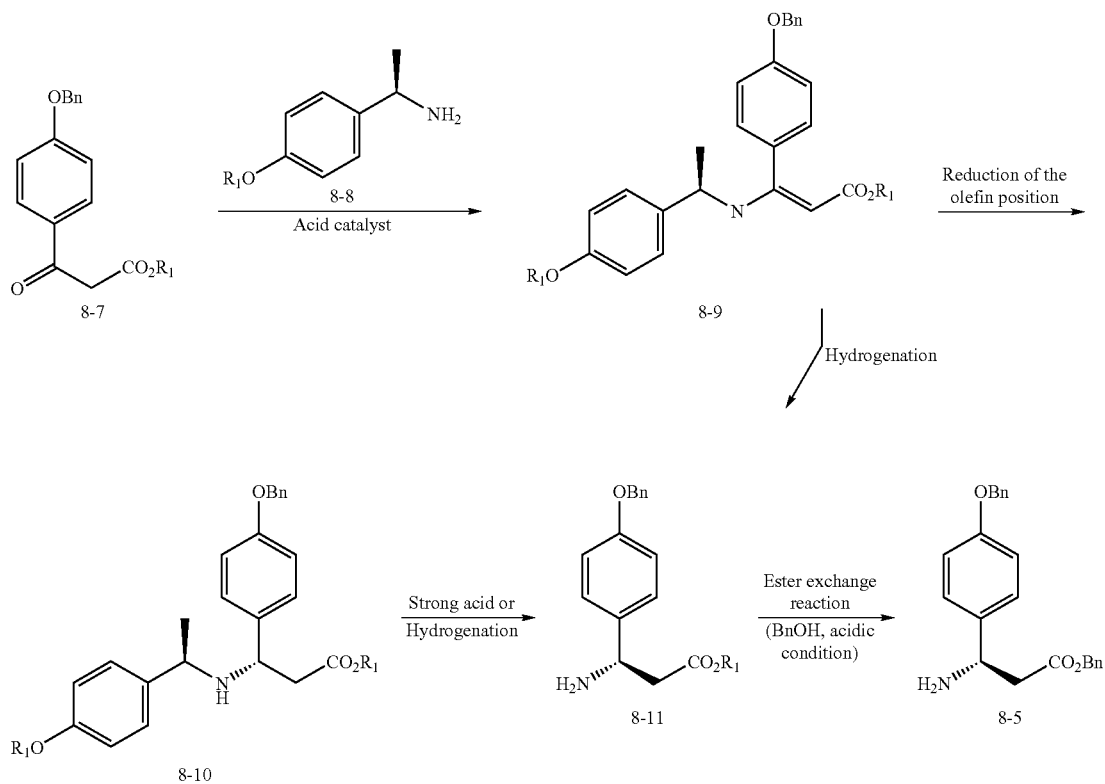

The β-lactam compound (8-6) is N-alkylated by D. M. T. Chan's method (Tetrahedron Lett. 1998, 39, 2933), followed by debenzylation to afford the compound (8-12).

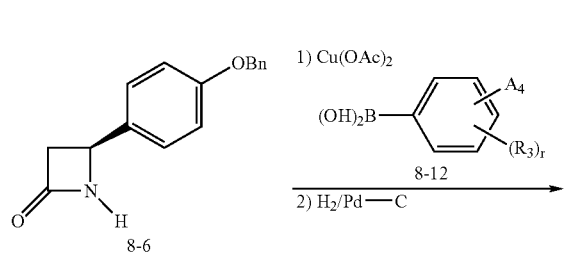

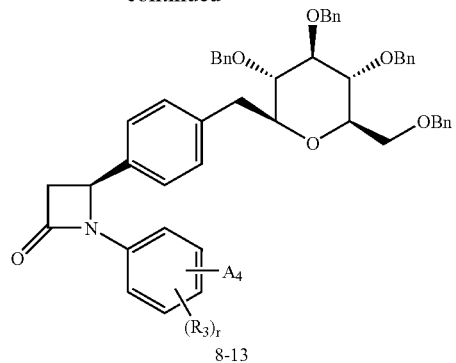

The compound (8-13) is obtained by Suzuki coupling reaction of the compound (8-12) and the glucose derivatives (1-2) according to C. R. Johnson's method (C. R. Johnson et al., synlett 1997, 1406).

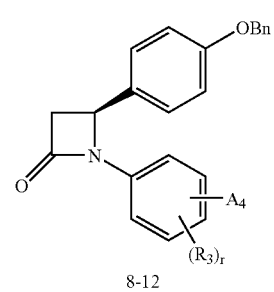

The compound (8-13) is reacted with LDA, followed by C-alkylation with methyl acrylate to provide the compound (8-14).

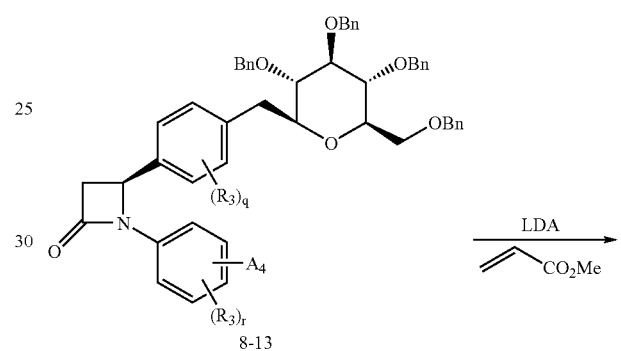

The convention of ester group of the compound (8-14) to the acid chloride, and coupling with the compound (8-15) using Negishi's method and obtained the compound (8-16).

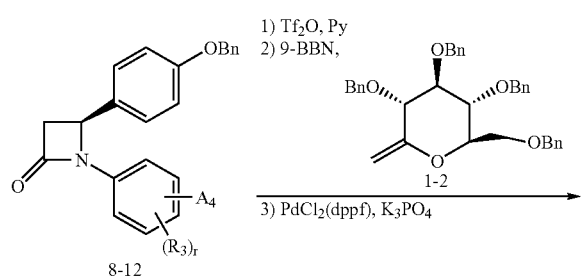

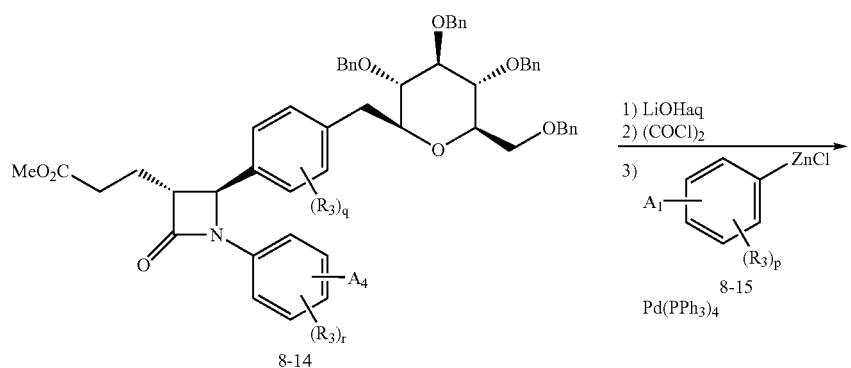

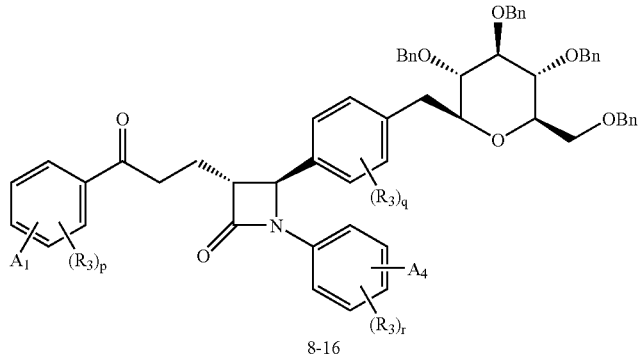
8-16
The compound (8-16) is debenzylated to the compound (8-17) and followed by asymmetric reduction of the ketone group of the compound (8-17) by E. J. Corey's method (E. J. Corey et al., J. Am. Chem. Soc. 1987, 109, 7925).
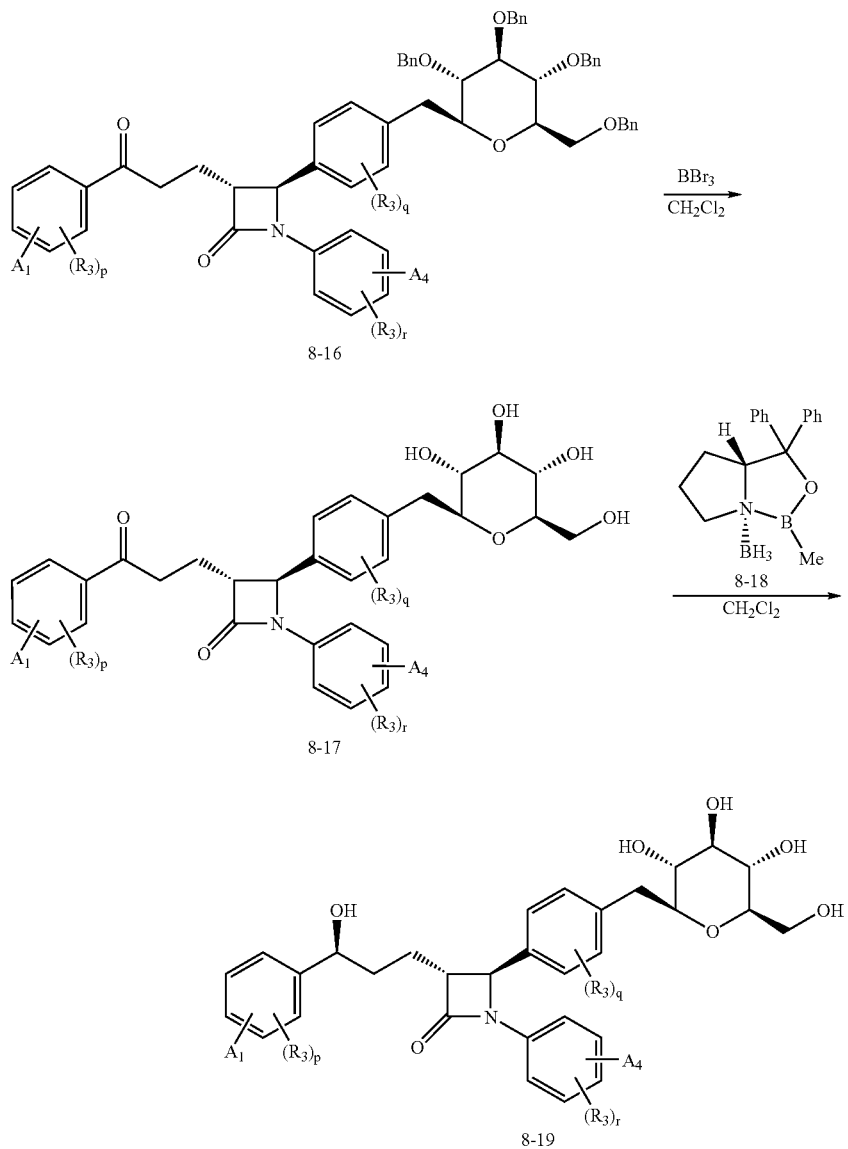

(b) The compound (8-13) is reacted with LDA, followed by the reaction with the compound (8-20) to provide the compound (8-21). The compound (8-22) is obtained by hydrogenation of the compound (8-21).
for example, according to the method 8, the compound 39 is prepared from the following compound (8-23) which correspond to the compound (8-15).
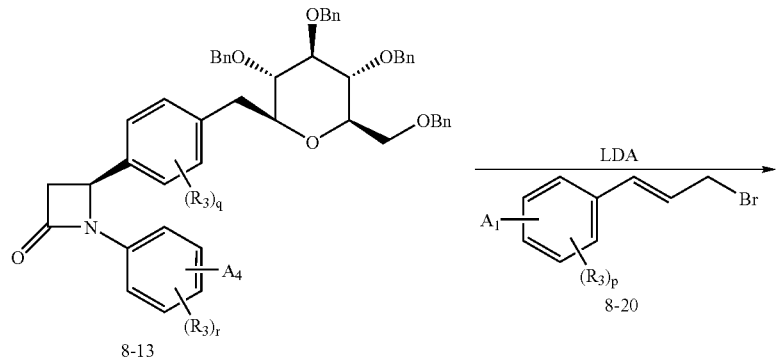
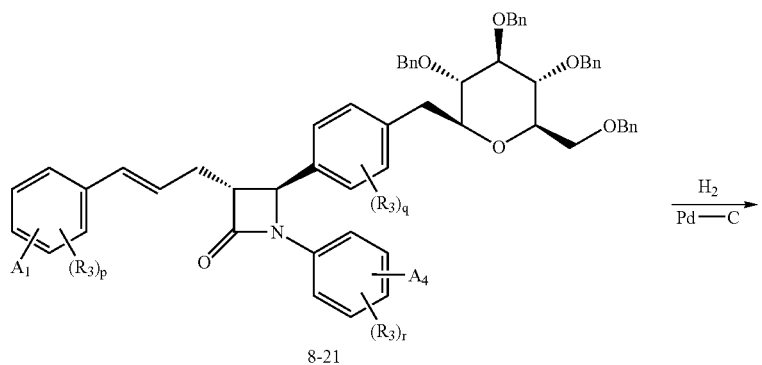
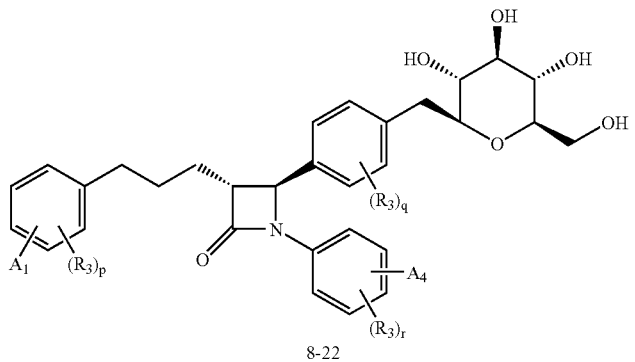
In case of $A_1$ in the general formula (I) is the following compound,
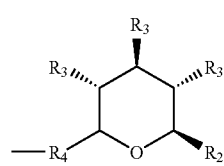
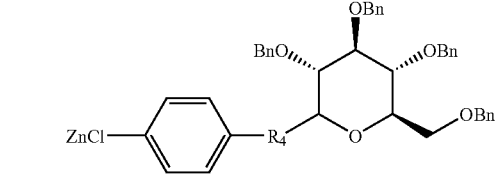

In case of $A_4$ in the general formula (I) is the following compound,

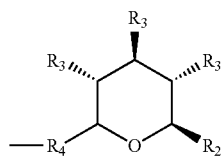

for example, according to the method 8, the compound 38 is prepared from the following compound (8-24) which correspond to the compound (8-12).

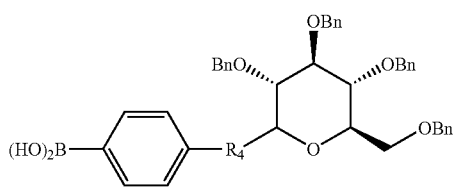

8-24

The compound (8-25) is also obtained by enzymatic separation of a racemic compound (S. J. Faulconbridge et al., Tetrahedron Lett., 2000, 41, 2679). The compound (8-25) can be converted to general formula (2) by Suzuki coupling as above mentioned.

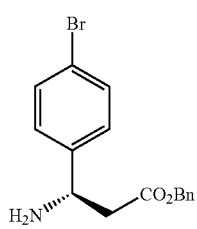

8-25

Method 9

The preparative method of the optically active compounds (II).

The compound (9-1) is condenced with the compound (9-2) to provide the compound (9-3) by K. Tomioka's method (K. Tomioka et al., J. Chem. Soc., Chem. Commun. 1999, 715). The compound of general formula (I) is obtained by deprotection of the compound (9-3). The compound (9-3) is also obtained by the reaction of the silyl enol ether with Lewis acid instead of the compound (9-1).

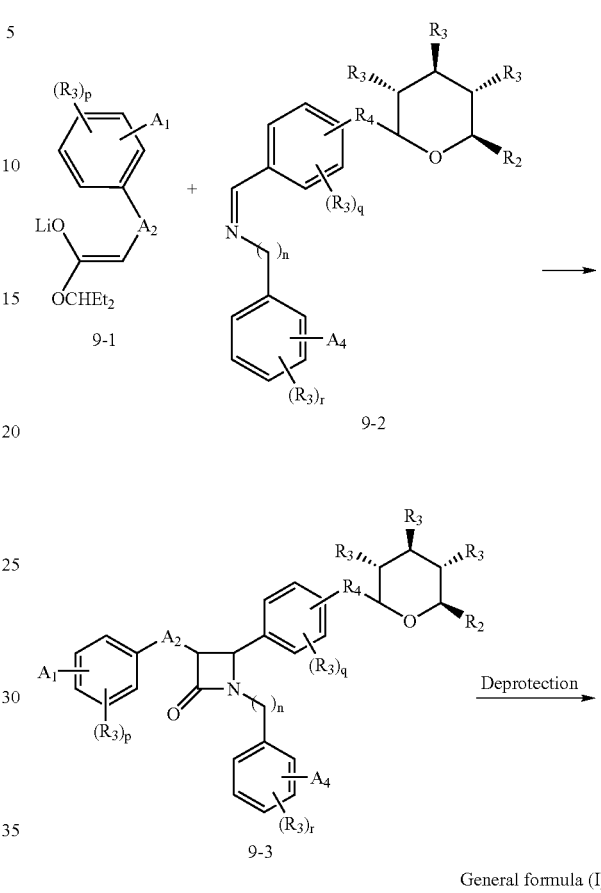

Method 10

The preparative method of the optically active compounds (III).

The compound (10-1) is condenced with the compound (9-2) to provide the compound (10-4) by E. J. Corey's method (E. J. Corey et al., Tetrahedron Lett. 1991, 32, 5287). The compound of general formula (I) is obtained by deprotection of the compound (10-4).

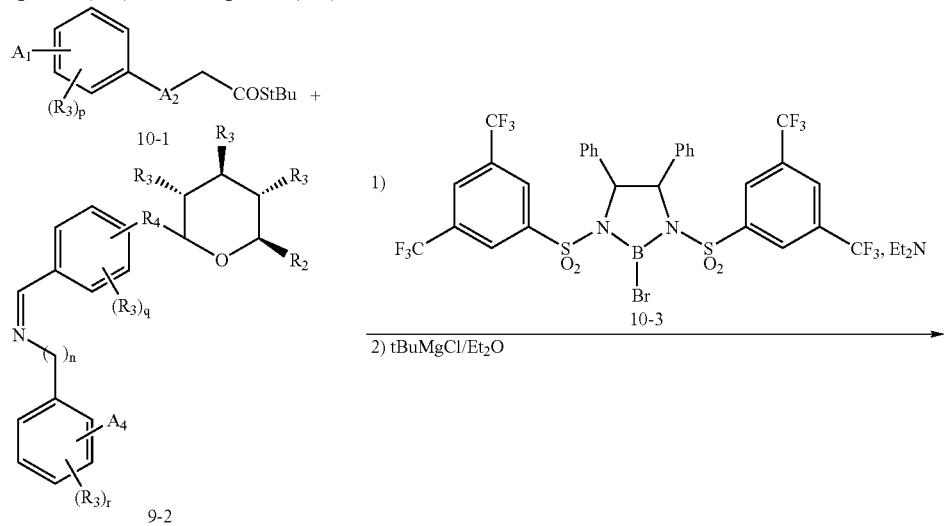

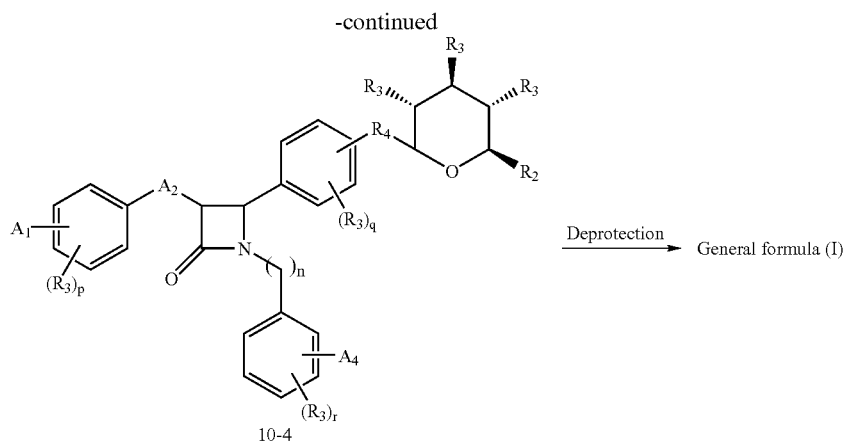

10-4

$\xrightarrow{\text{Deprotection}}$ General formula (I)

Method 11

The preparative method of the optically active compounds (IV).

(R)-(+)-2,10-camphorsultam (11-1) is reacted with acid chloride (11-2) and obtained the compound (11-3). The compound (11-5) is obtained by coupling reaction of the compound (11-3) and the compound (11-4) in the presence of Lewis acids (TiCl$_4$, BF$_3$.OEt$_2$). The compound (11-5) is reacted with BSA, followed by reaction with TBAF (n-tetrabutylammonium fluoride) to afford the β-lactam compound (11-6).

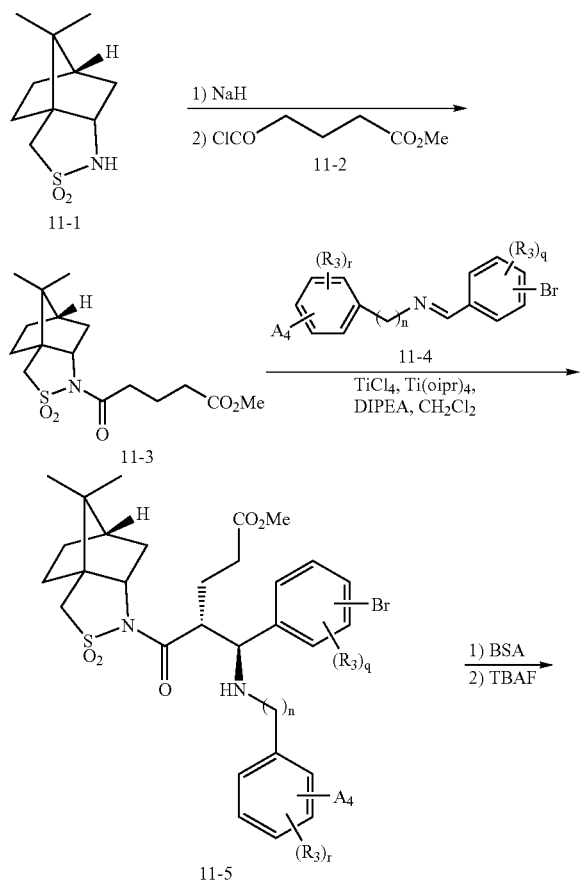

The obtained compound (11-6) is converted to the compound (8-15) by the same method as the method 8.

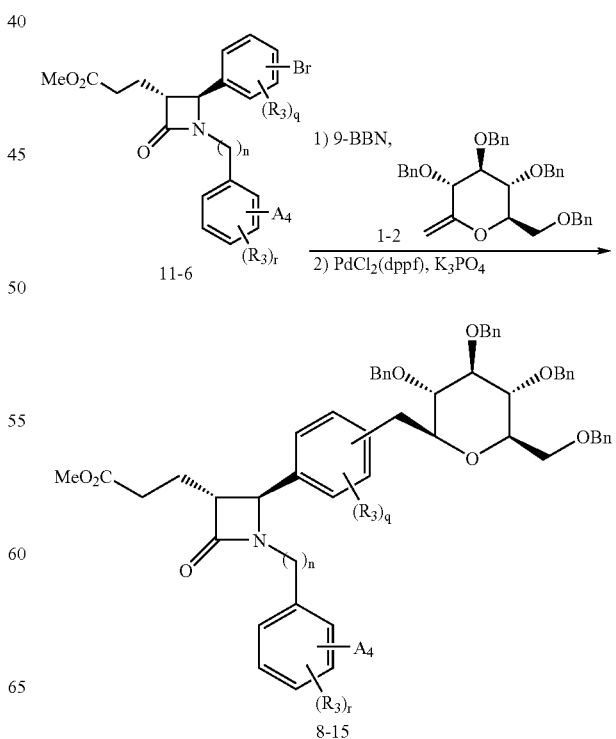

The compound (11-6) can be used as the starting material of the compound of general formula (I), according to the method 8. Furthermore, when the compound (11-7) is used instead of the compound (11-4), the compound (11-8) which correspond to the compound (11-6) can be obtained by the same method.

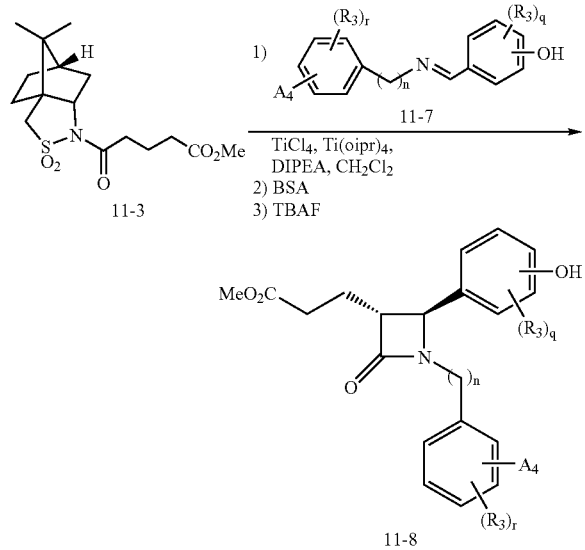

The compound (11-9) can be obtained from the compound (11-8) by the same method as the method 7.

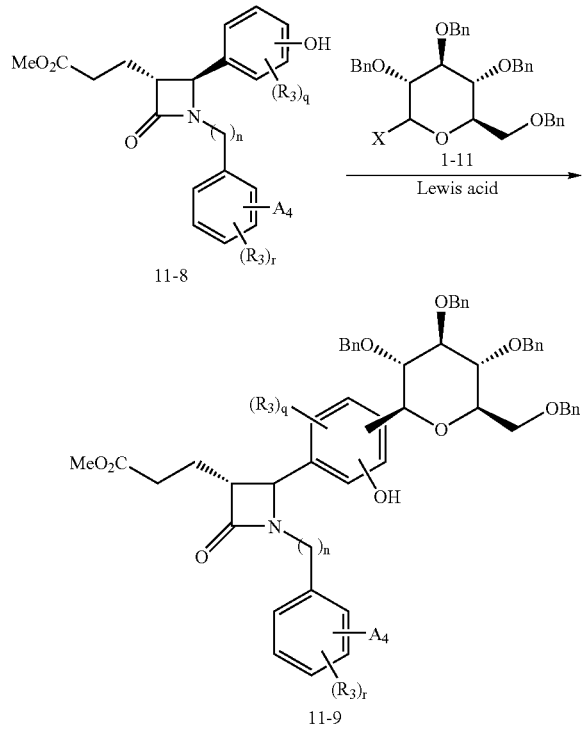

The compound (11-9) can be used as the starting material of general formula (I), according to the method 8.

Method 12

The compound (11-6) is subjected to Heck reaction with the compound (12-1) prepared by reported method (M.

Yokoyama et al., Synthesis 1998, 409) and obtain the compound (12-2). (R. F. Heck et al., J. Am. Chem. Soc. 1968, 90, 5518) The compound (12-2) can be used as the starting material of general formula (I), according to the method 8.

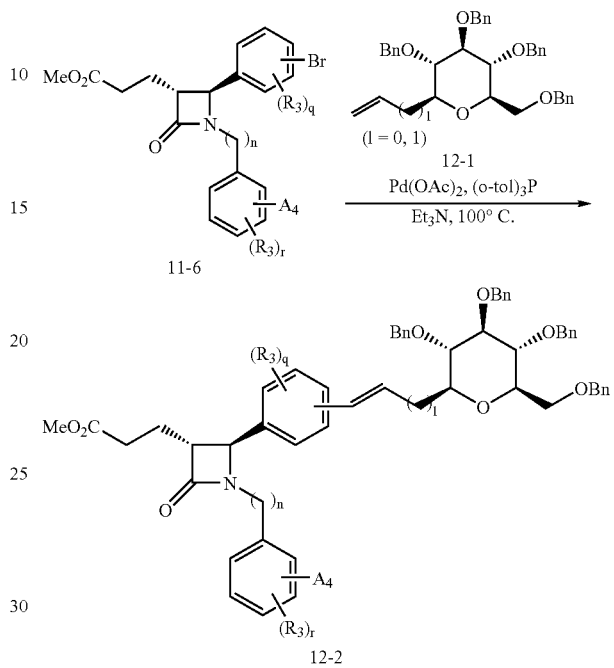

The compound (12-3) is obtained by hydrogenation of the compound (12-2). The compound (12-3) can be used as the starting material of general formula (I), according to the method 8.

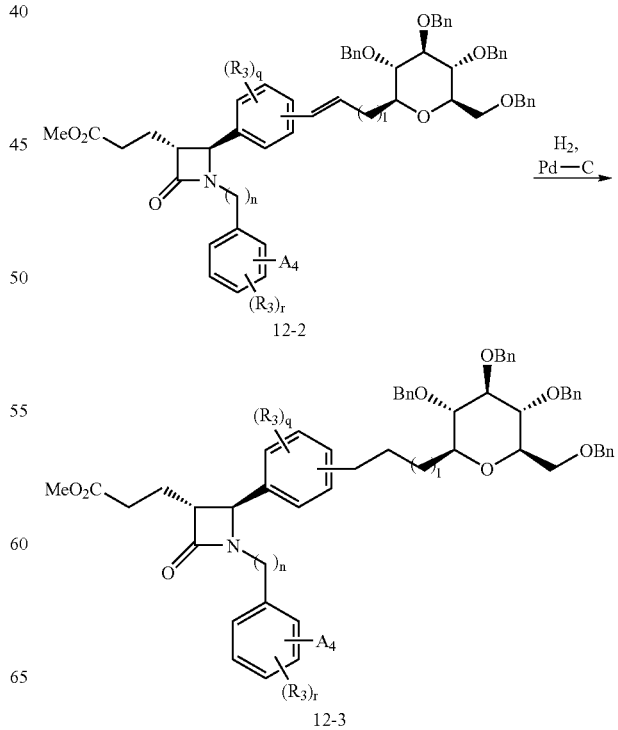

Method 13

C-glycosidation of the compound (13-1) with the compound (1-11) ($R_6$ is -Me, —Br, or —CH$_2$OTBS) provides the compound (13-2) in the presence of Lewis acid (BF$_3$.OEt$_2$, ZnCl$_2$, AgOTf). (K. C. Nicolaou et al., J. Chem. Soc., Chem. Comm. 1984, 1153) The $R_6$ of the compound (13-2) is converted to aldehyde by the same method as the method 1-(1)-(6), 1-(2), or 2-(2). The obtained compound can be used as the starting material of general formula (I), according to the method 1.

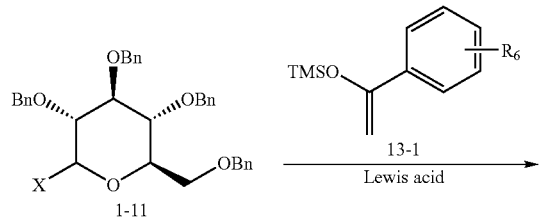

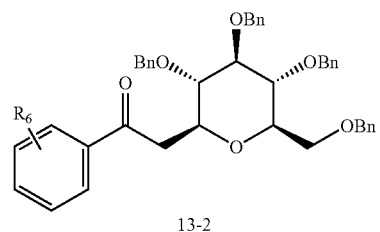

Method 14

The compound (14-1) is subjected to the coupling reaction such as Suzuki coupling reaction and Grignard reaction (Angew. Chem. Int. Ed. Engl. 2000, 4415), or alkylation in the presence of base. After deprotection, the compound (14-3) is obtained.

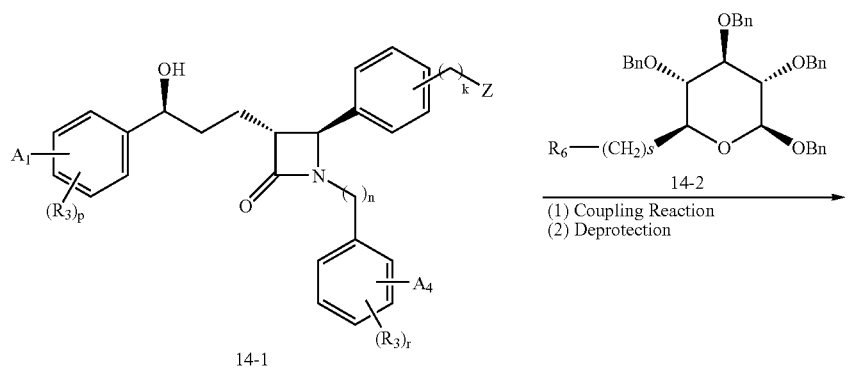

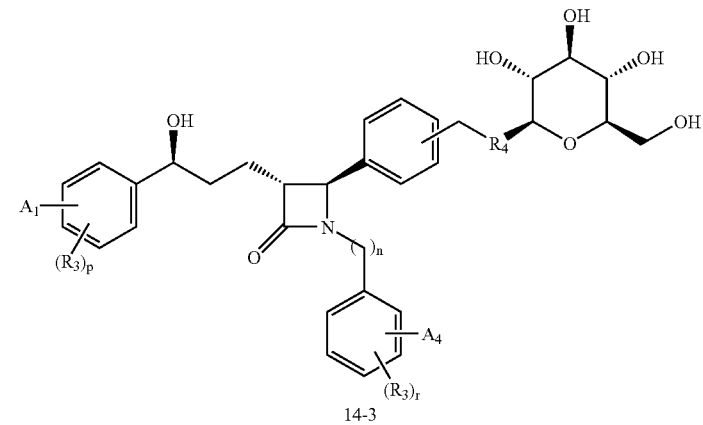

Method 15

The compound (15-1) which is prepared by L. Dheilly's method (L. Dheilly et al., Carbohydr. Res. 1992, 224, 301), is converted to the compound (15-2) by reduction and halogenation. The compound (15-2) is transformed to the organometalic reagents (Grignard reagent, organozinc reagent), followed by coupling reaction with the compound (15-3) in the presence of palladium or nickel catalysts. Then, the compound (15-4) is obtained by cyclization.

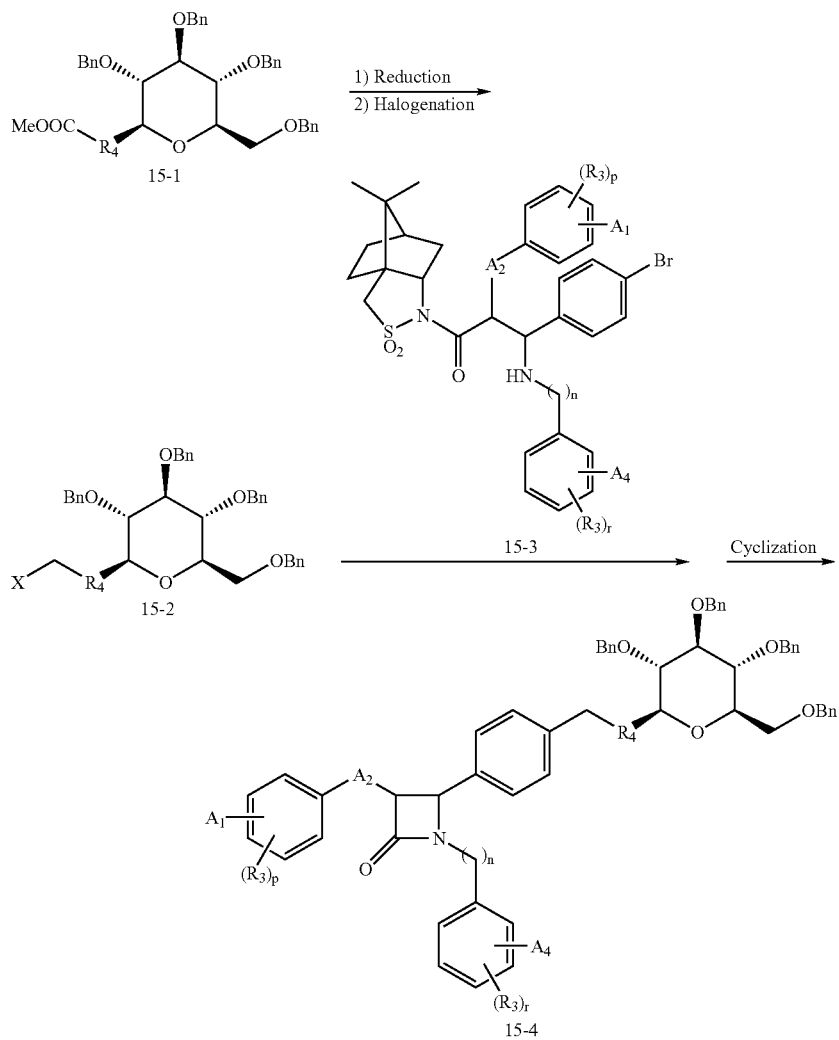

Method 16

The compound (16-1) can be obtained by Heck reaction using the compound (12-1) and the compound (15-3) as same as the method 12. The compound (16-1) is converted to the genaral formula (I) according to the method 17.

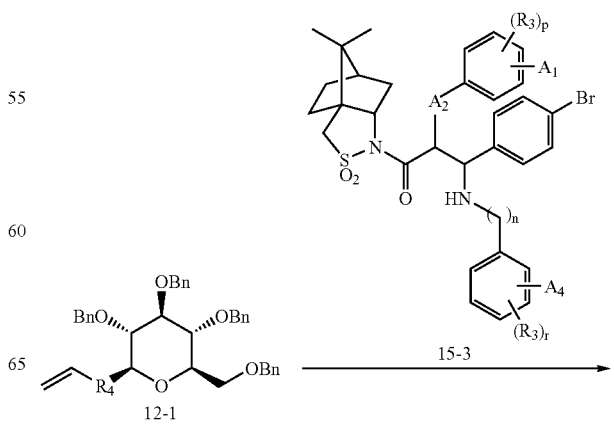

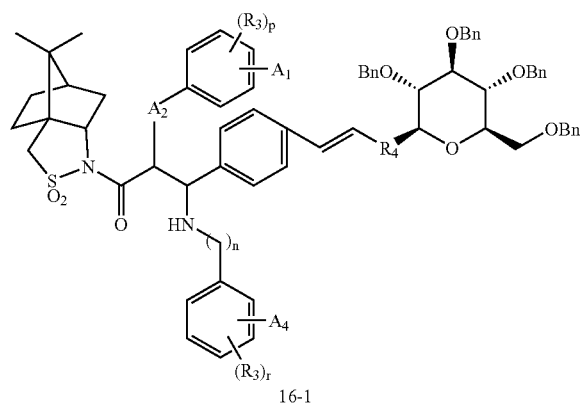

16-1

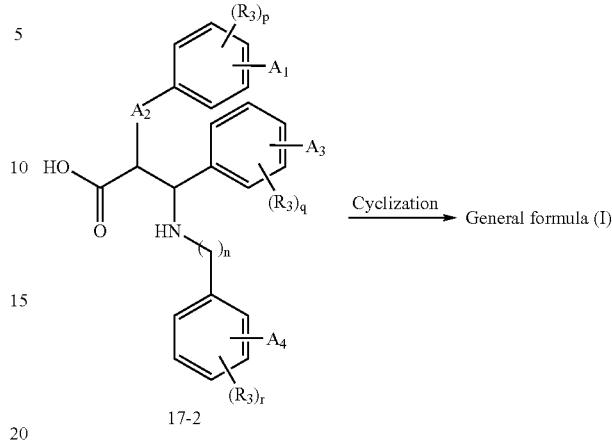

17-2

Method 17

The compound (17-1) is treated with lithium hydroxide to remove camphorsultam and obtained the compound (17-2). (The camphorsultam can be collected and reused.) Then, the compound (17-2) is cyclized with POCl$_3$ in the solvent such as dichloromethane or dichloroethane to yield the general formula (I). The compound of general formula (I) is also obtained by using the condensing reagents such as DCC (1,3-Dicyclohexycarbodiimide) or DEPC (Diethylphosphorylcyanide) in dichloromethane or DMF in the presence of base. Further the compound of general formula (I) is also obtained by using Mitsunobu reagent, DEAD (Diethylazodicarboxylate) or DIAD (Diisopropylazodicarboxylate) with Bu$_3$P or Ph$_3$P or by reacting with (PyS)$_2$ or after reacting with 2,6-dichloro-benzoyl chloride or 2,4,6-trichloro benzoyl chloride in the presence of NaH and treating with base like NaOH solution and obtained the general formula (I).

Or the compound (17-2) is esterified to the compound (17-3), followed by reaction of base such as LDA, LiHMDS (lithium bis(trimethylsilyl)amide), NaHMDS (sodium bis(trimethylsilyl)amide), NaH, t-BuOK in solvent such as THF to yield the general formula (I). The general formula (I) is also obtained by a reaction of Grignard reagent such as EtMgBr, t-BuMgBr with compound (17-3). Applying the same reaction to the compound (17-1), the compound of the general formula (I) is obtained.

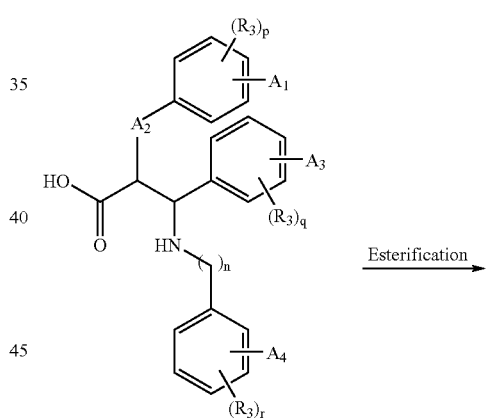

17-2

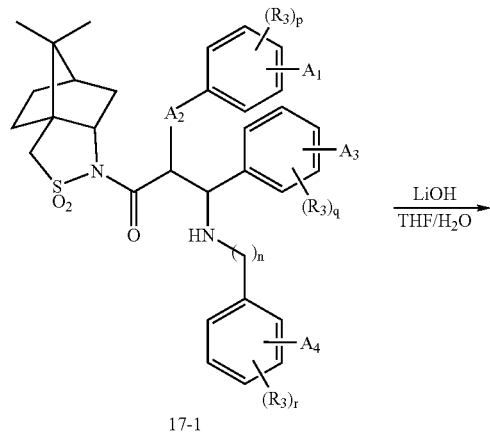

17-1

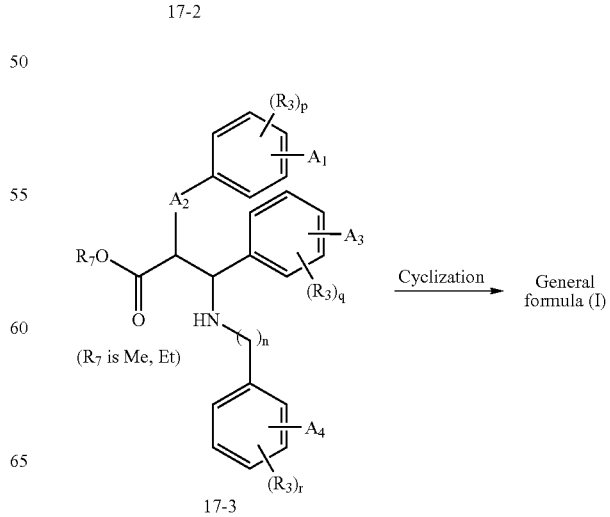

(R$_7$ is Me, Et)

17-3

Method 18

The compound (18-2) is obtained by SeO$_2$ oxidation of the compound (18-4) or Pd(OAc)$_2$-benzquinone-HClO$_4$ oxidation of the compound (18-4), then an asymmetric reduction of the ketone group of compound (18-2) provided to the compound (18-3). The compound (18-3) are also obtained by hydroboration of the compound (18-4). When a chiral borane reductant is used, the hydroboration proceeds stereoselectively.

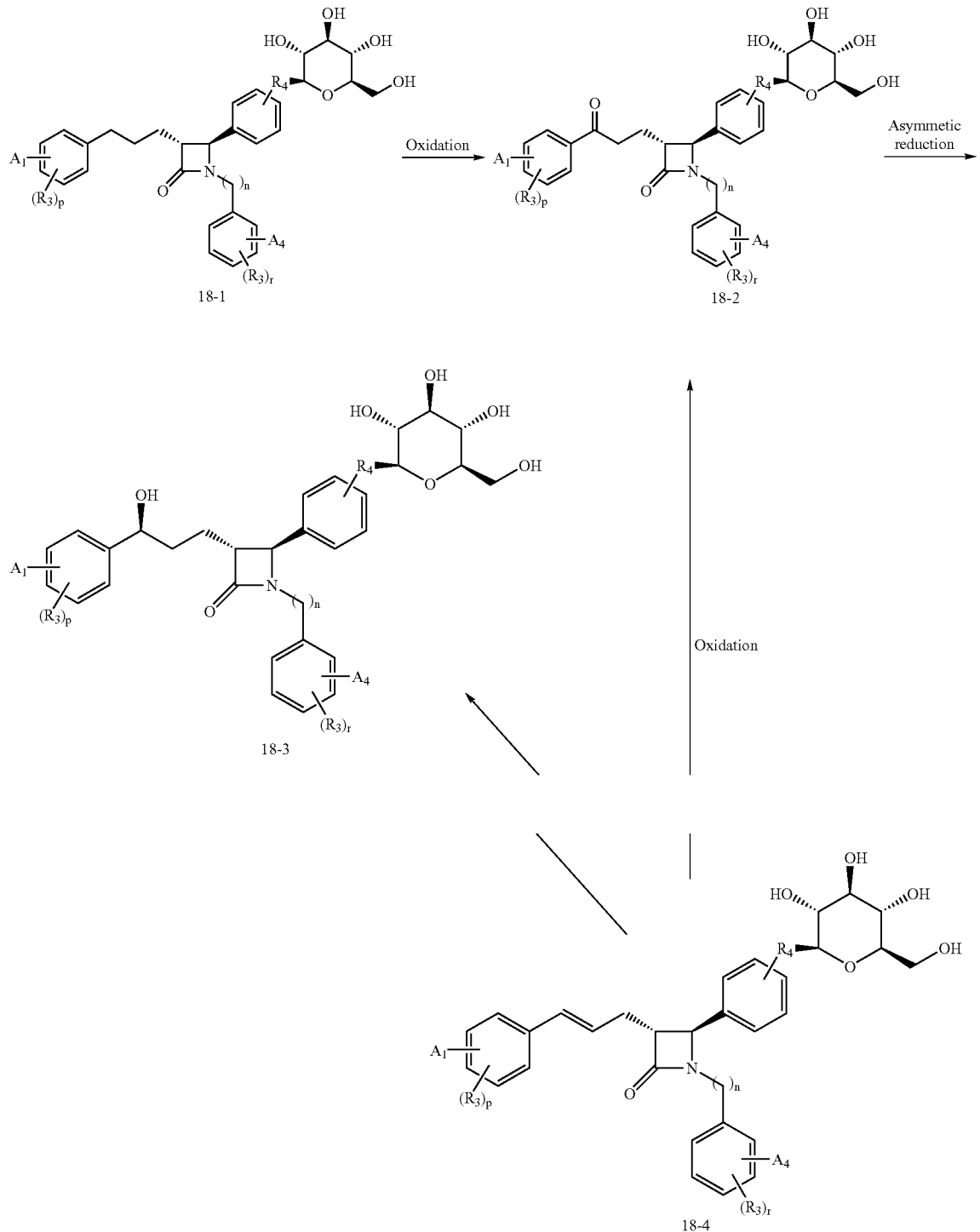

In the formula which are discribed between method 1 and method 18, $A_1$, $A_2$, $A_4$, $R_3$, $R_4$, p, q, r, and Z are as mentioned above, and $R_6$ is —CH=CH$_2$, —CH$_2$OH. k is integer of $\geq 1$, l is 0 or an integer of $\geq 1$, k+l is an integer of $\leq 10$.

Method 19

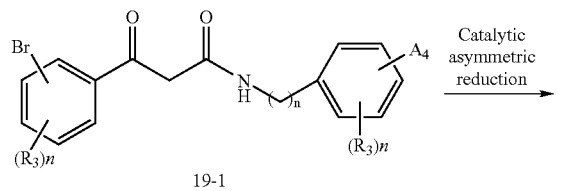
19-1

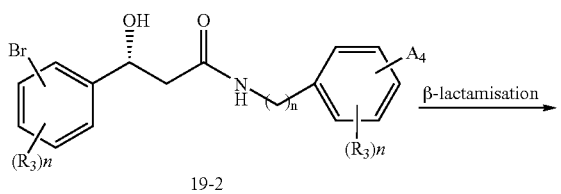
19-2

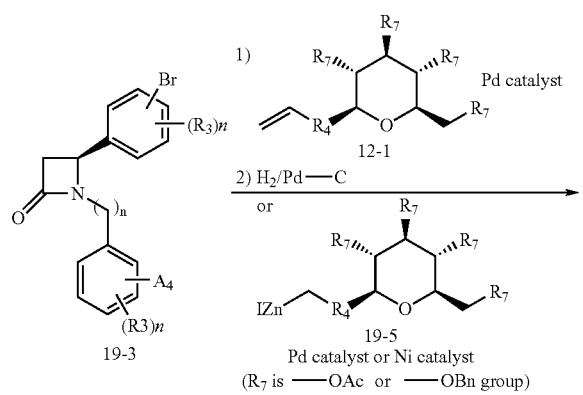
19-3

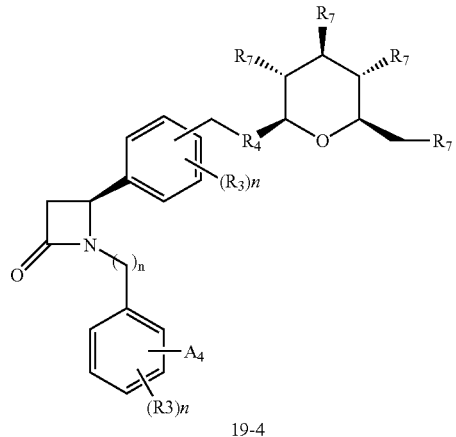
19-4

The compound (19-2) is obtained by asymmetric reduction of the compound (19-1). As asymmetric reductions, the transition metal catalysts are used (R. Noyori et al., J. Am. Chem. Soc. 1987, 109, 5856.). After the hydroxy group of the compound (19-2) is converted to a leaving group, the resulting compound is cyclized to obtain the compound (19-3). Or directly the compound (19-3) is obtained by Mitsunobu reaction of the compound (19-2). The compound (19-3) is subjected to Heck reaction with the compound (12-1), then the generated double bond is hydrogenated to give the compound (19-4). Or the compound (19-3) is subjected to Negishi coupling reaction (T. Hayashi et al., J. Am. Chem. Soc. 1984, 106, 158–163.; A. Saiga et al., Tetrahedron Lett. 2000, 41, 4629–4632; C. Dai et al., J. Am. Chem. Soc., 2001, 123, 2719–2724) with the compound (19-5) to obtain the compound (19-4). The compound (19-4) can be used the synthetic material of the general formula (I) according to example 8.

Method 20

Synthesis of Compound (19-3)

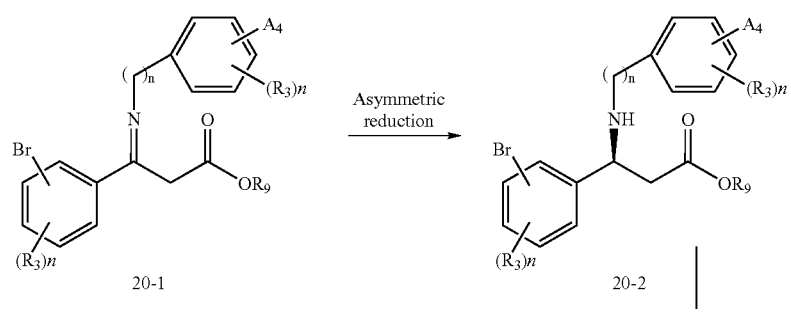

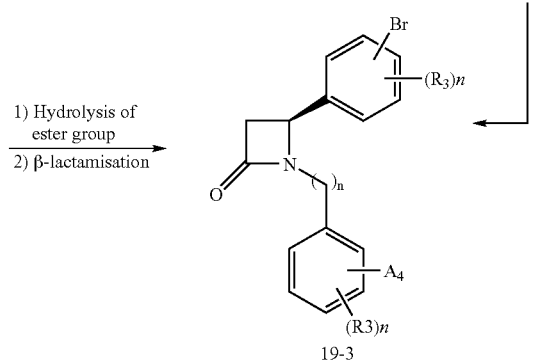

The imine compound (20-1) is subjected to asymmetric reduction to obtain the compound (20-2) according to example 19. The ester group of the compound (20-2) is hydrolyzed to the corresponding carboxylic acid compound and the obtained carboxylic acid is subject to β-lactamisation by using the condensing reagent (for example DCC) to give the compound (19-3). The compound (19-3) is also obtained by β-lactamisation of the compound (20-2) using EtNgBr for example. The compound (19-3) can be used the synthetic material of the general formula (I) according to example 19.

Method 21

Synthesis of Compound (21-10)

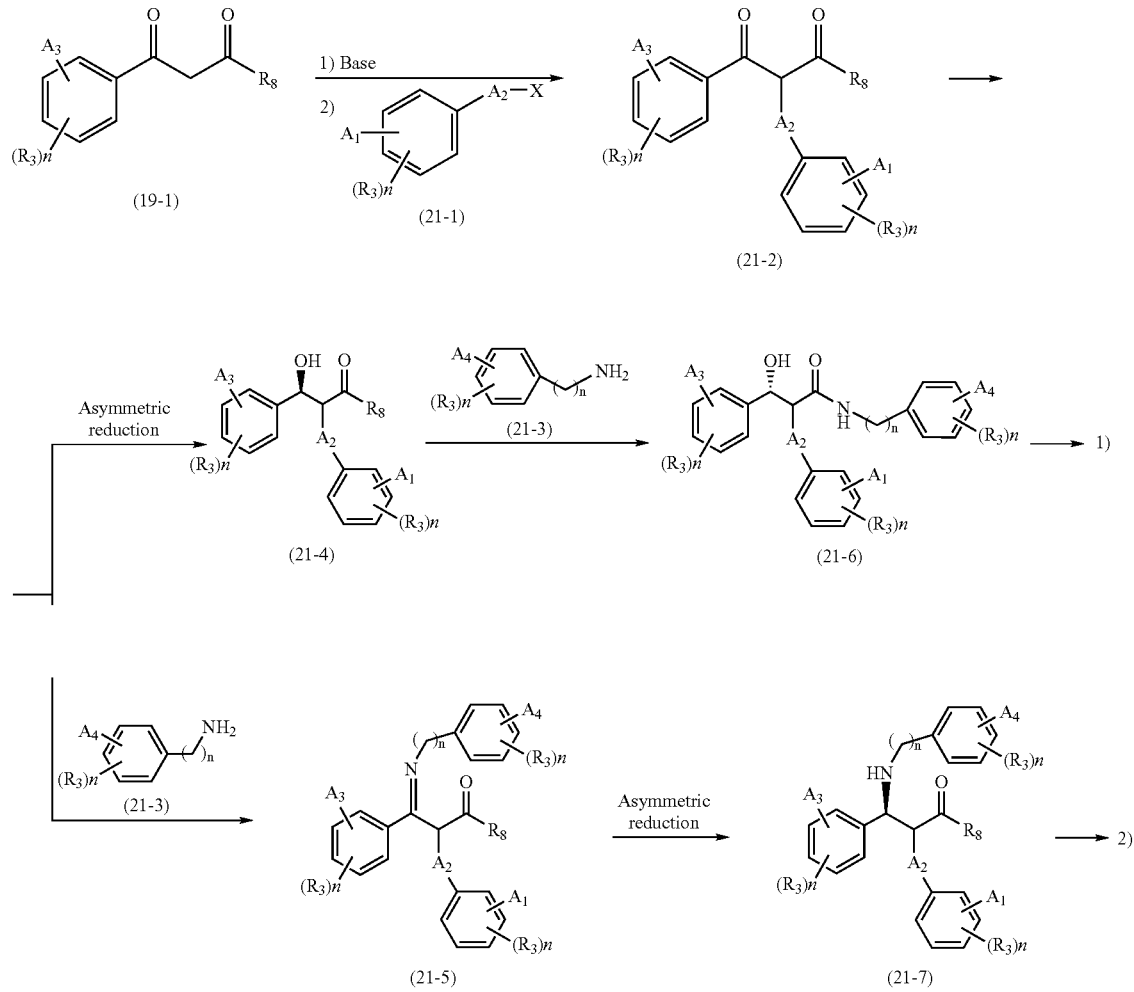

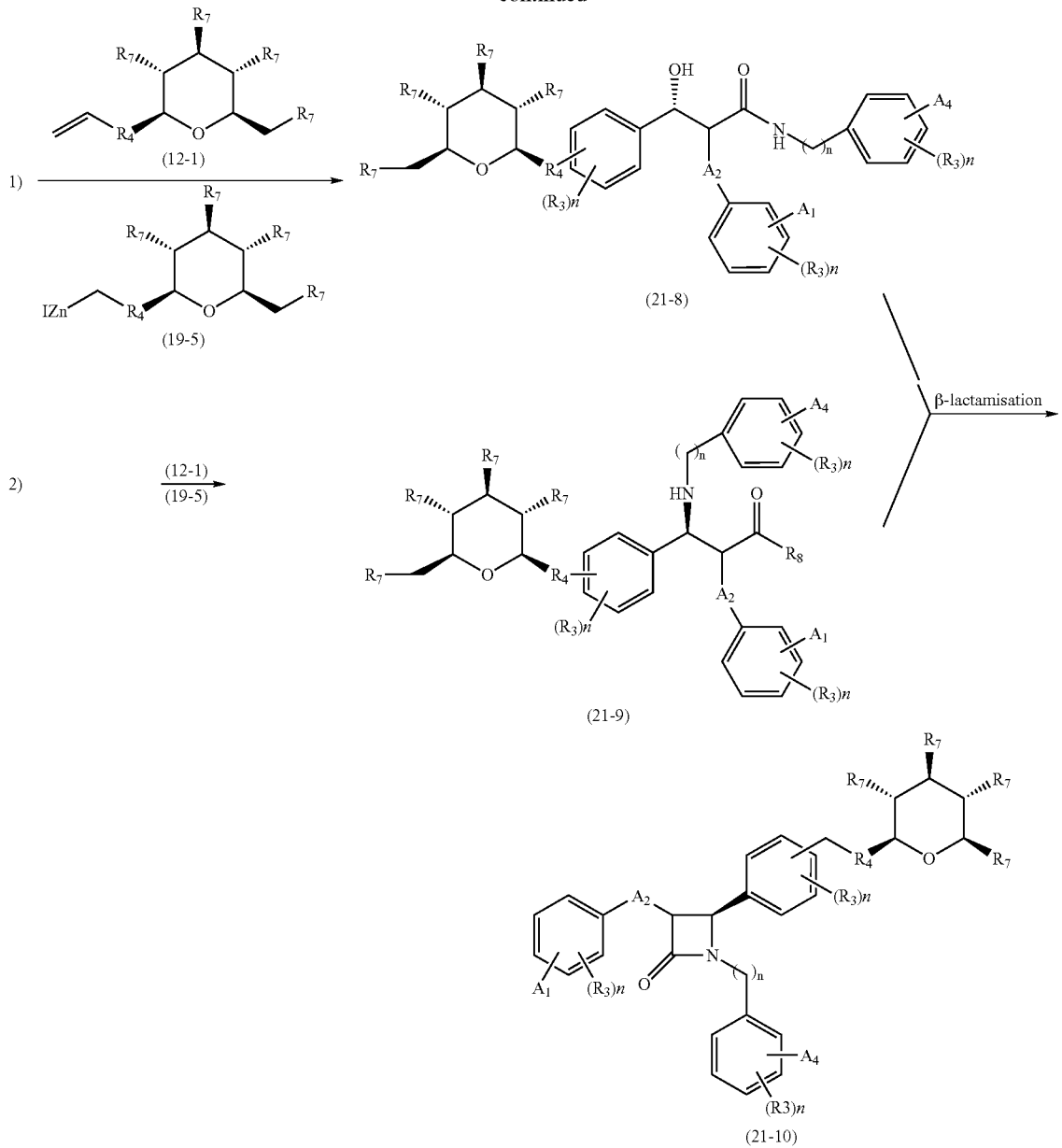

The compound (19-1) is reacted with an base, followed by addition of the compound (21-1) to give the compound (21-2). The compound (21-2) is converted to the compound (21-4) by asymmetric reduction or to the compound (21-5) by reaction with the compound (21-3).

The compound (21-4) is reacted with the compound (21-3) to afford the compound (21-6). Subsequently, the compound (21-6) is coupled with the sugar compound (12-1 or 19-5) to give the compound (21-8), then the β-lactam compound (21-10) is obtained.

On the other hand, after the compound (21-7) is obtained by asymmetric reduction of the compound (21-5) and the obtained compound (21-7) is coupled with the sugar compound (12-1 or 19-5) to afford the compound (21-9). The compound (21-10) is also obtained by β-lactamisation of the compound (21-9). The compound (21-10) can be the synthetic material of the general formula (I).

[Hypocholesterolemic Agents Using the Hypercholesterolemic Hamster]

Hamsters were derived into groups with 3 animals per group and fed a 0.5%-cholesterol containing CE-2 diet (CLEA Japan Inc.) for 4 or 7 days. The normal dietary group were fed a standard CE-2 during the experiment. Each compound or vehicle (0.2 mL of corn oil) per 100 g body weight was orally administered daily for 4 or 7 days from the day that high-cholesterol diet was started. At 20 hr after the final administration, blood samples were collected from the abdominal aorta of non-fasted animals under anesthesia with diethylether. Serum cholesterol was measured by enzymatic method using cholesterol E-test wako (Wako Pure Chemical Industries). Activity of the test compounds is expressed as percent reduction of the test compound on the basis of comparison with rised total cholesterol treated only with no-treatment-high-cholesterol diet. The test compounds with the optical rotation value in the compounds 1–58 were evaluated as the chiral compounds. The result is shown in the next table. Each value in the table shows the changed percent and the negative value indicates the positive hypocholesterolemic action.

TABLE 13

| No. | Test Comp. (mg/kg) | Dosage day | Serum cholesterol (%) |
|---|---|---|---|
| 2 | 3 | 7 | −120 |
| 13 | 20 | 4 | −28 |
| 15 | 20 | 4 | −21 |
| 23 | 3 | 7 | −177 |
| 24 | 3 | 7 | −156 |
| 28 | 3 | 7 | −130 |
| 33 | 3 | 4 | −67 |
| 38 | 10 | 4 | −2 |
| 45 | 3 | 4 | −136 |
| 46 | 3 | 4 | −147 |
| 49 | 10 | 4 | −55 |
| 56 | 0.3 | 4 | −84.0 |
| 57 | 0.3 | 4 | −81.3 |

[Biological Stability Test]

To evaluate the stability of C-glycoside, the biological stability of C-allyl derivative (A) and O-allyl derivative (B) against to α-N-acetyl-D-galactosaminidase as glycosidase ware compared according to Mark von Itzstein's method (Org. Lett., 1999, 1, 443–446).

[Chemical Formula 69]

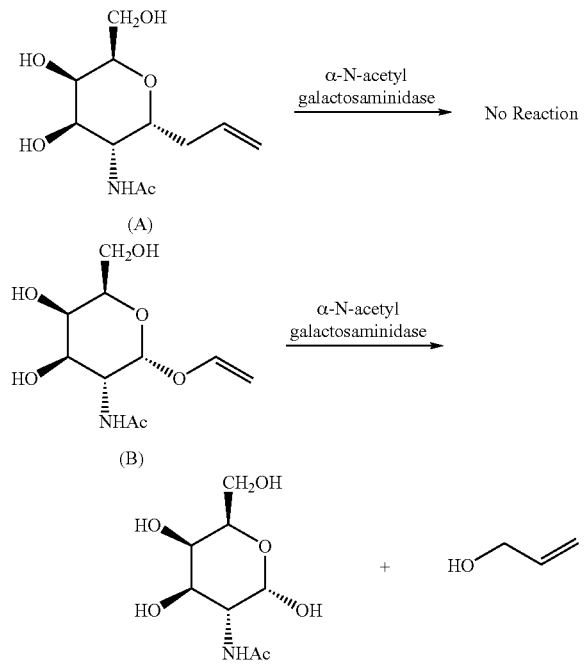

enzyme; α-N-acetyl galactosaminidase 0.32 unit (1.69 unit/mL 0.1% BSA containing 0.5M sodium citrate buffer)
solvent; citric acid buffer (pD=3) 0.6 mL
temperature; 35° C.
procedure; Substrate (2 mg) was dissolved in citric acid buffer (0.6 mL) and α-N-acetyl galactosaminidase (0.32 unit) was added. NMR spectrum was determined in every constant time and the content of the remaining substrates were determined.

The result of the remaining substrates were shown in table 14.

TABLE 14

| | time | | | | | | | |
|---|---|---|---|---|---|---|---|---|
| substrate | 2 | 4 | 6 | 8 | 10 | 12 | 18 | 24 |
| B | 89 | 79 | 68 | 57 | 50 | 45 | 40 | 22 |
| A | 100 | 100 | 100 | 100 | 100 | 100 | 100 | 100 |

From the above results, 78% of O-allyl derivative (B) was clearly hydrolyzed after 24 h. C-allyl derivative (A), replaced ether bond to C—C bond, was unaffected by enzyme as expected and the formation of the degradation was not observed after 24 h.

EXAMPLE

The following examples are provided only for the purpose of the preparation of the compound and not restrict the disclosed invention.

Reference 1

4-(4-{[(5S,2R,3R,4R,6R)-3,4,5-trihydroxy-6-(hydroxymethyl)-perhydro-2H-pyran-2-yl-]methyl)phenyl)(4S*,3S*)-1-(4-fluorophenyl)-3-[3-(4-fluorophenyl)propyl]azetidine-2-on

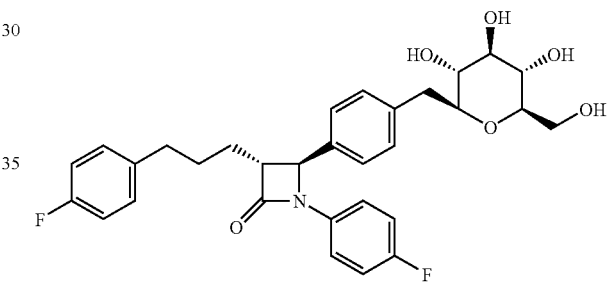

Reference 1-a

Synthesis of Compound (1-4)

A 50 mL of 9-BBN (0.5 M tetrahydrofuran solution) was added to a solution of the compound (1-2) (5.37 g) in tetrahydrofuran (70 mL) and the mixture was refluxed for 5 hr, cooled to room temperature and 3 M potassium phosphate (10 mL) was added to the mixture at room temperature for 15 min. To the reaction mixture was added a solution of 4-(tert-butyldimethyl-silyloxymethyl)bromo-benzene (3.01 g) and PdCl$_2$ (dppf) (0.73 g) in N,N-dimethylformamide (100 mL). The mixture was stirred for 18 hr. The organic layer was washed with brine, dried over anhydrous sodium sulfate, and concentrated under reduced pressure. To the residue was added tetrabutylammonium fluoride (1.0 M tetrahydrofuran solution) (15 mL). The mixture was stirred for 3 hr and extracted with ethyl acetate. The organic layer was washed with brine, dried over anhydrous sodium sulfate, and concentrated. The residue was purified by silica gel column chromatography (ethyl acetate/hexane=1/2) to give 3.58 g (2 steps, 56%) of the compound (1-4).

Mass (ESI) m/z: 662 (M+H$_2$O)$^+$ IR (KBr): 3430 cm$^{-1}$ H-NMR (CDCl$_3$): 2.71(d,J=8.8, 13.2 Hz), 3.13(d,J=2.4, 14.2 Hz), 3.32~3.36(m,2H), 3.45~3.50(m,1H), 3.60~3.74 (m,4H), 4.48~4.68(m,6H), 4.80~4.95(m,4H), 7.18~7.37(m, 24H)

Reference 1-b

Synthesis of Compound (1-5)

To a solution of the compound (14) (3.6 g) in chloroform (22.0 mL) was added manganese dioxide (9.65 g) and the mixture was refluxed for 2 hr, and cooled to room temperature. The mixture was filtered through a pad of Celite and evaporated to gave 3.46 g (97%) of the compound (1-5) as a colorless crystal.

Mass (ESI) m/z: 660 (M+H$_2$O)$^+$ IR (KBr): 1692 cm$^{-1}$ $^1$H-NMR(CDCl$_3$): 2.77(d,J=8.8, 14.2 Hz), 3.16~3.20(m,1H), 3.32~3.36(m,2H), 3.49(dt,J=2.0, 9.3 Hz), 3.61~3.66(m,3H), 3.72(t,J=8.8 Hz), 4.46~4.67(m,4H), 4.81~4.97(m,4H), 7.18~7.41(m,22H), 7.74(d,J=8.3 Hz), 9.95(s,1H)

Example 1

(I) To a solution of the compound (1-5) (3.46 g) in toluene (54.0 mL) were added molecular sieve (3.46 g), a catalytic ammount of p-toluenesulfonic acid and p-fluoroaniline (0.61 mL). The mixture was refluxed for 1.5 hr and filtered. The solvent was removed under reduced pressure and the residue was subjected to the next reaction without purification.

(II) To the solution of the compound obtained above in toluene (54.0 mL) were added tributylamine (5.1 mL) and 5-(4-fluorophenyl)pentanoyl chloride (1.16 g). After the mixture was refluxed for 15 hr and 1 N hydrochloric acid (15 mL) was added to the mixture and the mixture was stirred for 15 min. The organic layer was separated and washed with saturated sodium bicarbonate solution, brine and dried over anhydrous sodium sulfate and concentrated. The residue was subjected to the next reaction without purification.

(III) The solution of the compound obtained above in methanol-tetrahydrofuran (5/1) (6 mL) was hydrogenated at room temperature for 5 hr in the presence of 10% palladium on carbon (200 mg). After removal of the catalyst and the reaction mixture was evaporated and the residue was chromatographed on silica gel (chloroform/methanol=10/1) to give 64 mg (26%) of the compound 2.

Mass (ESI) m/z: 554 (M+H)$^+$0 IR (KBr): 3376, 1737, 1503, 1218 cm$^{-1}$ $^1$H-NMR (CD$_3$OD): 1.82~1.98(m,4H), 2.65~2.78(m,3H), 3.09~3.39(m,7H), 3.64(d,J=5.4, 12.2 Hz), 3.77~3.81(m,1H), 4.94~4.98(m,1H), 6.98~7.05(m,4H), 7.18~7.22(m,2H), 7.30~7.33(m,4H), 7.38(d,J=7.8 Hz,2H)

Example 2

Synthesis of Compound 3

4-(4-([(5S,2R,3R,4R,6R)-3,4,5-triacetoxy-6-(acetoxymethyl)-perhydro-2H-pyrane-2-yl]methyl}phenyl)-(4S*,3S*)-1-(4-fluorophenyl)-3-[3-(4-fluorofenyl)propyl]azetidine-2-one

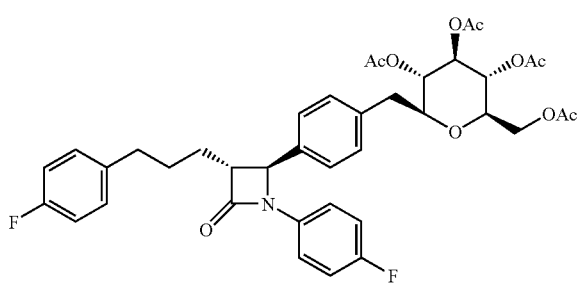

To a solution of the compound 2 (600 mg) in dichloromethane (11.0 mL) were added triethylamine (0.77 mL), acetic anhydride (0.49 mL) and a catalytic ammount of 4-dimethylaminopyridine. The mixture was stirred at room temperature for 16 hr. The organic layer was washed with brine, dried over anhydrous sodium sulfate and concentrated. The residue was purified by silica gel column chromatography (ethyl acetate/hexane=1/2) to give 600 mg (77%) of the compound 3.

Mass (ESI) m/z: 722 (M+H)$^+$ IR (KBr): 1749, 1506, 1380, 1221, 1029 cm$^{-1}$ $^1$H-NMR (CDCl$_3$): 1.82~1.84(m, 4H), 1.93(s,3H), 1.97(s,1.5H), 1.98(s,1.5H), 1.99(s,1.5H), 2.00(s,1.5H), 2.02(s,3H), 2.61~2.64(m,2H), 2.79~2.82(m, 2H), 3.07~3.08(m,1H), 3.56~3.69(m,2H), 4.02~4.23(m, 2H), 4.58(d,J=2.4 Hz), 4.89~4.95(m,1H), 5.03(t,J=9.3 Hz), 5.17(t, J=9.3 Hz), 6.90~7.007(m,4H), 7.08~7.12(m,2H), 7.18~7.24(m,6H)

Reference 2

Synthesis of Compound (2-2)

4-(2,3,4,6-tetra-o-benzyl-β-D-glucopyranosyl)benzyl alcohol

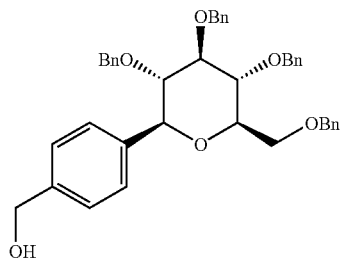

To 7.31 g of tetrabenzylgluconolactone was added dropwise at −78° C. the lithium anion, prepared from 6.66 g of p-(tert-butyldiphenylsilyloxymethyl)bromobenzene and 10 mL of n-butyl lithium (1.57 M hexane solution) at −78° C. The mixture was stirred for 2 hr and extracted with ethyl acetate. The organic layer was washed with brine, dried over anhydrous sodium sulfate and concentrated. The residue was subjected to the next reaction without purification. To a solution of the compound obtained above in dichloromethane (26 mL) were added triethylsilane (0.82 mL) and borontrifluoride-diethylether complex (0.33 mL) at −50° C. The mixture was stirred for 1.5 hr. Sodium bicarbonate solution was added. The mixture was stirred for 1 hr, and then it was extracted with ether. The organic layer was washed with brine, dried over anhydrous sodium sulfate, and concentrated. The residue was purified by silica gel column chromatography to give 1.48 g (15%) of the compound (2-2).

IR (KBr): 3388, 1452, 1362, 1210, 1068, 1026 cm$^{-1}$ $^1$H-NMR (CDCl$_3$): 3.49~3.81(m,4H), 4.04~4.96(m,13H), 6.92~6.95(m,2H), 7.09~7.76(m, 2H)

Reference 3-a 4-(2,3,4,6-tetra-o-benzyl-β-D-glucopyranosyl)methoxy benzoic acid methyl ester

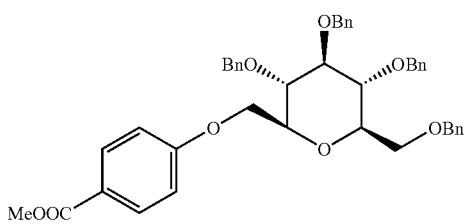

3-a

To a solution of the compound (3-1) (555 mg), methyl p-hydroxy benzoate (153 mg) and triphenylphosphine (394 mg) in tetrahydrofuran (5.0 mL) was added diisopropylazodicarboxylate (0.3 mL). The mixture was stirred for 22 hr and concentrated under reduced pressure. The residue was purified by silica gel column chromatography (ethyl acetate/hexane=1/3) to give 180 mg (26%) of the compound (3-a).

IR (neat): 1713, 1605, 1434, 1359, 1248, 1164 cm$^{-1}$
$_1$H-NMR (CDCl$_3$): 3.49~3.77(m,7H), 3.89(s,3H), 4.07~4.11 (m,1H), 4.19~4.22(m,1H), 4.51~4.60(m,4H), 4.82~4.89(m, 2H), 4.94(s,2H), 6.87(d,J=8.8 Hz,2H), 7.15~7.36(m,20H), 7.96(d,J=8.8 Hz,2H)

Reference 3-b 4-(2,3,4,6-tetra-o-benzyl-β-D-glucopyranosyl)methoxy benzyl alcohol

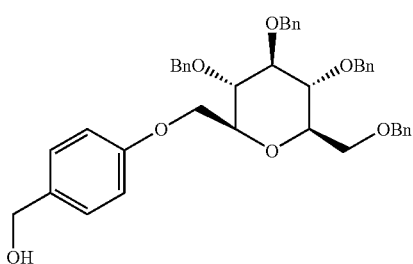

3-b

To a suspension of 10 mg of lithium aluminiumhydride in 5 mL of ether was added 180 mg of the compound (3-a) in 5 mL of ether at 0° C. After the mixture was stirred at room temperature for 15 min, water (2.0 mL) and 15% sodium hydroxide solution (0.5 mL) were added and the resulting suspension was filtered through a pad of Celite. After removal of the solvent, the residue was purified by silica gel column chromatography (ethyl acetate/hexane=1/1) to give 160 mg (93%) of the compound (3-b).

Mass (ESI) m/z: 684 (M+H+Na)$^+$ IR (neat): 3442 cm$^{-1}$
$_1$H-NMR (CDCl$_3$): 1.56(s,1H), 3.49~3.53(m,1H), 3.60~3.77 (m,6H), 4.08~4.12(m,1H), 4.20~4.23(m,1H), 4.52~4.61(m, 6H), 4.85(ABq,J=11.2 Hz,2H), 4.93(s,2H), 6.88(d,J=8.8 Hz,2H), 7.15~7.36(m,22H)

Reference 3-c

Synthesis of Compound (1-14)

4-(2,3,4,6-tetra-o-benzyl-β-D-glucopyranosyl)benzaldehyde

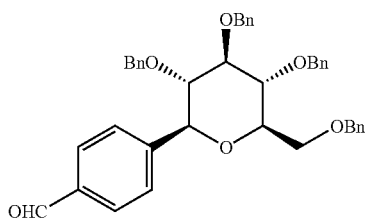

1-14

(I) To a solution of the 4-(2,3,4,6-tetra-o-benzyl-β-D-glucopyranosyl)toluene (0.3 g) in carbon tetrachloride (3 mL) were added NBS (0.9 mg) and benzoylperoxide (0.05 g). The mixture was refluxed for 2 hr. After cooling to room temperature, ether (30 mL) was added to the mixture. The resulting salts were filtered off by suction. The filtrate was concentrated and the residue was purified by silica gel column chromatography (ethyl acetate/hexane=1/8).

(II) To a solution of the bromide (224 mg) obtained above in dimethylsulfoxide (3 mL) was added sodium bicarbonate (45 mg). After the mixture was stirred at room temperature for 1 hr and 100° C. for 4 hr, the mixture was extracted with ethyl acetate (30 mL). The organic layer was washed with brine, and dried over anhydrous sodium sulfate. Removal of the solvent under reduced pressure gave the compound (1-14) (2 steps 26%).

Mass (m/z): 436 (M$^+$), 394, 307, 273, 245, 214, 163, 135, 105, 77, 51 (BP) IR (neat): 2914, 1641, 1437, 1257, 1017, 954, 708 cm$^{-1}$ $^1$H-NMR(CDCl$_2$,400 MHz)δ: 1.96, 1.97, 2.06(12H,each,s), 3.75~5.40(7H,m), 7.96, 8.02(4H, ABq), 10.06(1H,s)

Example 3

2-(4-[4-{(5S,2R,3R,4R,6R)-3,4,5-trihydroxy-6-(hydroxymethy)-perhydro-2H-pyran-2-yl} methyl]phenyl)(4S*,3R*)-1-(4-fluorophenyl)-3-[3-(4-fluorophenyl)propyl]-2-oxazetidineyl)phenoxy-2-methylpropanoic acid

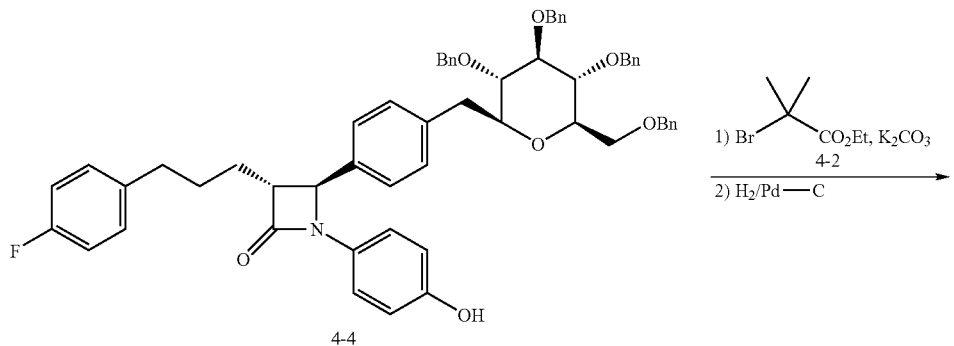

4-4

-continued

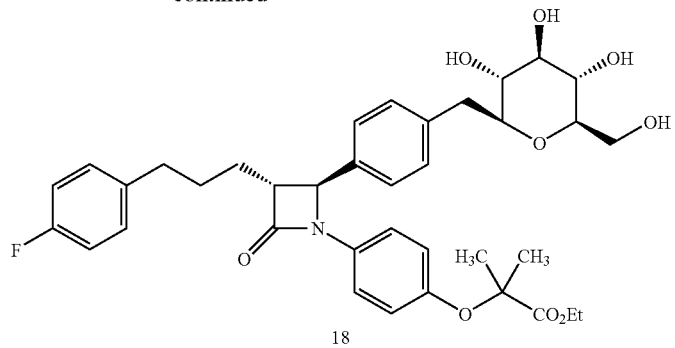

18

(I) To a solution of the compound (4-4) (3.19 g) in acetone (22.0 mL) were added ethyl 2-bromo-2-methylpropionate (0.77 mL) and potassium carbonate (0.97 g). The mixture was refluxed for 40 hr, filtered, and concentrated. The residue was purified by silica gel column chromatography (ethyl acetate/hexane=1/3).

(II) A solution of the compound 18 (2.93 g) obtained above in ethanol-tetrahydrofuran (1/1) (40 mL) was hydrogenated at room temperature for 3 hr in the presence of 10% palladium on carbon (0.3 g). After removal of the catalyst, the filtrate was evaporated. The residue was purified by silica gel column chromatography (chloroform/methanol=10/1) to give 1.21 g (2 steps 51.8%) of the compound 18.

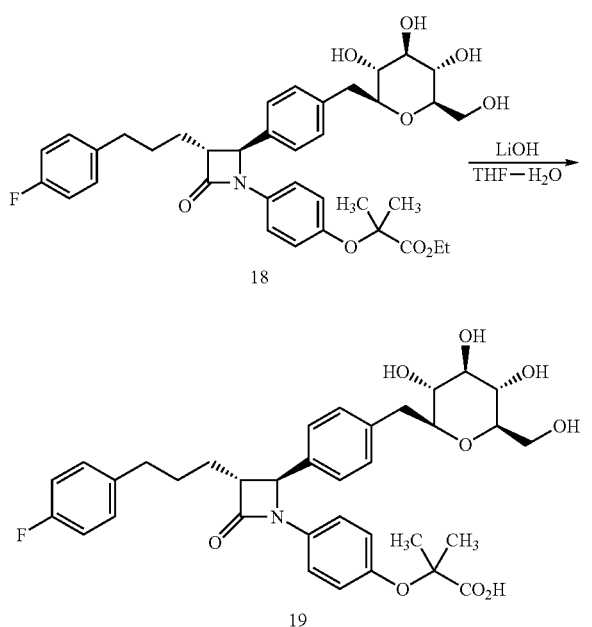

To a solution of the compound 18 (400 mg) in tetrahydrofuran-water (5/1) (3 mL) was added lithium hydroxide (50 mg). The mixture was stirred at room temperature for 8 hr and 1 N hydrochloric acid was added to adjust to pH 3. The mixture was extracted with ethyl acetate. The organic layer was washed with brine, dried over anhydrous sodium sulfate and concentrated. The residue was purified by silica gel column chromatography (chloroform/methanol=5/1) to give 377 mg (3 steps 51.0%) of the compound 19.

Mass (ESI) m/z: 636 (M–H)⁻ IR (KBr): 3400, 1722, 1503 cm⁻¹ ¹H-NMR(CD₃OD): 1.53(s,6H), 1.81~1.95(m,4H), 2.65~2.68(m,2H), 2.72~2.78(m,1H), 3.09~3.41(m,7H), 3.62~3.66(m,1H), 3.77~3.82(m,1H), 4.81(d,J=2.0 Hz,1H), 6.85(d,J=9.3 Hz, 2H), 6.97~7.02(m,2H), 7.18~7.22(m,4H), 7.30(d,J=7.8 Hz,1H), 7.38(d,J=8.3 Hz,2H)

Example 4

Synthesis of Compound 17

6-[(4-{(2S*,3S*)-1-(4-fluorophenyl)-3-[3-(4-fluorophenyl)propyl]-4-oxoazetidine-2-yl}(2S,3S,4R,5R,6R)-3,4,5-trihydroxyperhydro-2H-pyran-2-carboxylic acid

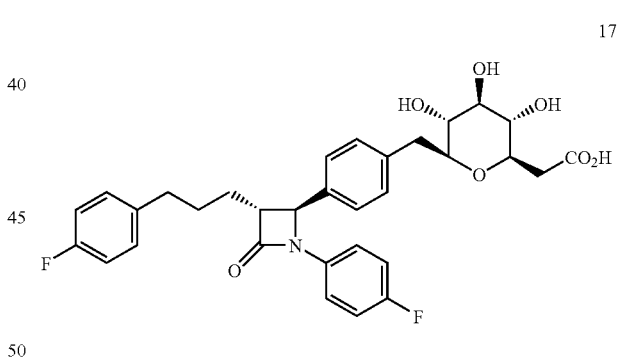

17

To a mixture of the compound 2 (300 mg), 2,2,6,6-tetramethyl-1-piperodinyloxy, free radical (10 mg) and potassium bromide (10 mg) in acetonitrile (6.6 mL) were added saturated sodium bicarbonate solution (6.6 mL) and sodium hypochlorite (6.6 mL). The mixture was stirred at room temperature for 3 hr and then extracted with ethyl acetate. The organic layer was washed with brine, dried over anhydrous sodium sulfate and concentrated. The residue was purified by silica gel column chromatography (chloroform/methanol=10/1) to give 90 mg (29.4%) of the compound 17.

Mass (ESI) m/z: 566 (M–H)⁻ IR (KBr): 3388, 1737, 1509 cm⁻¹ ¹H-NMR (CD₃OD): 1.82~1.97(m,4H), 2.65~2.68(m, 2H), 2.71~2.79(m,1H), 3.12~3.24(m, 3H), 3.34~3.52(m, 3H), 3.62~3.68(m,1H), 4.84(d,J=2.0 Hz,1H), 6.98~7.05(m, 4H), 7.18~7.21(m,2H), 7.29~7.37(m,6H)

Reference 4-a

Synthesis of Compound (8-2)

D-p-Benzyloxyphenylglycine

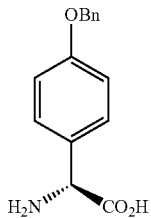

8-2

To a solution of D-p-hydroxyphenylglycine (16.7 g) in 2 N sodium hydroxide (50 mL) was added a solution of copper sulfate (12.5 g) in water (100 mL). The mixture was stirred at 60° C. for 1 hr. After cooling to room temperature, 2 N sodium hydroxide (50 mL), methanol (50 mL) benzyl bromide (13.0 mL) were added. The mixture was stirred at room temperature for 20 hr. Resulting salts were collected by suction, washed with water and acetone and the residue dissolved in 1 N hydrochloric acid (300 mL) and the mixture was stirred at room temperature for 1 hr. Resulting salts were collected by suction, washed with water and acetone and dried to give 13.18 g (51.3%) of the compound (8-2).

Mass m/z: 212 $(M-45)^+$, 122, 91(base), 65 IR (KBr): 3022, 1587, 1509, 1389, 1248, 1008 $cm^{-1}$ $^1$H-NMR ($CD_3OD$): 5.07(s,1H), 5.16(s,2H), 7.12(d,J=6.8 Hz,2H), 7.34~7.48(m,5H), 7.45(d, J=6.8 Hz,2H)

Reference 4-b

Synthesis of Compound (8-3)

D-p-Benzyloxyphenyl-N-(tert-buthoxycarbonyl)glycine

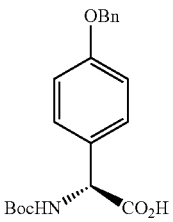

8-3

To a solution of the compound (8-2) (12.53 g) in tetrahydrofuran-water (140 mL) were added triethylamine (16.4 mL) and di-tert-butyl-dicarbonate (13.5 mL) at 0° C. After the mixture was stirred at room temperature for 4 hr, the mixture was concentrated under reduced pressure. The residue was added with 10% citric acid solution to pH 4 and extracted with ethyl acetate (100 mL×3). The organic layer was washed with water (100 mL×3), brine (100 mL) and dried ($Na_2SO_4$). After removal of the organic solvent under reduced pressure, 17.4 g (quantitative) of the compound (8-3) was obtained.

Mass m/z: 357 $(M^+)$, 331, 301, 283, 256, 212, 148, 120, 91 (base) IR (KBr): 3298, 2968, 1791, 1656, 1608, 1506, 1452, 1392, 1242, 1161 $cm^{-1}$ $^1$H-NMR ($CDCl_3$): 1.23(s, 9H), 5.05(bs,3H), 6.94(d,J=8.3 Hz,2H), 7.32~7.41(m,8H)

Reference 4-c

Synthesis of Compound (84)

Benzyl (3S)-3-[4-(benzyloxy)phenyl]-3-[(tert-butoxy)carbonylamino]propionate

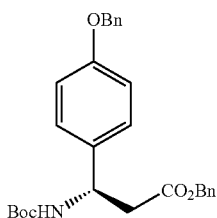

8-4

To a solution of the compound (8-3) (14.4 g) in tetrahydrofuran (80 mL) were added triethylamine (5.9 mL) and isobutylchloroformate (5.8 mL) at 0° C. After the mixture was stirred for 40 min, ether solution of diazomethane, prepared from N,N-dimethylnitrosourea (30.0 g) and 40% potassium hydroxide solution (100 mL), was added. The mixture was stirred for 1.5 hr and then quenched with acetic acid. Ether (100 mL) and water (100 mL) were added to the mixture. The separated organic layer was washed with satd.$Na_2CO_3$ solution (100 mL×2), brine (100 mL), dried ($Na_2SO_4$) and evapolated. To a solution of the residue in tetrahydrofuran (80 mL)-water (15 mL) was added a solution of silver benzoate (0.93 g) in triethylamine (8.3 mL). After the mixture was stirred at room temperature for 2 hr, the mixture was diluted with ether (100 mL). The ether solution was washed with 10% hydrochloric acid (50 mL×2), water (100 mL×4), brine (50 mL), dried ($Na_2SO_4$) and concentrated. To a solution of the residue in acetonitrile (80 mL) were added DBU (7.0 mL) and benzylbromide (5.7 mL). The mixture was stirred at room temperature for 4 hr and diluted with ethyl acetate. The ethyl acetate extract was washed successively with 10% citric acid solution (50 mL×2), satd.$Na_2CO_3$ (100 mL), brine (100 mL), dried ($Na_2SO_4$) and evapolated. The residue was purified by silica gel column chromatography (ethyl acetate/hexane=1/2) to give 10.35 g (55.7%) of the compound (8-4).

Mass m/z 461 $(M^+)$, 404, 360, 314, 270, 212, 180, 121, 91, 57 (base) IR (KBr) 3394, 2956, 1731, 1689, 1500, 1290, 1224, 1149 $cm^{-1}$ $^1$H-NMR($CDCl_3$): 1.51(s,9H), 2.89~3.12 (m,2H), 5.10(s,4H), 5.09~5.13(m,1H), 6.99(d, J=8.8 Hz,2H), 7.30~7.54(m,12H)

Reference 4-d

Synthesis of Compound (8-5)

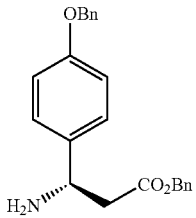

8-5

Benzyl (3S)-3-amino-[4-(benzyloxy)phenyl]propionate hydrochloride

To a solution of the compound (8-4) (3.00 g) in ethyl acetate (30 mL) was added 17% hydrochloric acid in ethanol (10 mL). The mixture was stirred for 3 hr and concentrated under reduced pressure. To the residue was added ethyl acetate-hexane (1/4) in order to crystallize. The resulting crystals were filtered and dried to give 2.46 g (95.2%) of the compound (8-5).

Mass m/z: 361 (M−36.5)+, 344, 270, 147, 121, 91 (base), 65 IR (KBr): 3016, 2908, 1725, 1581, 1512, 1299, 1245, 1185 cm−1 1H-NMR(CDCl3): 3.05(d,J=6.4 Hz,18.3 Hz,1H), 3.27(d,J=6.4 Hz,16.8 Hz,1H), 4.64~4.65(m, 1H), 4.94~5.03 (m,4H), 6.89(d,J=8.7 Hz,2H), 7.15~7.41(m,12H), 8.77~8.78 (m,3H)

Reference 4-e

Synthesis of Compound (8-6)

(4S)-4-[4-(benzyloxy)phenyl]azetidine-2-one

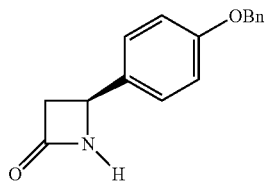

8-6

To a suspension of the compound (8-5) (6.48 g) in ethyl acetate were added water (15 mL) and 1 M potassium carbonate solution to make alkaline. The mixture was extracted with ethyl acetate (30 mL×2). The organic layer was washed with brine (50 mL), dried (Na2SO4) and evaporated. To a solution of the residue in benzene (60 mL) were added triethylamine (3.6 mL) and chlorotrimethylsilane (2.7 mL). The mixture was stirred at room temperature for 14 hr and filtered through a pad of Celite. The filtrate was evaporated under reduced pressure and the residue was dissolved in ether (65 mL) and a solution of 2 M tert-butylmagnesium chloride in ether (10.7 mL) was added at 0° C. and stirred at room temperature for 18 hr and then saturated ammonium chloride solution (50 mL), ethyl acetate (50 mL) and 10% hydrochloric acid (50 mL) were added successively at 0° C. After the resulting mixture was stirred at room temperature for 1 hr, the water layer was extracted with ethyl acetate. The combined ethyl acetate extracts was washed with water (50 mL), satd. NaHCO3 (50 mL), and brine (50 mL), dried (Na2SO4) and evaporated. The residue was purified by silica gel column chromatography (chloroform/acetone=10/1) to give the objective compound as a crude solid. This solid was purified by washing with ethyl acetate-hexane to give 2.50 g (60.7%) of the compound (8-6).

Mass m/z: 253 (M+), 162, 91 (base), 65 IR (KBr): 3184, 1749, 1698, 1540, 1410, 1248, 1100 cm−1 1H-NMR(CDCl3): 2.84~2.88(d,J=1.0 Hz,2.4 Hz,15.1 Hz,1H), 3.39~3.44(d, J=2.4 Hz, 5.4 Hz, 14.8 Hz,1H), 4.68(d,J=4.9 Hz,14.9 Hz,1H), 5.08(s,2H), 6.09(bs,1H), 6.97(d,J=2.9 Hz,7.8 Hz,2H), 7.28~7.44(m,7H)

Reference 4-f

Synthesis of (4S)-4-[4-(benzyloxy)phenyl]-1-(4-fluorophenyl)azetidine-2-one

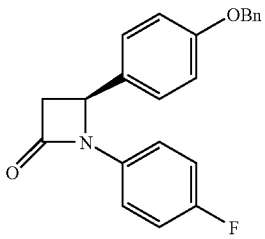

8-26

To a solution of the compound (8-6) (1.00 g) in dichloromethane (10 mL) were added triethylamine (0.8 mL), 4-fluorophenylboronic acid (1.11 g) and copper aceate (0.75 g). The mixture was refluxed for 48 hr and evaporated under reduced pressure. The residue was partitioned in ethyl acetate (50 mL) and water (50 mL). The water layer was extracted with ethyl acetate (50 mL×3). The combined ethyl acetate extracts were washed successively with water (50 mL), 10% hydrochloric acid (50 mL), saturated sodium bicarbonate solution (50 mL), and brine (50 mL), dried over anhydrous sodium sulfate and concentrated. The residue was purified by silica gel column chromatography (benzene/ether=12/1) to give a solid, which was recrystallized from ethyl acetate-hexane to give 1.06 g (77.3%) of the objective compound (8-26).

Mass m/z: 347 (M+), 256, 210, 137, 91 (base), 65 IR (KBr): 1731, 1620, 1506, 1380, 1242 cm−1 1H-NMR (CDCl3): 2.93(d,J=3.0 Hz,15.2 Hz,1H), 3.52(d,J=5.4 Hz, 15.2 Hz,1H), 4.93(d,J=2.4 Hz, 5.4 Hz,1H), 5.05(s,2H), 6.90~6.99(m,4H), 7.24~7.43(m,9H)

Reference 4-g

Synthesis of Compound (8-27)

(4S)-1-(4-fluorophenyl)-4-(hydroxyphenyl)azetidine-2-one

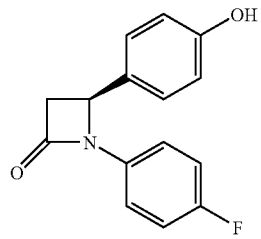

8-27

A solution of the compound 8-26 (2.00 g) obtained above step reference 4-f in ethyl acetate-methanol (50 mL) was hydrogenated at room temperature for 9 hr in the presence of 5% palladium on carbon (0.20 g). After removal of the catalyst through a pad of Celite, the solvent was evaporated and the residue was purified by silica gel column chromatography (chloroform/acetone=10/1) to give 1.36 g (91.9%) of the compound (8-27).

Mass m/z: 257 (M+), 214, 120(base), 91, 58 IR (KBr): 3106, 1707, 1620, 1503, 1453, 1383, 1257, 1218 cm−1 1H-NMR(CDCl3): 2.93(d,J=2.4 Hz,15.7 Hz, 1H), 3.53(d, J=5.9 Hz,15.2 Hz, 1H), 4.94(d,J=2.9 Hz, 5.4 Hz,1H), 5.22 (s,1H), 6.85(d,J=8.3 Hz,2H), 6.93(s,J=8.8 Hz,2H), 7.23~7.27(m,4H)

Reference 4-h

Synthesis of 4-[(2S)-1-(4-fluorophenyl)-4-oxoazetidine-2-yl]phenyltrifluoromethanesulfonate

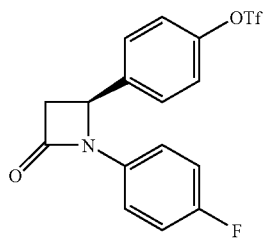

8-28

To a suspension of the compound (8-27) (0.35 g) in dichloromethane (10 mL) were added pyridine (0.12 mL) and trifluoromethanesulfonic anhydride (0.26 mL) at 0° C. The mixture was stirred for 1 hr and poured into ice-cold water (20 mL). The resulting mixture was extracted with ethyl acetate (30 mL×2). The combined ethyl acetate extracts were washed with 10% hydrochloric acid (20 mL), saturated sodium bicarbonate solution (40 mL), brine (30 mL), dried over anhydrous sodium sulfate and evaporated. The residue was purified by silica gel column chromatography (ethyl acetate/hexane=1/3) to give 0.48 g (90.7%) of the objective compound (8-28).

Mass m/z: 389 (M+), 347, 252, 214, 186, 137, 119 (base), 69 IR (KBr): 1734, 1509, 1416, 1383, 1248, 1212, 1131, 900 cm$^{-1}$ $^1$H-NMR(CDCl$_3$): 2.94(d,J=2.5 Hz,15.2 Hz, 1H), 3.16 (d,J=5.9 Hz,15.2 Hz, 1H), 5.04(d,J=2.5 Hz, 5.4 Hz,1H), 6.98(t,J=8.8 Hz,2H), 7.21~7.25(m,2H), 7.31(d,J=2.0 Hz,6.8 Hz,2H), 7.45(d, J=2.2 Hz,6.8 Hz,2H)

Reference 4-i

Synthesis of Compound (8-29)

(4S)-4-[4-{(2S,5S,3R,4R,6R)-6-[(benzyloxy)methyl]-3,4,5-tribenzyloxy}perhydro-2H-pyran-2-yl]methyl)phenyl]-1-(4-fluorophenyl)azetidine-2-one

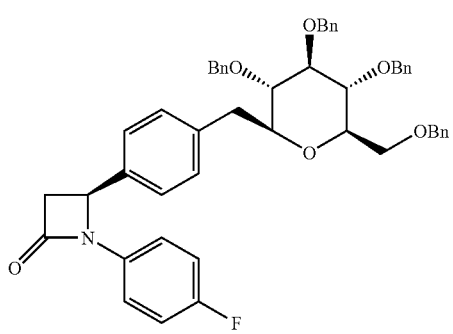

8-29

To a solution of the compound (8-28) (0.32 g) in tetrahydrofuran (4.1 mL) was added 0.5 M 9-BBN in tetrahydrofuran (3 mL) and the mixture was refluxed for 6 hr. After cooling to room temperature, 3 M potassium phosphate solution (0.6 mL), tetrahydrofuran (4.7 mL), the compound obtained in reference 4-h (0.22 g) and PdCl$_2$(dppf) (0.042 g) were added to the mixture and the resulting mixture was stirred at 50° C. for 16 hr. To the mixture were added water (30 mL) and ethyl acetate (30 mL) and the resulting mixture was filtered through a pad of Celite. The filtrate was extracted with ethyl acetate (30 mL×2). The combined ethyl acetate extracts were washed with water (30 mL×2) and brine (30 mL), dried over anhydrous sodium sulfate and evaporated. The residue was purified by silica gel column chromatography (ethyl acetate/hexane=1/4) to give 0.209 g (45.4%) of the compound (8-29).

Mass (ESI) m/z: 800 (M+Na(23))$^+$ IR (KBr): 2896, 1746, 1509, 1377, 1095, 1068, 750 cm$^{-1}$ $^1$H-NMR(CDCl$_3$): 2.69~2.75(d,J=7.8 Hz,14.7 Hz,1H), 2.89(d,J=2.5 Hz,15.1 Hz,1H), 3.12(d, J=1.5 Hz,14.2 Hz,1H), 3.30~3.37(m,2H), 3.46~3.53(m,2H), 3.59~3.74(m,8H), 4.45~4.64(m,4H), 4.81~4.94(m,5H), 6.90(t,J=8.8 Hz,2H), 7.19~7.35(m,26H)

Reference 4-j

Synthesis of Compound (8-30)

Methyl 3-{(4S,3R)-4-[4-{(2S,5S,3R,4R,6R)-6-(benzyloxymethyl)-3,4,5-tribenzyloxy}perhydro-2H-pyran-2-yl]methyl}phenyl]-1-(4-fluorophenyl)oxoazetidine-3-yl}propionate

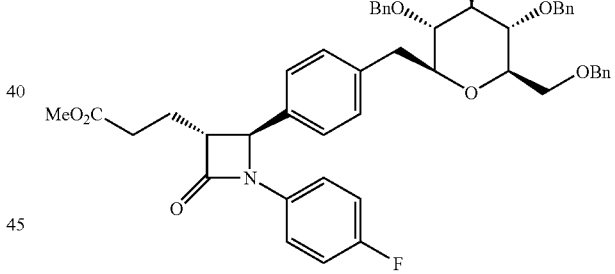

8-30

To a solution of 2 M lithium diisopropylamide (1.3 mL) in tetrahydrofuran (3 mL) was added a solution of the compound (8-29) (1.00 g) in tetrahydrofuran (1.5 mL) at −78° C. and the mixture was stirred for 1 hr and a solution of methyl acrylate (0.132 g) in tetrahydrofuran (2 mL) was added to the mixture. The resulting mixture was stirred for 0.5 hr and the mixture was quenched with saturated ammonium chloride solution (30 mL) and extracted with ethyl acetate (60 mL×2). The combined ethyl acetate extracts were washed with water (50 mL), dried over anhydrous sodium sulfate and evaporated. The residue was purified by silica gel column chromatography (ethyl acetate/hexane=1/4) to give 0.793 g (71.8%) of the compound (8-30).

Mass (ESI) m/z: 864 (M+1)$^+$ IR (KBr): 2854, 1740, 1509, 1452, 1362, 1215, 1140, 1098 cm$^{-1}$ $^1$H-NMR (CDCl$_3$): 2.19~2.23(m,2H), 2.47~2.59(m,2H), 2.72(d,J=8.8 Hz, 14.6 Hz,1H), 3.04~3.13(m,2H), 3.30~3.37(m,2H), 3.42~3.48(m, 1H), 3.64(s,3H), 3.61~3.74(m,4H), 4.47~4.63(m,5H), 4.81~4.94(m,4H), 6.90(t,J=8.8 Hz,2H), 7.15~7.35(m,26H)

Reference 4-k

Synthesis of Compound (8-31)

(4S,3R)-4-[4-({(2S,5S,3R,4R,6R)-6-(benzyloxy)methyl}-3,4,5-tribenzyloxy)perhydro-2H-pyran-2-yl]methyl)phenyl]-1-(4-fluorophenyl)-3-[3-(4-fluorophenyl)-3-oxopropyl]azetidine-2-on    8-31

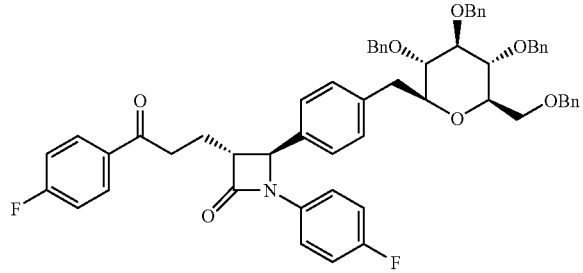

To a solution of the compound (8-30) (1.75 g) in tetrahydrofuran-methanol (20 mL) were added water (5 mL) and lithium hydroxide (0.084 g). The mixture was stirred at room temperature for 4 hr. The reaction mixture was acidified by addition of 10% hydrochloric acid and extracted with ethyl acetate (30 mL×3). The combined ethyl acetate extracts were concentrated under reduced pressure, and the residue was passed through a short silica gel column (ethyl acetate/hexane=1/1) to give the crude product which was subjected to the next reaction without further purification. To a solution of the compound obtained above in dichloromethane (8.4 mL) was added 2 M oxalyl chloride (0.84 mL) in dichloromethane and the mixture was stirred at room temperature for 16 hr. Removal of the organic solvent gave the crude acid chloride. To a suspension of zinc chloride (0.368 g) in tetrahydrofuran (8 mL) was added 4-fluorophenylmagnesium bromide, prepared from magnesium (0.084 g) and 4-bromofluorobenzene (0.47 g) in tetrahydrofuran (8 mL). The mixture was stirred at room temperature for 1 hr and tetrakis(triphenylphosphine)palladium (0.068 g) was added at 10° C. After the mixture was stirred for 5 min, the acid chloride obtained above in tetrahydrofuran (7 mL) was added. The resulting mixture was stirred at room temperature for 1 hr, and then quenched with 10% hydrochloric acid (20 mL). The mixture was extracted with ethyl acetate (50 mL×2). The organic layer was washed with water (50 mL×2) and brine (50 mL), dried over anhydrous sodium sulfate and evaporated. The residue was purified by silica gel column chromatography (ethyl acetate/hexane=1/5) to give 0.910 g (73.7%) of the compound (8-31).

Mass (ESI) m/z: 551 (M+Na(23)+1)$^+$ IR (KBr): 2920, 1746, 1690, 1610, 1310, 1280, 1240, 1100 cm$^{-1}$ $^1$H-NMR (CDCl$_3$): 2.23~2.42(m,2H), 2.72(d,J=8.8 Hz,14.7 Hz,1H), 3.09~3.74(m,11H), 4.46~4.63(m,4H), 4.66(d,J=2.5 Hz,1H), 4.81~4.94(m,4H), 6.91(t,J=8.8 Hz,2H), 7.11(t,J=8.3 Hz,2H), 7.33~7.89(m,26H), 7.96~8.00(m,2H)

Example 5

Synthesis of Compound (26)

(4S,3R)-4-(4-{[(2S,5S,3R,4R,6R)-3,4,5-trihydroxy-6-(hydroxymethyl)perhydro-2H-pyran-2-yl]methyl}phenyl)-1-(4-fluorophenyl)-3-[3-(4-fluorophenyl)-3-oxopropyl]azetidine-2-one    26

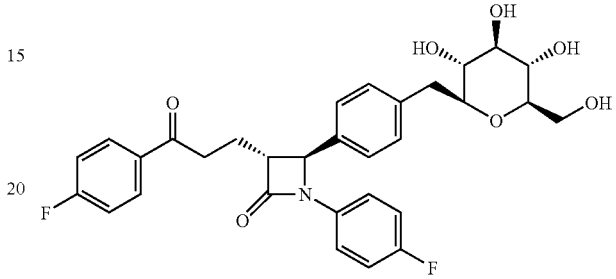

To a solution of the compound (8-31) (0.27 g) in dichloromethane (5.4 mL) was added 1 M borontribromide in dichloromethane (1.8 mL) at −78° C. and the mixture was stirred for 1 hr. The mixture was poured into ice-water (30 mL) and extracted with chloroform (30 mL×3). The combined chloroform extracts were washed successively with water (50 mL), saturated sodium bicarbonate solution (50 mL), and brine (50 mL), dried over anhydrous sodium sulfate and concentrated. The residue was purified by silica gel column chromatography (chloroform/methanol=8/1) to give 0.147 g (89.1%) of the compound (26).

Mass (ESI) m/z: 568 (M+1)$^+$ IR (KBr): 3400, 2902, 1737, 1680, 1596, 1506, 1386, 1224, 1152, 1134, 1086 cm$^{-1}$ $_1$H-NMR (CD$_3$OD): 2.28~2.34(m,2H), 2.74(d,J=8.3 Hz, 14.6 Hz,1H), 3.09~3.39(m,10H), 3.64(d,J=5.3 Hz, 11.7 Hz,1H), 3.78(d,J=2.4 Hz, 11.7 Hz,1H), 4.95(d,J=2.4 Hz,1H), 7.01~7.05(m,2H), 7.22~7.26(m,2H), 7.27~7.38(m, 6H), 8.06~8.10(m,2H)

Example 6

Synthesis of Compound (22)

3-[(3S)-3-(4-fluorophenyl)-3-hydroxypropyl]-(4S,3R)-4(4-[(2S,5S,3R,4R,6R)-3,4,5-trihydroxy-(hydroxymethyl)perhydro-2H-pyran-2-yl]methyl)phenyl)-1-(4-fluorophenyl)azetidine-2-one

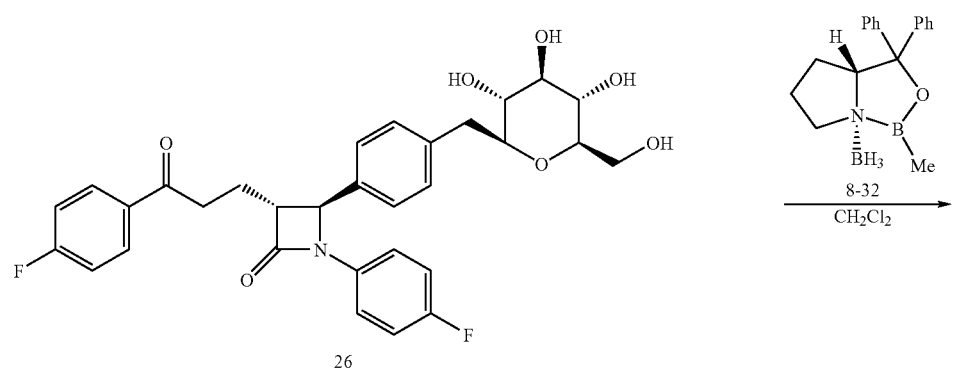

26

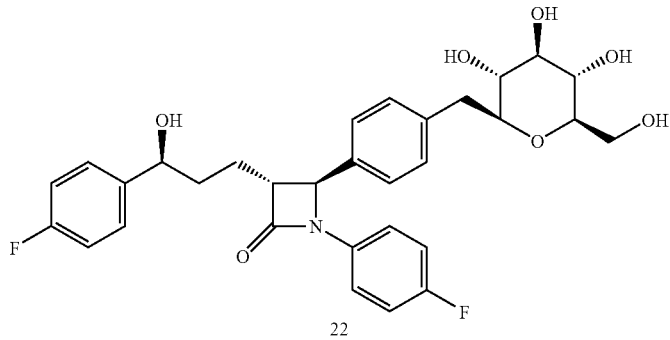

To a solution of the compound (8-32) (0.061 g) in dichloromethane (0.6 mL) was added the compound (26) (0.115 g) in dichloromethane (2.8 mL) at −20° C. and the mixture was stirred for 2 hr. The mixture was quenched by addition of methanol (2 mL) and stirred for 1 hr. Ethyl acetate (30 mL) and 10% hydrochloric acid (30 mL) were added and the resulting mixture was extracted with ethyl acetate (30 mL×3). The organic layer was washed with water (30 mL×3) and brine (50 mL), dried over anhydrous sodium sulfate and evaporated. The residue was purified by silica gel column chromatography (chloroform/methanol=10/1) to give 0.089 g (77.1%) of the compound (22).

Mass (ESI) m/z: 570 (M+1)$^+$ IR (KBr):3370, 2902, 1725, 1506, 1389, 1218, 1083, 1011 cm$^{-1}$ $^1$H-NMR (CD$_3$OD): 1.88~1.99(m,4H), 2.76(d,J=8.3 Hz, 14.2 Hz,1H), 3.09~3.40 (m,7H), 3.64(d,J=5.4 Hz, 11.5 Hz,1H), 3.79(d,J=2.0 Hz, 11.7 Hz,1H), 4.65(dt,J=4.8 Hz, 6.4 Hz,1H), 4.85(d,J=2.0 Hz,1H), 7.00~7.09(m,4H), 7.29~7.40(m,8H)

Example 7

Synthesis of Compound (8-33)

(4S,3R)-4-[4-{(2S,5S,3R,4R,6R)-6-[(Benzyloxy)methyl]-3,4,5-tribenzyloxy}perhydro-2H-pyran-2-yl]methyl)phenyl)-1-(4-fluorophenyl)-3-[(2E)-3-(4-fluorophenyl)-2-propenyl]azetidine-2-one

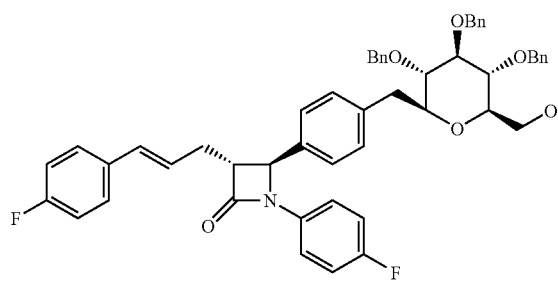

To a solution of the compound (8-29) in tetrahydrofuran (3 mL) was added 2 M lithium diisopropylamide (0.6 mL) in tetrahydrofuran at −78° C. and the mixture was stirred for 30 min. 1.8 mL of DMPU (1,3-dimethyl-3,4-5,6-tetrahydro-2(1H)-pyrimidinone) was added to the mixture and the mixture was stirred for 30 min. To the reaction mixture was added 4-fluorocinnamylbromide (0.111 g) in tetrahydrofuran (1.5 mL) and the resulting mixture was stirred for 30 min. The reaction mixture was quenched with a solution of saturated ammonium chloride solution (30 mL) and extracted with ethyl acetate (50 mL×2). The organic layer was washed successively with water (50 mL×3), brine (50 mL), dried over anhydrous sodium sulfate and evaporated. The residue was purified by silica gel column chromatography (ethyl acetate/hexane=1/5) to give 0.253 g (64.4%) of the compound (8-33).

Mass (ESI) m/z: 934 (M+Na(23))$^+$ IR (KBr): 2890, 1746, 1509, 1383, 1359, 1224, 1137, 1098 cm$^{-1}$ $^1$H-NMR (CDCl$_3$): 2.63~2.88(m,3H), 3.12(d,J=1.9 Hz, 14.7 Hz,1H), 3.20~3.38(m,4H), 3.47~3.48(m,1H), 3.59~3.74(m,5H), 4.45~4.63(m,4H), 4.65(d,J=2.4 Hz,1H), 4.81~4.94(m,4H), 6.12(dt,J=6.8 Hz, 14.6 Hz,1H), 6.45(d,J=14.7 Hz,1H), 6.90 (t,J=8.8 Hz,2H), 6.95(t,J=8.7 Hz,2H), 7.14~7.35(m,28H)

Example 8

Synthesis of Compound (25)

4-(4-{[(5S,2R,3R,4R,6R)-3,4,5-trihydroxy-6-(hydroxymethyl)perhydro-2H-pyran-2-yl]methyl}phenyl)-(4S,3R)-1-(4-fluorophenyl)-3-[3-(4-fluorophenyl)propyl]-azetidine-2-on

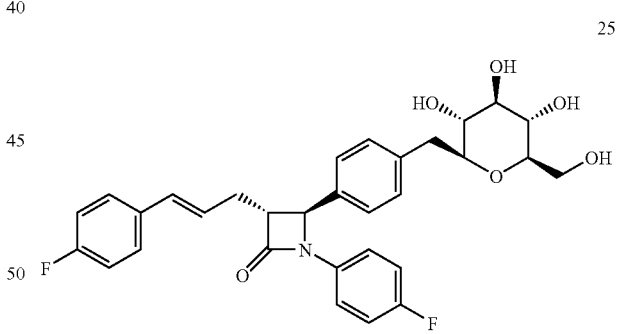

A solution of the compound (8-33) (0.23 g) in methanol-tetrahydrofuran (10 mL) was hydrogenated at room temperature for 5 hr in the presence of 5% palladium on carbon (0.115 g). After removal of the catalyst through a pad of Celite, the solvent was evaporated. The residue was purified by silica gel column chromatography (chloroform/methanol=9/1) to give 0.113 g (81.1%) of the compound (25).

Mass (ESI) m/z: 554 (M+1)$^+$ IR (KBr): 3394, 2908, 1737, 1506, 1386, 1218, 1089 cm$^{-1}$ $^1$H-NMR (CD$_3$OD): 1.88~1.95(m,4H), 2.66(t,J=7.3 Hz,2H), 2.75(d,J=8.3 Hz, 14.2 Hz,1H), 3.09~3.40(m,7H), 3.64(d,J=5.8 Hz, 11.7 Hz,1H), 3.78(d,J=2.5 Hz, 11.7 Hz,1H), 4.91(d,J=2.0 Hz, 1H), 6.97~7.04(m,4H), 7.18~7.33(m,6H), 7.38(d,J=8.3 Hz,2H)

Synthesis of Compound (11-3)

Methyl 5-(4-aza-10,10-dimethyl-3-dioxo-3-thiatricyclo[5,2,1,1,5]decane-4-yl)-5-oxopentanoate

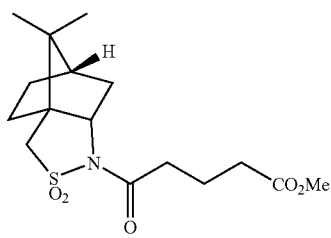

11-3

To a solution of (R)-(+)-2,10-camphorsultam (0.89 g) in toluene (14 mL) was added sodium hydride (0.182 g) at 0° C., and the mixture was stirred at room temperature for 20 min. To the reaction mixture was added methyl 5-chloro-5-oxo-valerate (0.816 g) and the resulting mixture was stirred at room temperature for 1 hr. The reaction mixture was quenched by addition of saturated ammonium chloride (40 mL) and extracted with ethyl acetate (50 mL×2). The organic layer was dried over anhydrous sodium sulfate and evaporated. The residue was purified by silica gel column chromatography (chloroform/acetone=40/1, then ethyl acetate/hexane=1/2) to give 1.30 g (91.8%) of the compound (11-3).

Mass m/z: 343 (M$^+$), 312, 279, 129 (base), 101 IR (KBr): 2944, 1720, 1689, 1440, 1413, 1389, 1335, 1215, 1050 cm$^{-1}$ $^1$H-NMR (CD$_3$OD): 0.97(s,3H), 1.16(s,3H), 1.35~1.41(m, 2H), 1.87~2.12(m,7H), 2.39(t, J=8.3 Hz,2H), 2.78(t,J=7.4 Hz,2H), 3.46(q,J=4.4 Hz,2H), 3.67(m,3H), 3.85~3.88(m, 1H)

Reference 5-b

Synthesis of compound (11-10)

Methyl (4R)-4-{(1S)-(4-bromophenyl[(4-fluorophenyl)amino]methyl)-5-(4-aza-10,10-dimethyl-,3-dioxo-3-thiatricyclo[5,2,1,1,5]decane-4-yl)-5-oxopentanoate

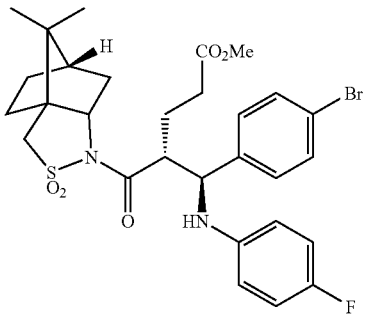

11-10

To a solution of titanium tetrachloride (0.23 mL) in dichloromethane (10 mL) was added titanium tetraisopropoxide (0.2 mL) at 0° C. and the mixture was stirred for 5 min. The compound (11-3) (0.65 g) in dichloromethane (3.5 mL) was added to the mixture and stirred for 5 min. Diisopropylethylamine (0.72 mL) was added to the mixture and stirred for 1 hr and then cooled to −20° C. (1Z)-1-aza-2-(4-bromophenyl)-1-(4-fluorophenyl)ethene (1.15 g) in dichloromethane (3.5 mL) was added at −20° C. and the resulting mixture was stirred for 3 hr. The reaction mixture was quenched by successive addition of acetic acid (1 mL) in dichloromethane (5 mL) and 10% hydrochloric acid (30 mL), and extracted with ethyl acetate (50 mL×2). The organic layer was washed successively with water (50 mL), saturated sodium bicarbonate solution (50 mL), brine (50 mL), dried over anhydrous sodium sulfate and evaporated. The residue was purified by silica gel column chromatography (chloroform/acetone=50/11 then ethyl acetate/hexane=1/2) to give 0.708 g (61.1%) of the compound (11-10).

Mass m/z: 622 (M+2)$^+$, 620 (M$^+$), 343, 278, 200, 135, 95 IR (KBr): 3376, 2944, 1734, 1683, 1509, 1437, 1269, 1131, 1059, 1008 cm$^{-1}$ $^1$H-NMR(CDCl$_3$): 0.95(s,3H), 0.95(s,3H), 1.24~1.39(m,2H), 1.60~2.04(m,5H), 2.28~2.33(m,2H), 3.45~3.57(m,3H), 3.62(s,3H), 3.79~3.91(m,1H), 4.56(t, J=9.3 Hz,1H), 4.95(d, J=10.2 Hz,1H), 6.34~6.38(m,2H), 6.71~6.76(m,2H), 7.17(d,J=8.3 Hz,2H), 7.41(d,J=8.3 Hz, 2H)

Reference 5-c

Synthesis of compound (11-11)

Methyl 3-{(4S,3R)-4-(4-bromophenyl)-1-(4-fluorophenyl)-2-oxoazetidine-3-yl}propionate

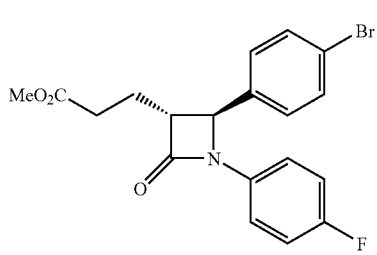

11-11

To a solution of the compound (11-10) (0.52 g) in toluene (10 mL) was added BSA (N,O-bistrimethylsilylacetamide, 0.41 g) at 50° C. and the mixture was stirred for 30 min. 1 M Tetrabutylammonium fluoride (0.84 mL) in tetrahydrofuran was added and the resulting mixture was stirred at 50° C. for 3 hr. After cooled to room temperature, the mixture was quenched with methanol (1 mL). The mixture was stirred for 5 min and then 10% hydrochloric acid (15 mL) was added. The mixture was extracted with ethyl acetate (50 mL×2). The organic layer was washed successively with water (50 mL), saturated sodium bicarbonate solution (50 mL), and brine (50 mL), dried over anhydrous sodium sulfate and evaporated. The residue was purified by silica gel column chromatography (ethyl acetate/hexane=1/3) to give 0.227 g (66.7%) of the compound (11-11).

Mass m/z: 407 (M+2)$^+$, 405 (M$^+$), 270, 208, 169, 129 (base), 95 IR (KBr): 2938, 1758, 1503, 1440, 1371, 1233, 1101 cm$^{-1}$ $^1$H-NMR(CDCl$_3$): 2.21~2.56(m,2H), 2.49~2.61 (m,2H), 3.08~3.12(m,1H), 3.67(s,3H), 4.66(d,J=2.5 Hz,1H), 6.92~6.97(m,2H), 7.18~7.22(m,4H), 7.51(d,J=1.9 Hz,6.3 Hz,2H)

Reference 6

Synthesis of Compound (12-4)

Methyl 3-{(4S,3R)-4-[4-(3-{(2S,5S,3R,4R,6R)-6-(benzyloxymethyl)-3,4,5-(tribenzyloxy) perhydro-2H-pyran-2-yl}-1-propen)phenyl]-1-(4-fluorophenyl)oxoazetidine-3-yl}propionate

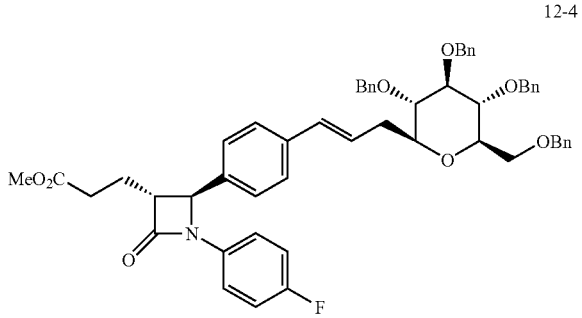

To a solution of the compound (11-11) (575 mg) and 3-(2,3,4,6-tetra-o-benzyl-β-D-glucopyranosyl)-1-propene (1.2 g) in triethylamine (5 mL) were added tri-o-tolylphosphine (43 mg) and palladium acetate (16 mg). The mixture was stirred at 100° C. for 13 hr. The mixture was cooled to room temperature and diluted with ethyl acetate (50 mL) and the ethyl acetate layer was washed with 10% hydrochloric acid, brine, dried over anhydrous sodium sulfate and evaporated. The residue was purified by silica gel column chromatography (ethyl acetate/hexane=1/4) to give 1.1 g (87.0%) of the compound (12-4).

This compound can be used as an intermediate for the synthesis of the compound depicted in general formula (I) in reference 4-l, 4-j, and 4-k, and example 5, 6, 7, and 8.

Mass (ESI) m/z: 890 (M+1)$^+$ IR (neat): 3016, 2896, 1741, 1503, 1371, 1215, 1092, 831, 747 cm$^{-1}$ $^1$H-NMR(CDCl$_3$): 2.23(q,J=7.8 Hz,2H), 2.44–2.60(m,4H), 3.11 (m,1H), 3.33–3.44(m,3H), 3.58–3.75(m,4H), 3.66(s,3H), 4.54–4.94 (m,9H), 6.38(m,2H), 6.91–7.32(m,28H)

Reference 7

Synthesis of Compound 50

(4S,3R)-3-[(3S)-3-(4-fluorophenyl)-3-hydroxypropyl]-4-(4-{[(2S,5S,3R,4R,6R)-3,4,5-trihydroxy-6-(hydroxymethyl)perhydro-2H-pyran-2-yl]methoxypropyl-3-yl}phenyl-1-(4-fluorophenyl)azetidine-2-one

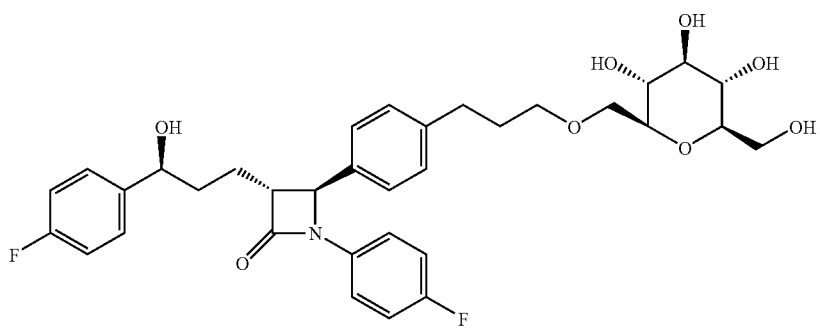

To a suspension of sodium hydride (4.5 mg) in DMF (N,N-dimethylformamide, 1 mL) was added 2,3,4,6-o-tetrabenzyl-1-deoxy-β-D-glucopyranosyl methanol (62 mg) in DMF (3 mL) at 0° C., and the mixture was stirred for 20 min. (4S,3R)-4-[4-(3-bromopropyl)phenyl]-3-[(3S)-(4-fluorophenyl)-3-hydroxypropyl]-2-azetidine-2-one (57 mg) in DMF (3 mL) and the resulting mixture was stirred at room temperature for 2 hr. The reaction mixture was poured into ice-cold water (20 mL) and extracted with ethyl acetate (30 mL×2). The organic layer was washed with water (30 mL×2) and brine (40 mL), dried over anhydrous sodium sulfate and evaporated. A solution of the residue in tetrahydrofuran-methanol (1/1) (10 mL) was hydrogenated at room temperature for 9 hr in the presence of 5% palladium on carbon (50 mg). After removal of the catalyst, the solvent was evaporated. The residue was purified by silica gel column chromatography (chloroform/methanol=10/1) to give 43 mg (61.2%) of the compound 50.

Mass (ESI) m/z: 628 (M+1)$^+$ IR (neat): 3388, 2902, 1734, 1509, 1389, 1218, 1080 cm$^{-1}$ $^1$H-NMR (CD$_3$OD): 1.87–1.97(m,6H), 2.73(t,J=7.4 Hz,2H), 3.10–3.5(m,1H), 3.12–3.39(m,5H), 3.52–3.57(m,2H), 3.53–3.69(m,2H), 3.78 (d,J=2.0 Hz,10.7 Hz,1H), 3.87(d,J=1.0 Hz, 10.5 Hz,1H), 4.64(bt,1H), 4.85(d,J=2.5 Hz,1H), 7.00–7.09(m,4H), 7.27–7.37(m,6H)

Example 9

Synthesis of Compound 19-9

(4S)-4-(4-{[(2S,5S,3R,4R,6R)-6-(benzyloxy)methyl-3,4,5-tribenzyloxy]perhydro-2H-pyran-2-yl}ethyl-phenyl)-1-phenyl-azetidine-2-one

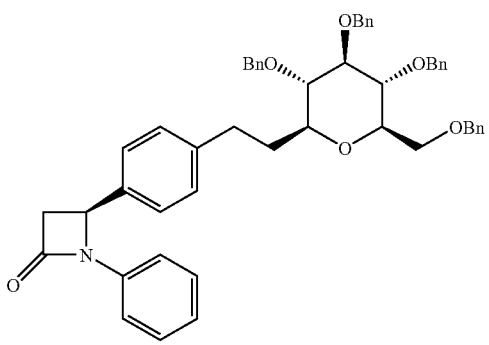

19-9

Reference 8-a

Synthesis of Compound (19-6)

(3R)-3-(4-Bromophenyl)-3-hydroxy-N-phenylpropanamide

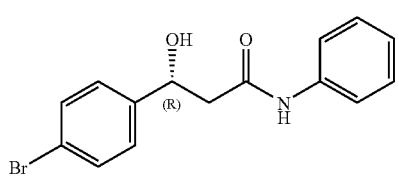

19-6

To a solution of 3-(4-bromophenyl)-3-oxo-N-phenylpropaneamide (950 mg) in ethanol-dichloromethane (3:1, 4 mL) was added RuCl$_2$[(S)-BINAP] (dichloro[(S)-(−)-2,2'-bis-(diphenylphosphino)-1,1'-binaphthyl]ruthenium(II)) cataltst (12 mg). The mixture was catalytic asymmetric hydrogenated at 100° C. for 6 hr under 5 atom H$_2$ atmosphere. After cooling to room temperature, the mixture was concentrated. The resulting crystals were corrected and dried to give 725 mg (yield 76%, asymmetric yield 99% e.e.) of the compound (19-6).

m.p.=210–212° C. [α]$^D$: +33.0 (c=1.0, THF) Mass m/z: 319 (M$^+$), 183, 157, 135, 93 (base), 65 IR (KBr): 3316, 1614, 1599, 1530, 1443, 1368, 1065, 693 cm$^{-1}$ $^1$H-NMR (DMSO): 2.69(dd,J=4.4 Hz,14.2 Hz,1H), 2.77(dd,J=8.8 Hz,14.2 Hz,1H), 5.16(n,1H), 5.69(d,J=4.4 Hz,1H), 7.14(t, J=7.3 Hz,1H), 7.40(d,J=7.8 Hz,2H), 7.46(d, J=8.3 Hz,2H), 7.64(d,J=8.3 Hz,2H), 7.69(d,J=7.8 Hz,2H)

Reference 8-b

Synthesis of Compound (19-7)

(4S)-4-(4-Bromophenyl)-1-phenyl-azetidine-2-one

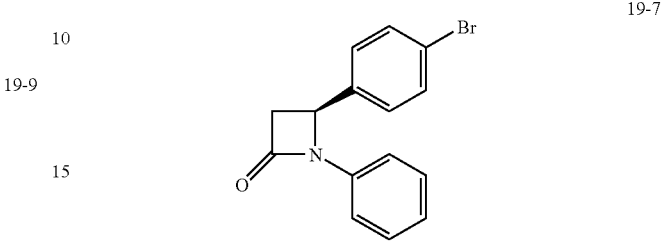

19-7

To a solution of the compound (19-6) (500 mg) in tetrahydrofuran (7 mL) were added DIAD (diisopropylazodicarboxylate) (0.67 mL) and PPh$_3$ (479 mg) at −78°. The mixture was slowly warmed to room temperature and stirred for 4 hr. The mixture was concentrated, and the residue was purified by silica gel column chromatography (ethyl acetate/hexane=1/5 to 1/2) to give 260 mg (55.2%) of the compound 19-7.

m.p.=113–115° C. [α]$^D$: −146.0 (c=1.0, CHCl$_3$) Mass m/z: 301 (M$^+$), 260, 184, 103, 77 (base) IR (KBr): 1728, 1599, 1485, 1377, 1149, 828, 750 cm$^{-1}$ $^1$H-NMR (CDCl$_3$): 2.91(dd,J=2.9 Hz,15.1 Hz,1H), 3.56(dd,J=5.4 Hz,15.1 Hz,1H), 4.98(dd,J=2.4 Hz,5.9 Hz,1H), 7.04–7.52(m,9H)

Synthesis of Compound (19-9)

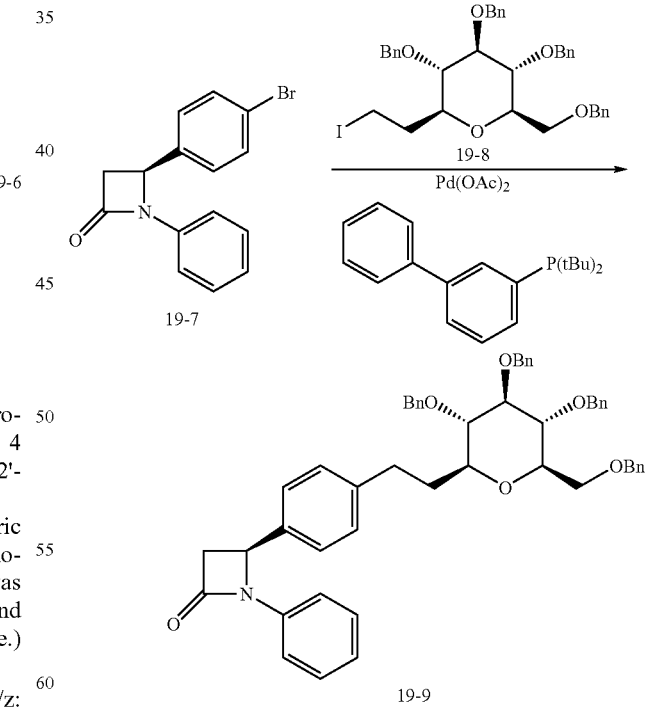

To a solution of Zn(Cu) (106 mg) in tetrahydrofuran-HMPA (3:1, 4 mL) was added the compound (19-8) (1.0 g), and the mixture was refluxed for 3 hr. Palladium acetate (1.7 mg) and 2-(di-tert-butylphosphino)biphenyl (4.4 mg) were added to the mixture at 0° C. After 5 min, the compound (19-7) (223 mg) was added, and the mixture was warmed to room temperature. 10% aqueous HCl (50 mL) and ethyl acetate (30 mL) were added to the mixture, and filtered. The filtrate was extracted with ethyl acetate (50 mL×2). The organic layer was washed with water (50 mL) and brine (50 mL), dried over anhydrous sodium sulfate and evaporated. The residue was purified by silica gel column chromatography (ethyl acetate/hexane=1/4) to give 480 mg (84.3%) of the compound (19-9).

m.p.=95–97° C. $[\alpha]^D$: −61.2 (c=1.0, $CHCl_3$) ESI-MS (m/z): 796 $(M+Na)^+$, 774$(M+1)^+$ IR (KBr): 2854, 1749, 1599, 1497, 1452, 1371, 1212, 1068 $cm^{-1}$ $^1$H-NMR ($CDCl_3$): 1.71–1.75(m,1H), 2.04–2.10(m,1H), 2.63–2.74(m,1H), 2.81–2.87(m,1H), 2.94(dd,J=2.4 Hz,15.1 Hz,1H), 3.18–3.22(m,1H), 3.29(t,J=13.1 Hz,1H), 3.36–3.40(m,1H), 3.53(dd,J=5.9 Hz, 5.1 Hz,1H), 3.59–3.75(m,4H), 4.55–4.66 (m,4H), 4.80–4.88(m,4H), 4.96–4.98(m,1H), 7.02(t,J=6.8 Hz,1H), 7.14–7.37(m,28H)

EFFECT OF THE INVENTION

This invention concerns to novel β-lactam compounds which are metabolically and hydrolytically stable against β-glycosidases, acids and bases and having C-glycosides in the molecules and exert strong plasma cholesterol lowering effects and useful as plasma hypolipidemic agents.

The invention claimed is:

1. The compounds have the following general formula (I);

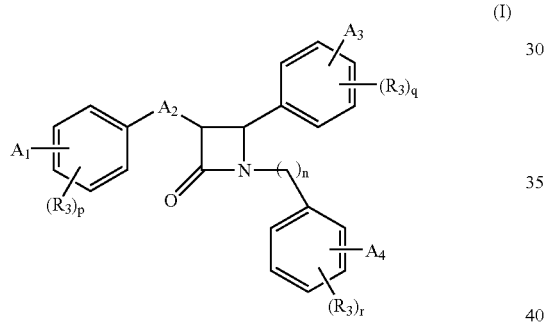

(I)

wherein, $A_1$, $A_3$ and $A_4$ are hydrogen atom, halogen atom, alkyl group having one to five carbon atoms, alkoxy group having one to five carbon atoms, —$COOR_1$, a following formula (b);

(b)

wherein, $R_1$ is hydrogen atom or alkyl group having one to five carbon atoms, or a following formula (a);

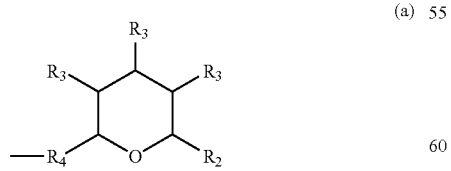

(a)

wherein, $R_2$ is —$CH_2OH$ group, —$CH_2OC(O)$—$R_1$ group or —$CO_2$—$R_1$ group, $R_3$ is —OH group or —OC(O)—$R_1$ group, $R_4$ is —$(CH_2)_kR_5(CH_2)_l$— group wherein, $0 \leq (k+l) \leq 10$, further $R_5$ means bond which is single bond —, —CH=CH—, —$OCH_2$—, carbonyl group or —CH(OH)—, and $R_4$ connects with tetrahydropyrane ring by carbon-carbon bond, and one of $A_1$, $A_3$ and $A_4$ in formula (I) is must be the group in above mentioned formula (a), further $A_2$ is alkylene group having one to five carbon atoms, —O-alkylene having two to five carbon atoms, alkenylene group having two to five carbon atoms, alkylene group substituted by an OH group having two to five carbon atoms or alkylene group substituted by an oxo group having two to five carbon atoms, n, p, q or r are 0, 1 or 2, or their pharmaceutical acceptable salts.

2. A method of preparing the compounds of claim 1, formula (I) and their pharmaceutically acceptable salts comprising Staudinger or Mannich reactions of the compounds of general formula (II);

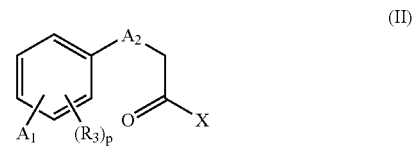

(II)

wherein: $A_1$, $A_2$, $R_3$ and p are as defined; X is leaving group selected from the group consisting of halogen atom and optically active isothiazolidonyl sultam, and the compounds of formula (III);

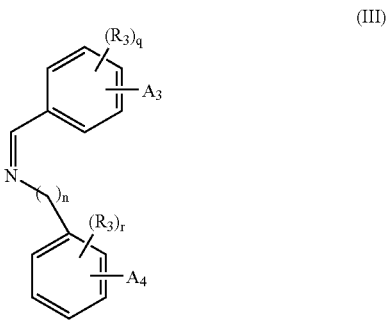

(III)

wherein, $A_3$, $A_4$, $R_3$, n, q and r are as defined.

3. A method of preparing the compounds of claim 1, formula (I) and their pharmaceutically acceptable salts comprising reaction of an anion derived from the compounds of formula (IV);

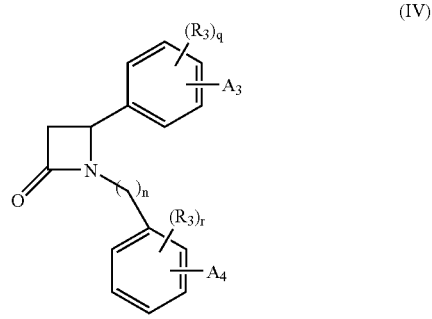

(IV)

wherein, n, q, r, $A_3$, $A_4$ and $R_3$ are as defined, and the compounds of formula (V);

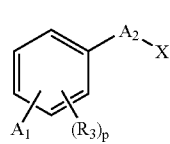
(V)

wherein, $A_1$, $A_2$, p, and $R_3$ are as defined, and X is leaving group selected from the group consisting of halogen atom and optically active sultam,
in the presence of base.

4. A method of preparing the compounds of claim 1, formula (I) and their pharmaceutically acceptable salts comprising cyclization of the compounds of formula (VI);

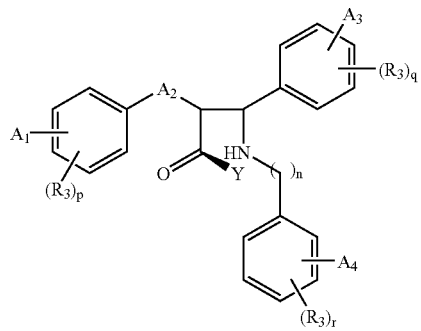
(VI)

wherein: n, p, q, r, $A_1$, $A_2$, $A_3$, $A_4$, and $R_3$ are as defined, and Y is an optically active isothiazolidonyl sultam,
to produce compounds of formula (I) and their pharmaceutically acceptable salts.

5. A method of preparing the compounds of formula (VII) and their pharmaceutically acceptable salts;

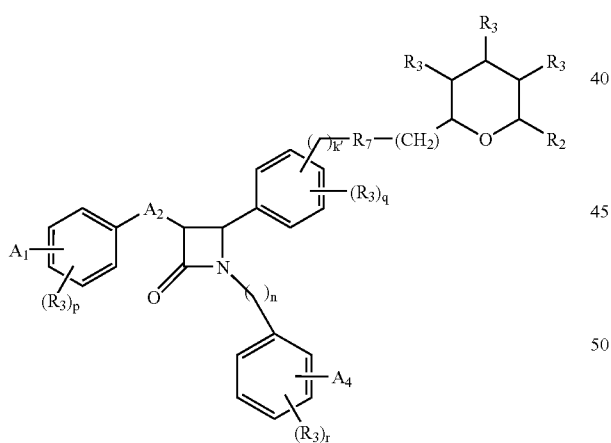
(VII)

wherein, $A_1$ and $A_4$ are hydrogen atom, halogen atom, alkyl group having one to five carbon atoms, alkoxy group having one to five carbon atoms, —$COOR_1$, a following formula (b);

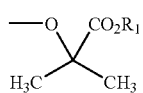
(b)

wherein, $R_1$ is hydrogen atom or alkyl group having one to five carbon atoms, or a following formula (a);

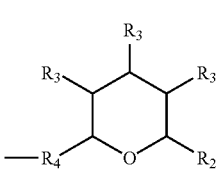
(a)

wherein, $R_2$ is —$CH_2OH$ group, —$CH_2OC(O)$—$R_1$ group or —$CO_2$—$R_1$ group, $R_3$ is —OH group or —OC(O)—$R_1$ group, $R_4$ is —$(CH_2)_kR_5(CH_2)_l$— group wherein $0 \leq (k+l) \leq 10$, further $R_5$ means a bond which is a single bond —, —CH=CH—, —$OCH_2$—, carbonyl group or —CH(OH)— and $R_4$ connects with tetrahydropyrane ring by a carbon-carbon bond, $A_2$ is an alkylene group having one to five carbon atoms, an —O-alkylene having two to five carbon atoms, alkenylene group having two to five carbon atoms, an alkylene group substituted by an OH group having two to five carbon atoms or an alkylene group substituted by an oxo group having two to five carbon atoms, and n, p, q or r are 0, 1 or 2;

$R_7$ is single bond —, —CH=CH—, —$OCH_2$—, $1 \leq k' \leq 10$; comprising coupling reaction of the compounds of formula (VIII)

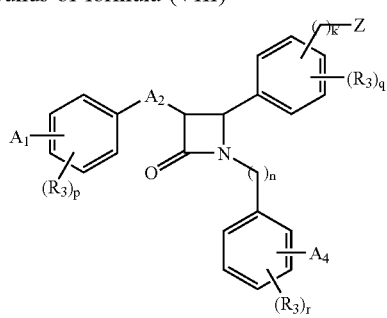
(VIII)

wherein, $A_1$, $A_2$, $A_4$, $R_3$, n, p, q and r are as defined; Z is a leaving group selected from the group consisting of halogen atom and triflate; and n, p, q or r are 0, 1 or 2 and $0 \leq k' \leq 10$, and the compounds of formula (IX)

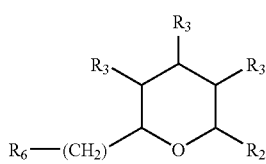
(IX)

wherein, $R_2$ and $R_3$ are as defined, $R_6$ is a halogen atom, —CH=$CH_2$, —$CH_2OH$.

6. Serum hypocholesterolemic agents containing the compounds of claim 1 formula (I) and their pharmaceutically acceptable salts and a pharmaceutically acceptable carrier.

7. Serum hypocholesterolemic agents obtained by combination of the compounds of claim 1 formula (I) and β-lactamase inhibitors and a pharmaceutically acceptable carrier.

* * * * *